United States Patent
Tucker-Schwartz et al.

(10) Patent No.: US 12,429,427 B2
(45) Date of Patent: Sep. 30, 2025

(54) COMPOSITIONS AND METHODS FOR ASSAY MEASUREMENTS

(71) Applicant: Meso Scale Technologies, LLC., Rockville, MD (US)

(72) Inventors: Alexander K. Tucker-Schwartz, Bethesda, MD (US); George Sigal, Rockville, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 464 days.

(21) Appl. No.: 17/363,758

(22) Filed: Jun. 30, 2021

(65) Prior Publication Data

US 2022/0018785 A1    Jan. 20, 2022

Related U.S. Application Data

(60) Provisional application No. 63/047,167, filed on Jul. 1, 2020.

(51) Int. Cl.
| | | |
|---|---|---|
| *G01N 21/76* | (2006.01) | |
| *G01N 33/543* | (2006.01) | |
| *G01N 33/58* | (2006.01) | |

(52) U.S. Cl.
CPC ......... *G01N 21/76* (2013.01); *G01N 33/5438* (2013.01); *G01N 33/582* (2013.01); *G01N 2458/30* (2013.01)

(58) Field of Classification Search
CPC .. G01N 21/76; G01N 2458/30; G01N 33/542; G01N 33/5438; G01N 33/582
See application file for complete search history.

(56) References Cited

U.S. PATENT DOCUMENTS

| | | |
|---|---|---|
| 5,093,268 A | 3/1992 | Leventis et al. |
| 5,147,806 A | 9/1992 | Kamin et al. |
| 5,238,808 A | 8/1993 | Bard et al. |
| 5,240,863 A | 8/1993 | Shibue et al. |
| 5,308,754 A | 5/1994 | Kankare et al. |
| 5,324,457 A | 6/1994 | Zhang et al. |
| 5,589,136 A | 12/1996 | Northrup et al. |
| 5,591,581 A | 1/1997 | Massey et al. |
| 5,597,910 A | 1/1997 | Gudibande et al. |
| 5,641,623 A | 6/1997 | Martin |
| 5,643,713 A | 7/1997 | Liang et al. |
| 5,679,519 A | 10/1997 | Oprandy |
| 5,705,402 A | 1/1998 | Leland et al. |
| 5,714,089 A | 2/1998 | Bard et al. |
| 5,731,147 A | 3/1998 | Bard et al. |
| 5,776,672 A | 7/1998 | Hashimoto et al. |
| 5,786,141 A | 7/1998 | Bard et al. |
| 5,846,485 A | 12/1998 | Leland et al. |
| 5,866,434 A | 2/1999 | Massey et al. |
| 5,935,779 A | 8/1999 | Massey et al. |
| 5,993,740 A | 11/1999 | Niiyama et al. |
| 6,066,448 A | 5/2000 | Wohlstadter et al. |
| 6,090,545 A | 7/2000 | Wohlstadter et al. |
| 6,136,268 A | 10/2000 | Ala-Kleme et al. |
| 6,140,045 A | 10/2000 | Wohlstadter et al. |
| 6,207,369 B1 | 3/2001 | Wohlstadter et al. |
| 6,316,607 B1 | 11/2001 | Massey et al. |
| 6,451,225 B1 | 9/2002 | Leland et al. |
| 6,468,741 B1 | 10/2002 | Massey et al. |
| 6,479,233 B1 | 11/2002 | Bard et al. |
| 6,808,939 B2 | 10/2004 | Sigal et al. |
| 6,919,173 B2 | 7/2005 | Tsionsky et al. |
| 6,977,722 B2 | 12/2005 | Wohlstadter et al. |
| 7,288,410 B2 | 10/2007 | Tsionsky et al. |
| 7,491,540 B2 | 2/2009 | Tsionsky et al. |
| 7,842,246 B2 | 11/2010 | Wohlstadter et al. |
| 8,785,201 B2 | 7/2014 | Tsionsky et al. |
| 9,416,150 B2 | 8/2016 | Bergmann et al. |
| 9,499,573 B2 | 11/2016 | Bergmann et al. |
| 9,618,510 B2 | 4/2017 | Aghvanyan et al. |
| 9,731,297 B2 | 8/2017 | Glezer et al. |
| 9,891,221 B2 | 2/2018 | Tsionsky et al. |
| 10,114,015 B2 | 10/2018 | Glezer et al. |
| 10,408,823 B2 | 9/2019 | Aghvanyan et al. |

(Continued)

FOREIGN PATENT DOCUMENTS

| | | |
|---|---|---|
| AU | 2008200361 A1 | 2/2008 |
| CN | 106124753 A | 11/2016 |

(Continued)

OTHER PUBLICATIONS

Rayer et al., "Dissociation Constants (pKa) of Tertiary and Cyclic Amines: Structural and Temperature Dependences," J. Chem. Eng. Data, 2014, 59, 11, pp. 3805-3813.*

Voinescu et al., "Similarity of Salt Influences on the pH of Buffers, Polyelectrolytes, and Proteins," J. Phys. Chem. B, 2006, vol. 110, pp. 8870-8876.*

Persson, "Implementation of electrochemiluminescence technology for quantification of bioprocess impurities", Uppsala University School of Engineering, 2008, Master's Thesis, pp. 1-50.*

A printout Lewis et al., "MSD™ Technology: A New Way to Measure Classic Markers of Apoptosis," pp. 1-10, retrieved from https://www.mesoscale.com/~/media/files/scientific%20poster/apoptosis markers.pdf on Jan. 3, 2023.*

(Continued)

*Primary Examiner* — Galina M. Yakovleva
(74) *Attorney, Agent, or Firm* — MEDLER FERRO WOODHOUSE & MILLS PLLC

(57) ABSTRACT

The invention relates to novel compositions comprising an electrochemiluminescence (ECL) co-reactant. In embodiments, the composition further comprises an ionic component, a surfactant, or combination thereof. In embodiments, the ECL co-reactant is triethanolamine (TEA), tert-butyldiethanolamine (tBDEA), methyldiethanolamine (MDEA), 3-[Bis-(2-hydroxy-ethyl)-amino]-propane-1-sulfonic acid (DEA-PS), or a combination thereof. Methods of using the compositions and kits comprising the compositions are also provided herein.

17 Claims, 22 Drawing Sheets

(56) References Cited

U.S. PATENT DOCUMENTS

| | | | |
|---|---|---|---|
| 10,753,934 | B2 | 8/2020 | Tsionsky et al. |
| 11,927,592 | B2 | 3/2024 | Tucker-Schwartz et al. |
| 12,203,937 | B2 | 1/2025 | Tucker-Schwartz et al. |
| 2011/0065135 | A1 | 3/2011 | Okamura et al. |
| 2012/0178091 | A1 | 7/2012 | Glezer et al. |
| 2012/0190586 | A1 | 7/2012 | Waters et al. |
| 2012/0190589 | A1 | 7/2012 | Anderson et al. |
| 2014/0367278 | A1 | 12/2014 | Zaworski et al. |
| 2017/0168047 | A1 | 6/2017 | Aghvanyan et al. |
| 2018/0364175 | A1 | 12/2018 | Josel et al. |
| 2019/0011441 | A1 | 1/2019 | Glezer et al. |
| 2021/0109100 | A1 | 4/2021 | Tsionsky et al. |
| 2022/0018846 | A1* | 1/2022 | Tucker-Schwartz ... G01N 21/66 |
| 2022/0373554 | A1 | 11/2022 | Tucker-Schwartz et al. |
| 2025/0102511 | A1 | 3/2025 | Tucker-Schwartz et al. |

FOREIGN PATENT DOCUMENTS

| | | |
|---|---|---|
| CN | 106526183 A | 3/2017 |
| CN | 109444116 A | 3/2019 |
| CN | 108698047 B | 4/2022 |
| JP | H08502586 A | 3/1996 |
| JP | 2001021560 A | 1/2001 |
| WO | 1990/005296 A1 | 5/1990 |
| WO | 1996/021154 A1 | 7/1996 |
| WO | 97/36931 A1 | 10/1997 |
| WO | 98/12539 A1 | 3/1998 |
| WO | 98/57154 A1 | 12/1998 |
| WO | 1999/014599 A1 | 3/1999 |
| WO | 99/32662 A1 | 7/1999 |
| WO | 99/58962 A1 | 11/1999 |
| WO | 99/63347 A2 | 12/1999 |
| WO | 00/03233 A1 | 1/2000 |
| WO | 2003/023380 A1 | 3/2003 |
| WO | 2014/160192 A1 | 10/2014 |
| WO | 2014/165061 A1 | 10/2014 |
| WO | 2015/175856 A1 | 11/2015 |
| WO | 2020/142313 A1 | 7/2020 |

OTHER PUBLICATIONS

Leland et al., "Electrogenerated Chemiluminescence: An Oxidative-Reduction Type ECL Reaction Sequence Using Tripropyl Amine," J. Electrochem. Soc., 1990, vol. 137, pp. 3127-3131.*

Workman et al., "The Effects of Nonionic Surfactants on the Tris(2,2'-bipyridyl)ruthenium(II)-Tripropylamine Electrochemiluminescence System," Anal. Chem., 2000, 72, 22, pp. 5556-5561.*

Zheng, L., et al. "Electrochemiluminescent behavior of Tris(2,2-bipyridine) Ruthenium(II)/Triethanolamine in ionic liquid solution". Journal of Physical Chemistry C, 112(39):15570-15575 (2008).

Lorenz, C., et al. Interference assessment of various endogenous and exogenous substances on the performance of the eversense long-term implantable continuous glucose monitoring system. Diabetes Technology & Therapeutics, 20(5):344-352 (2018).

Wu, S., et al. Determining the critical micelle concentrations of surfactants by a simple and fast titration method. Anal. Chem., 92(6):4259-4265 (2020).

Chen et al., "A simple and versatile paper-based electrochemiluminescence biosensing platform for hepatitis B virus surface antigen detection," Biochemical Engineering Journal 129: 1-6 (2017).

Debad et al., "Clinical and Biological Applications of ECL" in Electrogenerated Chemiluminescence, 1$^{st}$ Edition, 2004, CRC Press; pp. 43-78.

Han, Shuang et al., "Effect of Hydroxyl and Amino Groups on Electrochemiluminescence Activity of Tertiary Amines at Low tris(2,2'-bipyridyl)ruthenium(II) Concentrations" (Abstract), Talanta 81(1-2):44-47 (2010).

Hu et al., "Applications and trends in electrochemiluminescence," Chemical Society Reviews, 39: 3275-3304 (2010).

Kirschbaum-Harriman et al., "Signal enhancement and low oxidation potentials for miniaturized ECL biosensors via N-butyldiethanolamine", Analyst 142(13):2469-2474 (2017).

Kirschbaum-Harriman et al., "Improving ruthenium-based ECL through nonionic surfactants and tertiary amines," Analyst 142(14):2648-2653 (2017).

Kitte et al., "Electrogenerated chemiluminescence of tris(2,2'-bipyridine) ruthenium(II) using N-(3-aminopropyl)diethanolamine as coreactant", Anal Bioanal Chem 408(25):7059-7065 (2016).

Wang et al., "Label free bifunctional electrochemiluminescence aptasensor for detection of adenosine and lysozyme," Electrochimica Acta, 76: 416-423 (2012).

International Search Report issued Apr. 22, 2020, in PCT/US2019/068293.

Non-Final Office Action in U.S. Appl. No. 17/264,489 dated Oct. 5, 2023.

Final Office Action in U.S. Appl. No. 17/264,489 dated Jan. 29, 2024.

Issue Notification in U.S. Appl. No. 17/813,722 dated Feb. 21, 2024.

Notice of Allowability in U.S. Appl. No. 17/813,722 dated Feb. 9, 2024.

Notice of Allowability in U.S. Appl. No. 17/813,722 dated Nov. 2, 2023.

Notice of Allowability in U.S. Appl. No. 17/813,722 dated Nov. 15, 2023.

Final Office Action in U.S. Appl. No. 17/813,722 dated Apr. 20, 2023.

Non-Final Office Action in U.S. Appl. No. 17/813,722 dated Jan. 11, 2023.

Crespo et al., "Electrogenerated Chemiluminescence for Potentiometric Sensors," Journal of the American Chemical Society 134:205-207 (2012).

Wang et al., "Electrochemical and Electrogenerated Chemiluminescent Studies of a Trinuclear Complex, [((phen)$_2$Ru(dpp))$_2$RhCl$_2$]$^{5+}$, and Its Interactions with Calf Thymus DNA," Anal. Chem. 81:4068-4075 (2009).

Notice of Allowance in U.S. Appl. No. 17/264,489 dated Sep. 9, 2024.

Corrected Notice of Allowability in U.S. Appl. No. 17/264,489 dated Sep. 19, 2024.

Corrected Notice of Allowability in U.S. Appl. No. 17/264,489 dated Nov. 5, 2024.

Yin et al., "The Factors Affecting the Electrochemiluminescence of Tris(2,2'-bipyridyl)Ruthenium(II)/Tertiary Amines," Electroanalysis 20(10):1085-1091 (2008).

* cited by examiner

|  | Assay | Standard 2-Step | | | | 1 Step | | | | Mock ECL label | | | |
|---|---|---|---|---|---|---|---|---|---|---|---|---|---|
|  |  | TPA | BDEA | PIPES | 1.2 M TEA | TPA | BDEA | PIPES | 1.2 M TEA | TPA | BDEA | PIPES | 1.2 M TEA |
| ECL | IFN-γ | 10,414 | 10,527 | 1,703 | 5,214 | 25,457 | 11,949 | 1,379 | 5,664 | 85,673 | 70,777 | 4,691 | 12,471 |
|  | IL-1β | 75,574 | 64,396 | 12,857 | 32,685 | 71,309 | 51,221 | 8,624 | 33,184 | 161,965 | 130,693 | 15,311 | 43,668 |
|  | IL-2 | 90,866 | 88,271 | 19,963 | 33,634 | 75,501 | 68,319 | 12,133 | 36,617 | 172,589 | 154,141 | 23,684 | 44,091 |
|  | IL-4 | 81,019 | 85,406 | 14,087 | 32,655 | 55,938 | 52,129 | 8,035 | 32,565 | 136,226 | 125,887 | 18,890 | 42,085 |
|  | IL-6 | 98,891 | 89,491 | 17,475 | 46,365 | 84,829 | 71,017 | 9,258 | 45,882 | 179,342 | 153,444 | 23,144 | 51,973 |
|  | IL-8 | 43,563 | 42,067 | 9,834 | 21,054 | 81,099 | 40,792 | 6,139 | 23,405 | 127,180 | 107,491 | 15,537 | 29,064 |
|  | IL-10 | 53,009 | 56,204 | 10,255 | 28,201 | 58,624 | 46,839 | 5,805 | 28,357 | 130,383 | 116,538 | 14,152 | 33,791 |
|  | IL12p70 | 43,580 | 43,700 | 7,624 | 20,426 | 48,426 | 37,091 | 3,974 | 21,504 | 113,482 | 101,841 | 10,743 | 27,729 |
|  | IL-13 | 30,578 | 42,708 | 8,162 | 19,438 | 50,140 | 40,839 | 4,191 | 22,929 | 110,400 | 109,417 | 12,659 | 28,254 |
|  | TNF-α | 23,705 | 21,397 | 5,086 | 11,532 | 43,698 | 23,474 | 3,192 | 13,604 | 97,602 | 83,672 | 6,888 | 19,388 |
|  | Average | 55,120 | 52,416 | 10,705 | 24,920 | 57,502 | 44,367 | 6,073 | 26,371 | 131,484 | 115,390 | 14,726 | 33,250 |
| NSB ECL | IFN-γ | 249 | 379 | 190 | 287 | 18,921 | 4,092 | 524 | 437 | 73,860 | 59,417 | 3,394 | 7,021 |
|  | IL-1β | 652 | 784 | 390 | 402 | 21,780 | 3,910 | 1,158 | 637 | 80,780 | 64,604 | 3,847 | 7,624 |
|  | IL-2 | 438 | 429 | 373 | 284 | 22,100 | 4,431 | 1,053 | 684 | 82,537 | 63,978 | 5,414 | 7,417 |
|  | IL-4 | 135 | 134 | 82 | 155 | 23,961 | 4,726 | 683 | 568 | 73,478 | 59,815 | 4,486 | 8,738 |
|  | IL-6 | 160 | 145 | 82 | 162 | 24,289 | 4,794 | 650 | 754 | 76,258 | 62,046 | 3,398 | 7,170 |
|  | IL-8 | 168 | 153 | 108 | 178 | 31,727 | 10,030 | 1,062 | 1,856 | 81,793 | 63,218 | 5,296 | 7,317 |
|  | IL-10 | 226 | 254 | 154 | 212 | 25,097 | 5,614 | 797 | 1,282 | 79,671 | 60,323 | 4,756 | 7,196 |
|  | IL12p70 | 242 | 342 | 159 | 253 | 25,501 | 6,673 | 602 | 1,511 | 69,129 | 57,119 | 3,403 | 6,806 |
|  | IL-13 | 151 | 146 | 132 | 164 | 28,449 | 8,829 | 861 | 1,993 | 75,767 | 61,766 | 4,343 | 6,891 |
|  | TNF-α | 190 | 226 | 124 | 181 | 22,570 | 7,827 | 621 | 2,004 | 72,283 | 58,958 | 3,818 | 6,673 |
|  | Average | 261 | 299 | 179 | 228 | 24,542 | 6,193 | 803 | 1,173 | 76,536 | 61,124 | 4,216 | 7,065 |

FIG. 5A

| | | Standard 2-Step | | | | 1 Step | | | | Mock ECL label | | | |
|---|---|---|---|---|---|---|---|---|---|---|---|---|---|
| LLOD (pg/ml) | Assay | TPA | BDEA | PIPES | 1.2 M TEA | TPA | BDEA | PIPES | 1.2 M TEA | TPA | BDEA | PIPES | 1.2 M TEA |
| | IFN-γ | 0.421 | 0.445 | 2.503 | 0.564 | 34.928 | 27.697 | 8.194 | 1.051 | 29.836 | 16.422 | 46.400 | 8.216 |
| | IL-1β | 0.044 | 0.147 | 0.271 | 0.045 | 0.104 | 0.210 | 9.751 | 0.154 | 1.975 | 1.493 | 1.346 | 0.641 |
| | IL-2 | 0.076 | 0.069 | 0.458 | 0.187 | 2.776 | 0.095 | 1.588 | 0.314 | 7.368 | 1.297 | 7.460 | 1.247 |
| | IL-4 | 0.013 | 0.011 | 0.030 | 0.013 | 1.139 | 0.328 | 0.160 | 0.032 | 0.872 | 0.307 | 0.648 | 0.216 |
| | IL-6 | 0.030 | 0.028 | 0.081 | 0.036 | 4.822 | 0.012 | 0.862 | 0.161 | 1.330 | 0.809 | 3.369 | 0.473 |
| | IL-8 | 0.036 | 0.042 | 0.196 | 0.076 | 5.404 | 3.074 | 0.933 | 1.324 | 3.552 | 0.871 | 2.078 | 0.351 |
| | IL-10 | 0.022 | 0.030 | 0.067 | 0.085 | 0.888 | 0.039 | 0.847 | 0.178 | 2.309 | 0.571 | 3.382 | 0.147 |
| | IL12p70 | 0.044 | 0.178 | 0.258 | 0.185 | 7.625 | 2.386 | 0.944 | 0.682 | 2.173 | 0.884 | 0.530 | 0.741 |
| | IL-13 | 0.129 | 0.052 | 0.418 | 0.157 | 2.441 | 4.626 | 2.140 | 1.077 | 5.407 | 1.434 | 3.164 | 1.033 |
| | TNF-α | 0.036 | 0.049 | 0.160 | 0.074 | 5.296 | 3.379 | 1.039 | 1.285 | 2.647 | 0.117 | 2.257 | 0.467 |
| | Average | 0.085 | 0.105 | 0.444 | 0.140 | 6.541 | 4.184 | 2.546 | 0.626 | 5.727 | 2.421 | 7.126 | 1.353 |

FIG. 5B

| | | Standard 2-Step | | | 1 Step | | | | Mock ECL label | | | |
|---|---|---|---|---|---|---|---|---|---|---|---|---|
| | Assay | TPA | BDEA | PIPES | 1.2 M TEA | TPA | BDEA | PIPES | 1.2 M TEA | TPA | BDEA | PIPES | 1.2 M TEA |
| Normalized ECL to BDEA A 2-Step Assay | IFN-γ | 1.00 | 1.01 | 0.18 | 0.50 | 2.44 | 1.15 | 0.18 | 0.54 | 8.23 | 6.80 | 0.45 | 1.20 |
| | IL-1β | 1.00 | 0.85 | 0.17 | 0.43 | 0.94 | 0.68 | 0.09 | 0.44 | 2.14 | 1.73 | 0.20 | 0.58 |
| | IL-2 | 1.00 | 0.97 | 0.22 | 0.37 | 0.83 | 0.75 | 0.13 | 0.40 | 1.90 | 1.70 | 0.26 | 0.49 |
| | IL-4 | 1.00 | 1.07 | 0.23 | 0.54 | 0.92 | 0.85 | 0.13 | 0.53 | 2.23 | 2.08 | 0.31 | 0.69 |
| | IL-6 | 1.00 | 0.90 | 0.18 | 0.47 | 0.86 | 0.72 | 0.09 | 0.46 | 1.81 | 1.55 | 0.23 | 0.53 |
| | IL-8 | 1.00 | 0.97 | 0.23 | 0.48 | 1.40 | 0.94 | 0.14 | 0.54 | 2.82 | 2.47 | 0.36 | 0.67 |
| | IL-10 | 1.00 | 1.06 | 0.19 | 0.49 | 1.11 | 0.88 | 0.11 | 0.53 | 2.48 | 2.20 | 0.27 | 0.64 |
| | IL12p70 | 1.00 | 1.00 | 0.17 | 0.47 | 1.11 | 0.85 | 0.09 | 0.49 | 2.60 | 2.34 | 0.25 | 0.64 |
| | IL-13 | 1.00 | 1.40 | 0.27 | 0.64 | 1.64 | 1.34 | 0.14 | 0.75 | 3.61 | 3.58 | 0.41 | 0.92 |
| | TNF-α | 1.00 | 0.90 | 0.21 | 0.49 | 1.84 | 0.99 | 0.13 | 0.57 | 4.12 | 3.53 | 0.37 | 0.82 |
| | Average | 1.00 | 1.01 | 0.20 | 0.49 | 1.31 | 0.91 | 0.12 | 0.53 | 3.20 | 2.79 | 0.31 | 0.72 |
| Normalized NSB ECL to BDEA A 2-Step Assay | IFN-γ | 1.00 | 1.52 | 0.76 | 1.15 | 75.99 | 16.44 | 2.11 | 1.75 | 295.82 | 238.62 | 13.63 | 28.20 |
| | IL-1β | 1.00 | 1.20 | 0.60 | 0.62 | 33.39 | 5.99 | 1.78 | 0.98 | 123.83 | 99.04 | 5.90 | 11.69 |
| | IL-2 | 1.00 | 0.98 | 0.85 | 0.65 | 50.42 | 10.11 | 2.40 | 1.56 | 188.30 | 145.98 | 12.35 | 16.92 |
| | IL-4 | 1.00 | 0.99 | 0.60 | 1.14 | 177.20 | 34.92 | 5.04 | 4.19 | 542.94 | 441.98 | 33.15 | 49.79 |
| | IL-6 | 1.00 | 0.91 | 0.51 | 1.01 | 151.49 | 29.90 | 4.05 | 4.70 | 475.62 | 386.98 | 21.19 | 44.72 |
| | IL-8 | 1.00 | 0.91 | 0.83 | 1.06 | 189.22 | 59.82 | 8.45 | 11.07 | 487.83 | 377.04 | 31.60 | 43.84 |
| | IL-10 | 1.00 | 1.12 | 0.66 | 0.94 | 111.05 | 24.84 | 3.53 | 5.67 | 352.53 | 266.91 | 21.04 | 31.84 |
| | IL12p70 | 1.00 | 1.42 | 0.66 | 1.05 | 105.52 | 27.61 | 2.49 | 6.25 | 286.05 | 236.35 | 14.08 | 27.34 |
| | IL-13 | 1.00 | 0.97 | 0.88 | 1.09 | 195.46 | 65.24 | 5.71 | 13.23 | 502.88 | 409.95 | 28.82 | 45.73 |
| | TNF-α | 1.00 | 1.19 | 0.65 | 0.95 | 118.58 | 41.12 | 3.26 | 10.53 | 379.77 | 309.78 | 20.06 | 35.06 |
| | Average | 1.00 | 1.12 | 0.68 | 0.97 | 120.83 | 31.60 | 3.68 | 5.99 | 363.56 | 291.26 | 20.18 | 33.49 |

| | | Standard 2-Step | | | | 1 Step | | | | Mock ECL label | | | |
|---|---|---|---|---|---|---|---|---|---|---|---|---|---|
| | Assay | TPA | BDEA | PIPES | 1.2 M TEA | TPA | BDEA | PIPES | 1.2 M TEA | TPA | BDEA | PIPES | 1.2 M TEA |
| S/B ratios | IFN-γ | 42 | 28 | 9 | 18 | 1.3 | 2.9 | 2.6 | 13 | 1.2 | 1.2 | 1.4 | 1.8 |
| | IL-1β | 116 | 82 | 33 | 81 | 3.3 | 13.1 | 5.7 | 52 | 2.0 | 2.0 | 4.0 | 5.7 |
| | IL-2 | 207 | 206 | 54 | 119 | 3.4 | 15.4 | 11.5 | 54 | 2.1 | 2.4 | 4.4 | 5.9 |
| | IL-4 | 451 | 489 | 172 | 211 | 2.3 | 11.0 | 11.8 | 57 | 1.9 | 2.1 | 4.2 | 6.2 |
| | IL-6 | 617 | 616 | 212 | 287 | 3.5 | 14.8 | 14.2 | 61 | 2.4 | 2.5 | 6.6 | 7.2 |
| | IL-8 | 260 | 275 | 92 | 118 | 1.9 | 4.1 | 5.7 | 13 | 1.6 | 1.7 | 2.9 | 4.0 |
| | IL-10 | 235 | 222 | 87 | 123 | 2.3 | 8.3 | 7.3 | 22 | 1.6 | 1.9 | 3.0 | 4.7 |
| | IL12p70 | 180 | 128 | 48 | 81 | 1.9 | 5.6 | 6.8 | 14 | 1.6 | 1.8 | 3.2 | 4.2 |
| | IL-13 | 203 | 293 | 62 | 118 | 1.7 | 4.2 | 4.9 | 12 | 1.5 | 1.8 | 2.9 | 4.1 |
| | TNF-α | 125 | 95 | 41 | 64 | 1.9 | 3.0 | 5.1 | 7 | 1.4 | 1.4 | 2.3 | 2.9 |
| | Average | 243 | 243 | 79 | 122 | 2.4 | 8.2 | 7.5 | 30 | 1.7 | 1.9 | 3.5 | 4.7 |
| S/N | IFN-γ | 610 | 540 | 147 | 1,622 | 21 | 11 | 33 | 269 | 43 | 92 | 16 | 59 |
| | IL-1β | 2,793 | 639 | 424 | 3,843 | 68 | 153 | 14 | 461 | 110 | 180 | 108 | 185 |
| | IL-2 | 4,780 | 5,011 | 665 | 1,527 | 48 | 840 | 219 | 686 | 73 | 989 | 46 | 309 |
| | IL-4 | 2,712 | 3,535 | 2,006 | 5,019 | 55 | 115 | 168 | 945 | 60 | 198 | 67 | 113 |
| | IL-6 | 7,691 | 8,933 | 11,440 | 30,353 | 43 | 742 | 181 | 1,005 | 169 | 644 | 46 | 441 |
| | IL-8 | 5,122 | 3,368 | 587 | 2,565 | 30 | 52 | 183 | 125 | 76 | 251 | 61 | 477 |
| | IL-10 | 5,223 | 2,559 | 2,536 | 1,175 | 42 | 1,539 | 92 | 278 | 80 | 160 | 47 | 4,181 |
| | IL12p70 | 2,903 | 685 | 413 | 641 | 24 | 59 | 95 | 209 | 78 | 184 | 105 | 162 |
| | IL-13 | 2,648 | 11,845 | 598 | 2,225 | 62 | 48 | 103 | 372 | 93 | 239 | 72 | 376 |
| | TNF-α | 3,560 | 2,516 | 440 | 1,078 | 16 | 24 | 65 | 58 | 89 | 694 | 63 | 168 |
| | Average | 3,804 | 3,963 | 1,925 | 5,007 | 41 | 359 | 115 | 439 | 87 | 361 | 63 | 647 |

| | | Standard 2-Step | | | | 1 Step | | | | 1 Step Non Wash | | |
|---|---|---|---|---|---|---|---|---|---|---|---|---|
| | Assay | TPA | BDEA | PIPES | 1.2 M TEA | TPA | BDEA | PIPES | 1.2 M TEA | TPA | BDEA | PIPES | 1.2 M TEA |
| ECL | IFN-γ | 10,414 | 10,527 | 1,703 | 5,214 | 25,457 | 11,949 | 1,379 | 5,864 | 27,487 | 17,362 | 308 | 8,826 |
| | IL-1β | 75,574 | 64,396 | 12,857 | 32,685 | 71,309 | 51,221 | 6,624 | 33,184 | 32,015 | 22,261 | 381 | 7,956 |
| | IL-2 | 90,868 | 68,271 | 19,863 | 33,834 | 75,501 | 88,319 | 12,133 | 38,617 | 74,043 | 99,159 | 858 | 49,102 |
| | IL-4 | 61,019 | 65,406 | 14,087 | 32,655 | 55,938 | 52,129 | 8,035 | 32,565 | 28,147 | 41,527 | 397 | 24,144 |
| | IL-6 | 98,891 | 88,481 | 17,475 | 46,365 | 84,829 | 71,017 | 9,258 | 45,882 | 43,250 | 56,936 | 481 | 32,736 |
| | IL-8 | 43,563 | 42,067 | 9,834 | 21,054 | 61,099 | 40,792 | 8,139 | 23,405 | 19,249 | 13,109 | 165 | 3,501 |
| | IL-10 | 53,009 | 56,204 | 10,255 | 26,201 | 58,624 | 46,839 | 5,805 | 28,357 | 26,124 | 39,616 | 203 | 20,592 |
| | IL12p70 | 43,580 | 43,700 | 7,624 | 20,426 | 48,428 | 37,091 | 3,974 | 21,504 | 11,941 | 33,970 | 168 | 18,667 |
| | IL-13 | 30,578 | 42,708 | 8,182 | 19,438 | 50,140 | 40,839 | 4,181 | 22,929 | 27,354 | 68,978 | 478 | 39,878 |
| | TNF-α | 23,705 | 21,397 | 5,066 | 11,532 | 43,698 | 23,474 | 3,192 | 13,604 | 10,919 | 14,293 | 134 | 4,099 |
| | Average | 53,120 | 52,416 | 10,705 | 24,920 | 57,502 | 46,367 | 6,073 | 26,371 | 30,053 | 40,721 | 369 | 20,750 |
| NSB ECL | IFN-γ | 249 | 379 | 190 | 287 | 18,921 | 4,082 | 524 | 437 | 16,567 | 6,131 | 153 | 448 |
| | IL-1β | 652 | 784 | 380 | 402 | 21,780 | 3,910 | 1,158 | 637 | 17,386 | 8,586 | 308 | 1,048 |
| | IL-2 | 438 | 429 | 373 | 284 | 22,100 | 4,431 | 1,053 | 684 | 15,819 | 6,280 | 153 | 524 |
| | IL-4 | 135 | 134 | 82 | 155 | 23,981 | 4,726 | 683 | 568 | 13,204 | 6,505 | 100 | 544 |
| | IL-6 | 160 | 145 | 82 | 162 | 24,289 | 4,794 | 650 | 754 | 14,356 | 6,462 | 99 | 742 |
| | IL-8 | 168 | 153 | 108 | 178 | 31,727 | 10,030 | 1,082 | 1,858 | 11,134 | 7,194 | 138 | 821 |
| | IL-10 | 228 | 254 | 154 | 212 | 25,097 | 5,614 | 787 | 1,282 | 9,868 | 8,341 | 104 | 709 |
| | IL12p70 | 242 | 342 | 159 | 253 | 25,501 | 6,673 | 602 | 1,511 | 3,309 | 6,773 | 123 | 1,457 |
| | IL-13 | 151 | 146 | 132 | 164 | 29,449 | 9,829 | 861 | 1,993 | 7,165 | 8,861 | 124 | 1,375 |
| | TNF-α | 190 | 226 | 124 | 181 | 22,570 | 7,827 | 621 | 2,004 | 3,697 | 8,139 | 102 | 1,558 |
| | Average | 261 | 299 | 178 | 228 | 24,542 | 6,193 | 803 | 1,173 | 11,260 | 7,127 | 140 | 923 |

FIG. 6A

| | | Standard 2-Step | | | 1 Step | | | | 1 Step Non Wash | | | |
|---|---|---|---|---|---|---|---|---|---|---|---|---|
| | Assay | TPA | BDEA | PIPES | 1.2 M TEA | TPA | BDEA | PIPES | 1.2 M TEA | TPA | BDEA | PIPES | 1.2 M TEA |
| LLOD (pg/ml) | IFN-γ | 0.421 | 0.445 | 2.503 | 0.564 | 34.928 | 27.697 | 8.184 | 1.051 | 6.120 | 8.085 | 9.977 | 0.571 |
| | IL-1β | 0.044 | 0.147 | 0.271 | 0.045 | 0.104 | 0.210 | 8.751 | 0.154 | 1.454 | 0.569 | 30.265 | 2.684 |
| | IL-2 | 0.078 | 0.069 | 0.458 | 0.187 | 2.776 | 0.095 | 1.588 | 0.314 | 0.770 | 0.044 | 3.061 | 0.723 |
| | IL-4 | 0.013 | 0.011 | 0.030 | 0.013 | 1.139 | 0.326 | 0.160 | 0.032 | 3.641 | 0.818 | 1.248 | 0.097 |
| | IL-6 | 0.030 | 0.026 | 0.081 | 0.036 | 4.822 | 0.012 | 0.862 | 0.161 | 4.341 | 0.883 | 4.573 | 0.272 |
| | IL-8 | 0.038 | 0.042 | 0.198 | 0.076 | 5.404 | 3.074 | 0.933 | 1.324 | 50.301 | 15.962 | 125.791 | 0.837 |
| | IL-10 | 0.022 | 0.030 | 0.067 | 0.065 | 0.888 | 0.039 | 0.847 | 0.178 | 5.897 | 0.798 | 10.920 | 0.281 |
| | IL12p70 | 0.044 | 0.176 | 0.268 | 0.185 | 7.625 | 2.366 | 0.844 | 0.682 | 0.214 | 0.348 | 51.369 | 0.385 |
| | IL-13 | 0.129 | 0.052 | 0.418 | 0.157 | 2.441 | 4.626 | 2.140 | 1.077 | 14.431 | 3.265 | 8.751 | 3.185 |
| | TNF-α | 0.036 | 0.049 | 0.160 | 0.074 | 5.286 | 3.379 | 1.039 | 1.285 | 0.532 | 8.364 | 230.860 | 1.124 |
| | Average | 0.085 | 0.105 | 0.444 | 0.140 | 6.541 | 4.184 | 2.546 | 0.626 | 8.770 | 3.916 | 47.679 | 1.016 |

FIG. 6B

| | Standard 2-Step | | | | 1 Step | | | | 1 Step Non Wash | | | |
|---|---|---|---|---|---|---|---|---|---|---|---|---|
| Assay | TPA | BDEA | PIPES | 1.2 M TEA | TPA | BDEA | PIPES | 1.2 M TEA | TPA | BDEA | PIPES | 1.2 M TEA |
| IFN-γ | 1.00 | 1.01 | 0.16 | 0.50 | 2.44 | 1.15 | 0.13 | 0.54 | 2.64 | 1.67 | 0.03 | 0.66 |
| IL-1β | 1.00 | 0.85 | 0.17 | 0.43 | 0.94 | 0.68 | 0.09 | 0.44 | 0.42 | 0.29 | 0.01 | 0.11 |
| IL-2 | 1.00 | 0.97 | 0.22 | 0.37 | 0.83 | 0.75 | 0.13 | 0.40 | 0.81 | 1.09 | 0.01 | 0.54 |
| IL-4 | 1.00 | 1.07 | 0.23 | 0.54 | 0.92 | 0.85 | 0.13 | 0.53 | 0.46 | 0.68 | 0.01 | 0.40 |
| IL-6 | 1.00 | 0.90 | 0.18 | 0.47 | 0.86 | 0.72 | 0.09 | 0.46 | 0.44 | 0.56 | 0.00 | 0.33 |
| IL-8 | 1.00 | 0.97 | 0.23 | 0.48 | 1.40 | 0.94 | 0.14 | 0.54 | 0.44 | 0.30 | 0.00 | 0.08 |
| IL-10 | 1.00 | 1.06 | 0.19 | 0.49 | 1.11 | 0.88 | 0.11 | 0.53 | 0.49 | 0.75 | 0.00 | 0.39 |
| IL12p70 | 1.00 | 1.00 | 0.17 | 0.47 | 1.11 | 0.85 | 0.09 | 0.49 | 0.27 | 0.78 | 0.00 | 0.43 |
| IL-13 | 1.00 | 1.40 | 0.27 | 0.64 | 1.64 | 1.34 | 0.14 | 0.75 | 0.89 | 2.26 | 0.02 | 1.30 |
| TNF-α | 1.00 | 0.80 | 0.21 | 0.49 | 1.84 | 0.99 | 0.13 | 0.57 | 0.46 | 0.60 | 0.01 | 0.17 |
| Average | 1.00 | 1.01 | 0.20 | 0.49 | 1.31 | 0.91 | 0.12 | 0.53 | 0.73 | 0.90 | 0.01 | 0.44 |
| IFN-γ | 1.00 | 1.52 | 0.76 | 1.15 | 75.99 | 16.44 | 2.11 | 1.75 | 66.54 | 24.62 | 0.62 | 1.80 |
| IL-1β | 1.00 | 1.20 | 0.60 | 0.62 | 33.39 | 5.99 | 1.78 | 0.98 | 26.62 | 13.16 | 0.47 | 1.61 |
| IL-2 | 1.00 | 0.98 | 0.85 | 0.65 | 50.42 | 10.11 | 2.40 | 1.56 | 36.09 | 14.33 | 0.35 | 1.19 |
| IL-4 | 1.00 | 0.99 | 0.60 | 1.14 | 177.20 | 34.92 | 5.04 | 4.19 | 97.56 | 48.07 | 0.74 | 4.02 |
| IL-6 | 1.00 | 0.91 | 0.51 | 1.01 | 151.49 | 29.90 | 4.06 | 4.70 | 89.54 | 40.30 | 0.62 | 4.63 |
| IL-8 | 1.00 | 0.91 | 0.63 | 1.08 | 189.22 | 59.82 | 6.45 | 11.07 | 66.41 | 42.91 | 0.81 | 4.90 |
| IL-10 | 1.00 | 1.12 | 0.66 | 0.94 | 111.05 | 24.84 | 3.53 | 5.67 | 44.19 | 28.06 | 0.46 | 3.14 |
| IL12p70 | 1.00 | 1.42 | 0.88 | 1.05 | 105.52 | 27.61 | 2.49 | 6.25 | 13.69 | 28.02 | 0.51 | 6.03 |
| IL-13 | 1.00 | 0.97 | 0.88 | 1.09 | 195.46 | 65.24 | 5.71 | 13.23 | 47.56 | 58.81 | 0.83 | 9.12 |
| TNF-α | 1.00 | 1.19 | 0.65 | 0.95 | 118.58 | 41.12 | 3.26 | 10.53 | 19.42 | 42.76 | 0.54 | 8.18 |
| Average | 1.00 | 1.12 | 0.68 | 0.97 | 120.83 | 31.60 | 3.68 | 5.99 | 50.76 | 34.10 | 0.59 | 4.46 |

Normalized Mid-Cal ECL to 2-Step Assay (Cal 3) — top block
Normalized NSB ECL to 2-Step Assay (Cal 3) — bottom block

FIG. 6C

| ID.Name | Sample |
|---|---|
| P1 | Matched Human Plasma #1 |
| P2 | Matched Human Plasma #2 |
| P3 | Matched Human Plasma #3 |
| P4 | Matched Human Plasma #4 |
| S1 | Matched Human Serum #1 |
| S2 | Matched Human Serum #2 |
| S3 | Matched Human Serum #3 |
| S4 | Matched Human Serum #4 |
| FBS1 | Fetal Bovine Serum #1 |
| FBS2 | Fetal Bovine Serum #2 |
| FBS3 | Fetal Bovine Serum #3 |
| BS4 | Bovine serum #1 |
| BS5 | Bovine serum #2 |
| CS1 | Chicken serum #1 |
| CS2 | Chicken serum #2 |
| CS3 | Chicken serum #3 |
| D43 | Diluent 43 |
| D2 | Diluent 2 |
| DMEM | DMEM (1X)+GlutaMAX |
| FBS | FBS |
|  | 100x Penicillin Streptomycin |
| D3 | Diluent 3 |

FIG. 7A

| Compound |
|---|
| Acetamenophene |
| Ibuprofen |
| Naproxen |
| Ascorbic acid |
| Salicylic acid |
| Tolbutamine |
| EtOH |

| Read Buffer vol | Spike & [ ] | Sample Matrix | ECL Generation D3+STAG | ECL Generation H2O+STAG | %CV D3+STAG | %CV H2O+STAG |
|---|---|---|---|---|---|---|
| 150 uL | None | Hu Plasma 1 | 235 | N/A | 5.9% | N/A |
| | | Hu Plasma 2 | 231 | N/A | 11.0% | N/A |
| | | Hu Plasma 3 | 212 | N/A | 5.4% | N/A |
| | | Hu Plasma 4 | 234 | N/A | 9.3% | N/A |
| | | Hu Serum 1 | 237 | N/A | 2.8% | N/A |
| | | Hu Serum 2 | 245 | N/A | 2.2% | N/A |
| | | Hu Serum 3 | 241 | N/A | 5.8% | N/A |
| | | Hu Serum 4 | 262 | N/A | 8.4% | N/A |
| | | BS3 | 208 | N/A | 5.0% | N/A |
| | | BS5 | 207 | N/A | 5.3% | N/A |
| | | BS5 | 216 | N/A | 2.8% | N/A |
| | | BS4 | 280 | N/A | 4.1% | N/A |
| | | BS5 | 259 | N/A | 6.7% | N/A |
| | | CS1 | 190 | N/A | 6.1% | N/A |
| | | CS2 | 193 | N/A | 2.1% | N/A |
| | | CS3 | 183 | N/A | 4.3% | N/A |
| | | D2 | 222 | N/A | 7.4% | N/A |
| | | D3 | 229 | N/A | 8.4% | N/A |
| | | D43 | 205 | N/A | 7.2% | N/A |
| | | DMEM | 166 | N/A | 6.8% | N/A |
| | | H2O | N/A | 167 | N/A | 14.0% |

FIG. 10B

| Read Buffer vol | Spike & [ ] | Sample Matrix | ECL generation vs No Matrix Control D3+STAG | ECL generation vs No Matrix Control H2O+STAG | Absolute Error D3+STAG | Absolute Error H2O+STAG |
|---|---|---|---|---|---|---|
| 150 uL | None | Hu Plasma 1 | 141% | N/A | 21.4% | N/A |
| | | Hu Plasma 2 | 139% | N/A | 24.6% | N/A |
| | | Hu Plasma 3 | 127% | N/A | 19.0% | N/A |
| | | Hu Plasma 4 | 140% | N/A | 23.5% | N/A |
| | | Hu Serum 1 | 142% | N/A | 20.2% | N/A |
| | | Hu Serum 2 | 147% | N/A | 20.8% | N/A |
| | | Hu Serum 3 | 145% | N/A | 21.9% | N/A |
| | | Hu Serum 4 | 157% | N/A | 25.7% | N/A |
| | | BS3 | 125% | N/A | 18.5% | N/A |
| | | BS5 | 124% | N/A | 18.6% | N/A |
| | | BS5 | 130% | N/A | 18.5% | N/A |
| | | BS4 | 168% | N/A | 24.4% | N/A |
| | | BS5 | 155% | N/A | 24.1% | N/A |
| | | CS1 | 114% | N/A | 17.3% | N/A |
| | | CS2 | 116% | N/A | 16.4% | N/A |
| | | CS3 | 110% | N/A | 16.0% | N/A |
| | | D2 | 133% | N/A | 21.0% | N/A |
| | | D3 | 137% | N/A | 22.4% | N/A |
| | | D43 | 123% | N/A | 19.3% | N/A |
| | | DMEM | 100% | N/A | 15.5% | N/A |
| | | H2O | N/A | 100% | N/A | 19.8% |

| | D3+STAG |
|---|---|
| Average % | 135% |
| STDEV of % CL | 15% |
| Max | 168% |
| Min | 110% |

BTI ECL values

| Amine | | TX100 | PEG18TDE |
|---|---|---|---|
| PIPES | | 164192 | 1796 |
| DBA-BS | | 72635 | 13287 |
| DEAE | | 94857 | 14972 |
| tBDEA | | 21802 | 15089 |
| BEA-BS | | 77341 | 15385 |
| MDEA | | 68779 | 33035 |
| TEA | | 42711 | 49550 |
| DEA-BS | | 68844 | 53359 |
| DEA-PS | | 60096 | 61135 |
| DBA-PS | | 87009 | 71404 |
| DBAE | | 96864 | 78598 |
| EDEA | | 122422 | 117014 |
| BDEA | | 148197 | 154964 |
| TBA | | 190813 | 201228 |

FT ECL values

| Amine | | TX100 | PEG18TDE |
|---|---|---|---|
| PIPES | | 38699 | 248 |
| tBDEA | | 3288 | 2359 |
| TEA | | 4238 | 4701 |
| MDEA | | 8346 | 5473 |
| BEA-BS | | 28776 | 6930 |
| DEAE | | 54448 | 9202 |
| DEA-PS | | 9516 | 12407 |
| DEA-BS | | 14328 | 14333 |
| DBA-BS | | 164340 | 22076 |
| DBAE | | 36114 | 24713 |
| BDEA | | 43948 | 41687 |
| EDEA | | 46940 | 43538 |
| DBA-PS | | 120247 | 59261 |
| TBA | | 227059 | 231629 |

| Amine | ECL ratio (PEG18TDE vs TX100) | | Amine | pKa |
|---|---|---|---|---|
| | BTI TX100 vs PEG18 | FT TX100 vs PEG18 | | |
| TEA | 0.9 | 0.9 | TEA | 7.73 |
| TBA | 0.9 | 1.0 | TBA | 10.89 |
| BDEA | 1.0 | 1.1 | BDEA | 8.90 |
| DEA-PS | 1.0 | 0.8 | DEA-PS | ? |
| EDEA | 1.0 | 1.1 | EDEA | 8.80 |
| DBA-PS | 1.2 | 2.0 | DBA-PS | ? |
| DBAE | 1.2 | 1.5 | DBAE | 9.83 |
| DEA-BS | 1.3 | 1.0 | DEA-BS | ? |
| tBDEA | 1.4 | 1.4 | tBDEA | 9.03 |
| MDEA | 2.1 | 1.5 | MDEA | 8.54 |
| BEA-BS | 5.0 | 4.2 | BEA-BS | ? |
| DBA-BS | 5.5 | 7.4 | DBA-BS | ? |
| DEAE | 6.3 | 5.9 | DEAE | 9.73 |
| PIPES | 102.4 | 156.3 | PIPES | 6.76 |

FIG. 13B

COMPOSITIONS AND METHODS FOR ASSAY MEASUREMENTS

FIELD OF THE INVENTION

The invention relates to compositions comprising an electrochemiluminescence (ECL) co-reactant. In embodiments, the composition further comprises an ionic component, a surfactant, or combination thereof. In embodiments, the ECL co-reactant is triethanolamine (TEA), tert-butyldiethanolamine (tBDEA), methyldiethanolamine (MDEA), 3-[Bis-(2-hydroxy-ethyl)-amino]-propane-1-sulfonic acid (DEA-PS), or a combination thereof. Methods of using the compositions and kits comprising the compositions are also provided.

BACKGROUND

A number of commercially available instruments use electrochemiluminescence (ECL) for analytical measurements. Compounds that interact with the ECL label and generate ECL are referred to as ECL coreactants. Commonly used coreactants include tertiary amines (see, e.g., U.S. Pat. No. 5,846,485), oxalate, and persulfate for ECL from $Ru(Bpy)_3^{+2}$, and hydrogen peroxide for ECL from luminol (see, e.g., U.S. Pat. No. 5,240,863). The light generated by ECL labels can be used as a reporter signal in diagnostic procedures (see, e.g., U.S. Pat. No. 5,238,808). For instance, an ECL label can be covalently coupled to a detection reagent, and the participation of the detection reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). ECL-based assays are further described in U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; 5,589,136; and 6,919,173, and International Publication Nos. WO99/63347; WO00/03233; WO99/58962; WO99/32662; WO99/14599; WO98/12539; WO97/36931 and WO98/57154.

Commercially available ECL instruments have become widely used because of their sensitivity, dynamic range, precision, and tolerance of complex sample matrices, among others. Several types of commercial instrumentation are available for performing ECL-based measurements (see, e.g., Debad, J. D., et al., 2004. Clinical and Biological Applications of ECL, in: Electrogenerated Chemiluminescence. Marcel Dekker, pp. 43-78). ECL instruments are further described, e.g., in U.S. Pat. Nos. 5,935,779 and 5,993,740 (bead-based ECL assays); U.S. Pat. Nos. 6,140,045; 6,066,448; 6,090,545; 6,207,369 and International Publication No. WO98/12539 (ECL assays using immobilized binding reagents); U.S. Pat. Nos. 6,977,722 and 7,842,246 (multi-well plates having integrated electrodes for ECL assays); and US Publication Nos. 2012/0190589 and US 2012/0178091 (cartridge-based ECL assays).

The ECL coreactant tripropylamine (TPA) is typically used in ECL-based assays.

SUMMARY OF THE INVENTION

In embodiments, the invention provides a composition comprising: (a) triethanolamine (TEA); and (b) an ionic component; wherein the composition has a pH of about 7.0 to about 8.0, and wherein the composition is substantially free of an additional pH buffering component. In embodiments, the composition further comprises a surfactant.

In embodiments, the invention provides a composition comprising: (a) triethanolamine (TEA); (b) an ionic component; and (c) an ECL-labeled component; wherein the composition has a pH of about 7.0 to about 8.0, and wherein the composition is substantially free of an additional pH buffering component.

In embodiments, the invention provides a composition comprising (a) TEA, (b) an ionic component; and (c) optionally, one or both of an ECL-labeled component and a surfactant, wherein the composition has a pH of about 7.0 to about 8.0, and optionally wherein the composition is substantially free of an additional pH buffering component.

In embodiments, the invention provides a composition comprising: (a) about 1000 mM to about 6500 mM of triethanolamine (TEA); and (b) about 500 mM to about 2000 mM of an ionic component, wherein the composition has a pH of about 7.0 to about 8.0. In embodiments, the composition further comprises a surfactant. In embodiments, the composition further comprises an ECL-labeled component.

In embodiments, the invention provides a composition comprising: (a) triethanolamine (TEA); (b) an ionic component; (c) an alkyl ether-polyethylene glycol (PEG); wherein the composition has a pH of about 7.0 to about 8.0. In embodiments, the composition further comprises an ECL-labeled component.

In embodiments, the invention provides a composition comprising: (a) an electrochemiluminescence (ECL) co-reactant selected from N-tert-butyldiethanolamine (tBDEA), methyldiethanolamine (MDEA), 3-[Bis-(2-hydroxy-ethyl)-amino]-propane-1-sulfonic acid (DEA-PS), and combination thereof; (b) an ionic component; and (c) a surfactant; wherein the composition has a pH of about 7.0 to about 8.0. In embodiments, the ECL coreactant is tBDEA. In embodiments, the ECL coreactant is MDEA. In embodiments, the ECL coreactant is DEA-PS. the composition further comprises an ECL-labeled component.

In embodiments, the invention provides a method for generating electrochemiluminescence (ECL), comprising: (a) contacting an electrode with (i) the composition provided herein or a TEA composition comprising TEA, an ionic component, and optionally a surfactant; and (ii) an ECL label; and (b) applying a voltage to the electrode, thereby generating ECL.

In embodiments, the invention provides a method for detecting a binding complex, comprising: (a) contacting a liquid sample with a surface comprising the composition provided herein or a TEA composition comprising TEA, an ionic component, and optionally a surfactant, wherein the liquid sample comprises an ECL-labeled component; or wherein the liquid sample comprises a binding partner of an ECL-labeled component, and the method further comprises contacting the surface with the ECL-labeled component, thereby forming a binding complex on the surface that comprises the ECL-labeled component; (b) applying a voltage to the surface to generate ECL; and (c) detecting the generated ECL, thereby detecting the binding complex.

In embodiments, the invention provides a method for detecting a binding complex, comprising: (a) contacting a liquid sample with a surface comprising an ECL-labeled component and the composition provided herein or a TEA composition comprising TEA, an ionic component, and optionally a surfactant, wherein the liquid sample comprises a binding partner of an ECL-labeled component, thereby forming a binding complex on the surface that comprises the ECL-labeled component; (b) applying a voltage to the surface to generate ECL; and (c) detecting the generated ECL, thereby detecting the binding complex.

In embodiments, the invention provides a method for detecting a binding complex, comprising: (a) forming a binding complex on a surface, and wherein the binding complex comprises an ECL-labeled component; (b) contacting the binding complex with the composition provided herein or a TEA composition comprising TEA, an ionic component, and optionally a surfactant; (c) applying a voltage to the surface to generate ECL; and (d) detecting the generated ECL, thereby detecting the binding complex.

In embodiments, the invention provides a method for detecting a binding complex, comprising: (a) forming a binding complex on a surface, wherein the surface optionally comprises an electrode, and wherein the binding complex comprises a binding reagent immobilized on the surface and a detection reagent comprising an electrochemiluminescence (ECL) label; (b) contacting the binding complex with the composition provided herein or a TEA composition comprising TEA, an ionic component, and optionally a surfactant; (c) applying a voltage to the surface to generate ECL; and (d) detecting the generated ECL, thereby detecting the binding complex.

In embodiments, the invention provides a method for detecting an analyte of interest in a sample, comprising: (a) contacting the sample with: (i) a surface comprising a binding reagent, wherein the binding reagent specifically binds to the analyte; and (ii) a detection reagent that specifically binds to the analyte, wherein the detection reagent comprises an electrochemiluminescence (ECL) label, thereby forming a binding complex on the surface comprising the binding reagent, the analyte, and the detection reagent; (b) contacting the binding complex on the surface with the composition provided herein or a TEA composition comprising TEA, an ionic component, and optionally a surfactant; (c) applying a voltage to the surface to generate ECL; and (d) detecting the generated ECL, thereby detecting the analyte.

In embodiments, the invention provides a method for detecting a binding complex, comprising: (a) forming an assay mixture by combining a sample with: (i) the composition provided herein or a TEA composition comprising TEA, an ionic component, and optionally a surfactant; and (ii) a detection mixture comprising at least two copies of a detection reagent, wherein each copy of the detection reagent comprises an ECL label; (b) contacting the assay mixture with a binding reagent immobilized on a surface, wherein the surface optionally comprises an electrode, under conditions wherein (I) a binding complex is formed on the surface, the binding complex comprising the binding reagent and a first copy of the detection reagent; and (II) a second copy of the detection reagent remains in solution; (c) applying a voltage to the surface to generate ECL; and (d) detecting the generated ECL, thereby detecting the binding complex.

In embodiments, the invention provides a method for detecting a binding complex, comprising: (a) incubating an assay mixture comprising (i) a binding reagent immobilized on a surface, wherein the surface optionally comprises an electrode; and (ii) a detection mixture comprising at least two copies of a detection reagent, wherein each copy of the detection reagent comprises an electrochemiluminescence (ECL) label; under conditions wherein (i) a binding complex is formed on the surface, the binding complex comprising the binding reagent and a first copy of the detection reagent; and (ii) a second copy of the detection reagent remains in solution; (b) contacting the binding complex with the composition provided herein or a TEA composition comprising TEA, an ionic component, and optionally a surfactant; (c) applying a voltage to the surface to generate ECL; and (d) detecting the generated ECL, thereby detecting the binding complex.

In embodiments, the invention provides a method for detecting a binding complex, comprising: (a) incubating an assay mixture comprising (i) a binding reagent immobilized on a surface, wherein the surface optionally comprises an electrode; (ii) a detection mixture comprising at least two copies of a detection reagent, wherein each copy of the detection reagent comprises an electrochemiluminescence (ECL) label; and (iii) the composition provided herein or a TEA composition comprising TEA, an ionic component, and optionally a surfactant; under conditions wherein (i) a binding complex is formed on the surface, the binding complex comprising the binding reagent and a first copy of the detection reagent; and (ii) a second copy of the detection reagent remains in solution; (b) applying a voltage to the surface to generate ECL; and (c) detecting the generated ECL, thereby detecting the binding complex.

In embodiments, the invention provides a method for generating electrochemiluminescence (ECL), comprising: (a) contacting an electrode with (i) the composition provided herein; and (ii) an ECL label; (b) applying a voltage to the electrode; and (c) generating ECL.

In embodiments, the invention provides a method for quantifying the amount of an electrochemiluminescence (ECL) label in a sample, comprising: (a) contacting an electrode with (i) the composition provided herein; and (ii) the sample comprising the ECL label; (b) applying a voltage to the electrode; (c) generating ECL; (d) measuring the ECL; and (e) quantifying the amount of the ECL label from the measured ECL.

In embodiments, the invention provides a method for producing a composition, comprising combining: (a) triethanolamine (TEA); (b) an ionic component; and (c) a surfactant, wherein the method does not comprise adding an additional pH buffering component.

In embodiments, the invention provides an assay module comprising a TEA composition in dry form, wherein the TEA composition comprises TEA, an ionic component, and optionally a surfactant.

In embodiments, the invention provides a kit comprising (a) the composition provided herein or a TEA composition comprising TEA, an ionic component, and optionally a surfactant; and (b) optionally a surface comprising an electrode, optionally wherein the TEA composition does not comprise an additional pH buffering component.

In embodiments, the invention provides a kit comprising, in one or more containers, vials, or compartments: (a) triethanolamine (TEA); (b) an ionic component; and (c) a surfactant, wherein the kit does not comprise an additional pH buffering component.

BRIEF DESCRIPTION OF THE DRAWINGS

The following drawings form part of the present specification and are included to further demonstrate exemplary embodiments of certain aspects of the present invention.

FIGS. 1A and 1B relate to Example 1 and show the results of an embodiment of an ECL-based assay. A panel of ECL coreactants combined with one of two surfactants was tested for ECL generation and ability to discriminate between surface-bound ("BTI") and free (in solution; "FT") ECL labels in a solid-surface ECL assay. FIG. 1A shows the ECL signal measured with BTI, FT, and background signal ("D100") with ECL read buffer only (no label). FIG. 1B shows the ratio of ECL signal from bound label to ECL signal from free label ("BTI/FT"), and the signal-to-background ratio ("S/B").

FIG. 2A shows a plot of the ECL generated from BTI and FT, and the BTI/FT ratio with varying concentration of TEA. FIG. 2B shows the measured ECL signals from BTI, FT, and background (D100) with varying concentrations of TEA. FIG. 2C shows the BTI/FT ratio, S/B ratio, and percent ECL generation compared with PIPES ECL read buffer.

FIG. 3A shows the change in ECL signal as a function of PIPES concentration. FIG. 3B shows the change in ECL signal as a function of PIPES or TEA concentration.

FIG. 4A illustrates a "standard" 2-step washed assay, wherein a capture antibody ("cAb"; binding reagent) immobilized on a surface is contacted with a mixture of analytes, one of which binds specifically to the capture antibody, and the surface is then washed, resulting in the analyte captured on the surface. A mixture of detection antibodies ("dAb"; detection reagent), each containing an ECL label and one of which binds specifically to the analyte, is then added to the surface, and the surface is then washed, resulting in a binding complex comprising the cAb, analyte, and dAb. ECL read buffer is then added to the surface, and the generated ECL is then read by an ECL reader instrument.

FIG. 4B illustrates a "1-step" assay, wherein a capture antibody on a surface is contacted with an analyte mix, and the surface is then washed as in FIG. 4A. The detection antibody mix is then added, followed by the ECL read buffer without washing in between adding the detection antibody mix and the ECL read buffer. The generated ECL is then read by an ECL reader instrument.

FIG. 4C illustrates a "1-step non-wash" assay, wherein a capture antibody on a surface is contacted with: an analyte mix and detection antibody mix, followed by the ECL read buffer without washing in between any of the steps. The generated ECL is then read by an ECL reader instrument.

FIG. 4D illustrates a "mock ECL label" assay, wherein a capture antibody on a surface is contacted with an analyte mix, the surface is washed, and a detection antibody mix is added, the surface is optionally washed again, resulting in a binding complex as in FIG. 4A. The ECL read buffer is then added to the surface along with a detection antibody that comprises an ECL label and that does not bind to any component of the binding complex on the surface, which serves as a proxy for "free" ECL label in solution. The generated ECL is then read by an ECL reader instrument.

FIG. 4E illustrates a multiplexed version of the "standard" 2-step washed assay, wherein one or more surfaces comprises a plurality of binding domains, each binding domain comprising a capture antibody that can bind to an analyte in the analyte mix. The surface(s) comprising the binding domains is washed after adding the analyte mix, resulting in a plurality of analytes captured on the binding domains. A mixture of detection antibodies, each containing an ECL label and capable of binding to an analyte in the analyte mix, is then added to the surface(s), and the surface is then washed, resulting in a plurality of binding complexes, each binding complex comprising a cAb, analyte, and dAb. ECL read buffer is then added to the surface, and the generated ECL is read by an ECL instrument.

FIG. 4F illustrates a multiplexed version of the "1-step" assay, wherein one or more surfaces comprises a plurality of binding domains, each binding domain comprising a capture antibody that can bind to an analyte in the analyte mix. The surface(s) comprising the binding domains is washed after adding the analyte mix as in FIG. 4E. The detection antibody mix is added to form a plurality of binding complexes, and ECL read buffer is then added without washing in between adding the detection antibody mix and the ECL read buffer. The generated ECL is then read by an ECL reader instrument.

FIG. 4G illustrates a multiplexed version of the "1-step non-wash" assay, wherein one or more surfaces comprises a plurality of binding domains, each binding domain comprising a capture antibody that can bind to an analyte in the analyte mix. The surface(s) comprising the binding domains is contacted with an analyte mix and detection antibody mix to form a plurality of binding complexes, then ECL read buffer is added without washing in between any of the steps. The generated ECL is then read by an ECL reader instrument.

FIG. 4H illustrates a multiplexed version of the "mock ECL label" assay, wherein one or more surfaces comprises a plurality of binding domains, each binding domain comprising a capture antibody that can bind to an analyte in the analyte mix. The surface(s) comprising the binding reagents is contacted with an analyte mix, the surface is washed, a detection antibody mix is added, and the surface is optionally washed again, resulting in a plurality of binding complexes as in FIG. 4E. The ECL read buffer is then added to the surface along with a detection antibody that comprises an ECL label and that does not bind to any component of the binding complex on the surface, which serves as a proxy for "free" ECL label in solution. The generated ECL is then read by an ECL reader instrument.

FIGS. 5A-5D relate to Example 5A and show the results of an embodiment of an ECL-based assay. FIG. 5A shows the results of specific ECL signal and non-specific binding (NSB) from three different multiplexed assay formats (shown in FIGS. 4E, 4F, and 4H) with BDEA, PIPES, and TEA read buffers. FIG. 5B shows the lowest limit of detection (LLOD) of the assays in FIG. 5A. FIG. 5C shows a relative comparison of the ECL and NSB results from FIG. 5A. FIG. 5D shows the comparison of signal to background (S/B) and signal to noise (S/N) ratio across all ECL read buffers and assay formats.

FIGS. 6A-6C relate to Example 5B and show the results of an embodiment of an ECL-based assay. FIG. 6A shows the results of specific ECL signal and non-specific binding (NSB) from three different multiplexed assay formats (shown in FIGS. 4E, 4F, and 4G) with BDEA, PIPES, and TEA read buffers. FIG. 6B shows the lowest limit of detection (LLOD) of the assays in FIG. 6A. FIG. 6C shows a relative comparison of the ECL and NSB results from FIG. 6A.

FIGS. 7A-11B relate to Example 6 and show the results of an embodiment of an ECL-based assay.

FIG. 7A shows a list of sample matrices tested with TEA read buffer in a 1-step non-wash ECL assay. FIG. 7B shows a list of interferents added to the sample matrices in FIG. 7A, to be tested with TEA read buffer in a 1-step non-wash ECL assay.

FIG. 8A shows the results of ECL signal generated from TEA read buffer with bound ECL label ("Bound") and free ECL label ("Free"), with different sample matrices mixed with diluent. "H2O" indicates signal from a control with water instead of a sample matrix prior to TEA read buffer. The column headers with "Free" indicates 6 nM of free ECL label in diluent.

FIG. 8B shows the results of FIG. 8A normalized to ECL signal generated from an assay in which sample matrices were not added.

FIG. 9A shows the results of ECL signal generated from TEA read buffer with bound and free ECL label with different interferents in different sample matrices. FIG. 9B shows the results of FIG. 9A normalized to ECL signal generated from an assay in which sample matrices and interferents were not added.

FIG. 10A shows the results of ECL signal generated from TEA read buffer with free ECL label ("D3+STAG") in different sample matrices. The column headers with "Free" indicates 240 nM of free ECL label in diluent. FIG. 10B shows the results of FIG. 10A normalized to ECL signal generated from an assay in which sample matrices were not added.

FIG. 11A shows results of ECL signal generated from TEA read buffer with 240 nM of free ECL with different interferents in different sample matrices. FIG. 11B shows the results of FIG. 11A normalized to ECL signal generated from an assay in which sample matrices and interferents were not added.

FIG. 12 relates to Example 7 and shows the results of an embodiment of an ECL-based assay. Combinations of ECL coreactants described in Example 1 were tested in an ECL-based assay. The top-right side of the chart in FIG. 12 shows the ECL signal generated from BTI, while the bottom-left side of the chart in FIG. 12 shows the ECL signal ratio of the mixed ECL coreactants to the sum of signal generated by the individual ECL coreactants.

FIGS. 13A and 13B relate to Example 8 and show the results of an embodiment of an ECL-based assay. The ECL coreactants described in Example 1 were tested for sensitivity to the presence of TRITON™ X-100. FIG. 13A shows the ECL signal from BTI and FT for each ECL reactant in TRITON™ X-100 (TX100) and PEG(18) tridecyl ether (PEG18TDE). FIG. 13B shows the ratio of ECL generated in TRITON™ X-100 vs. PEG(18) tridecyl ether.

DETAILED DESCRIPTION OF THE INVENTION

Figures 2A, 2B, 2C:
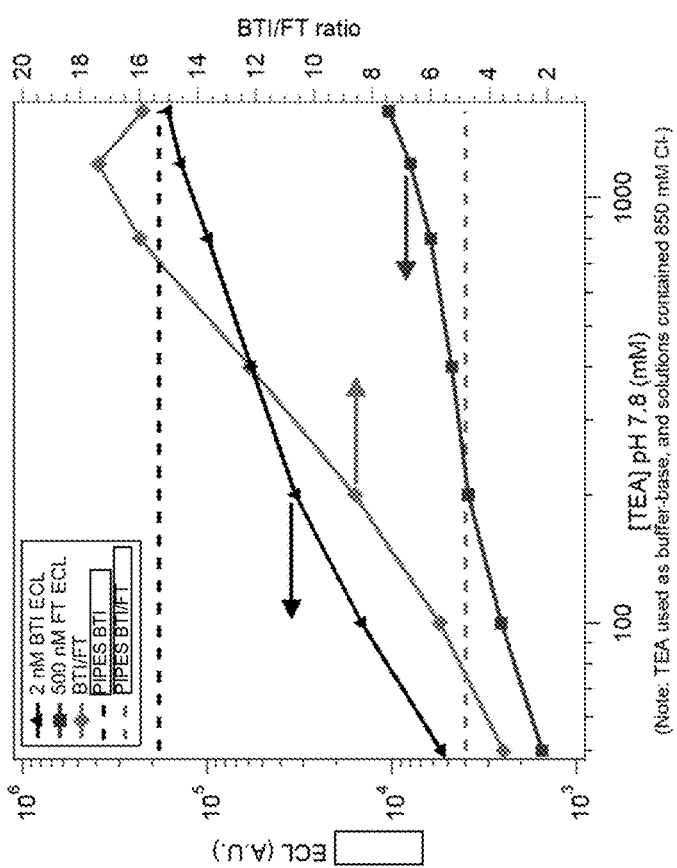
FIGS. 2A-2C relate to Example 2 and show the results of an embodiment of an ECL-based assay.

ECL coreactants of the present invention provide consistent ECL generation across different assay formats. It was discovered that the compositions herein, e.g., comprising triethanolamine (TEA), are useful in ECL-based assays that do not require a wash step. Many ECL-based assays conducted on solid surfaces involve at least one wash step to remove unbound ECL labels prior to detecting the ECL labels on the surface (i.e., a "washed" assay). The wash step may be eliminated if the detection method can effectively discriminate between an ECL label bound to the surface (e.g., as part of a binding complex to be detected) or an unbound, "free" ECL label in solution. A "non-wash" assay format, which eliminates the wash step, is often advantageous because the washing step can be difficult or cumbersome to perform in many circumstances. However, a non-wash assay format is typically difficult to develop due to high background ECL signal from incomplete discrimination of free vs. bound ECL labels present in the reaction mixture.

In ECL-based assays conducted on solid surfaces, triethanolamine (TEA) was surprisingly discovered to discriminate between unbound ("free") ECL labels in solution, versus surface-bound ECL labels to high degree. Compositions described herein, comprising TEA, increase the ratio of ECL signal from bound label to ECL signal from free label relative to conventional to compositions comprising conventional coreactants such as tripropylamine (TPA). Thus, the compositions herein provide improved assay performance, particularly when measuring low affinity interactions, which require the presence of the ECL label in high concentrations in the reaction, but would also be expected to suffer from significant signal loss due to binding complex dissociation during wash steps.

ECL signal generated from the compositions herein, e.g., comprising TEA, tert-butyldiethanolamine (tBDEA), methyldiethanolamine (MDEA), and/or 3-[Bis-(2-hydroxyethyl)-amino]-propane-1-sulfonic acid (DEA-PS) provide further advantages such as improved consistency in performance between compositions that differ based on the presence or absence or surfactant, or based on the surfactant identity. In particular, the compositions perform similarly when containing no surfactant, when containing a mild surfactant that does not disrupt lipid bilayer membranes (such as polyethylene glycol (18) tridecyl ether), or when containing a harsher surfactant (such as TRITON™ X-100). Thus, a harsh surfactant (e.g., TRITON™ X-100, which disrupts lipid bilayer membranes that part of certain analytes of interest such as whole cells or extracellular vesicles) is not required in the compositions comprising the ECL coreactants described herein, which is in contrast to tripropylamine (TPA), a typical ECL coreactant that usually requires TRITON™ X-100 for optimal ECL generation. Thus, the compositions herein are useful in assays to detect analytes that are sensitive to harsh surfactants. Moreover, the ECL coreactants ECL signals are not greatly affected by the presence of different surfactants, and thus, these ECL coreactants are versatile and can be easily incorporated in different formulations while maintaining their ECL generation capabilities.

Thus, the compositions herein, e.g., comprising TEA, tBDEA, MDEA, and/or DEA-PS advantageously expand the types of ECL-based assays that can be performed.

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." (whether italicized or not) means that the specific terms recited are representative examples and embodiments of the invention that are not intended to be limited to the specific examples referenced or cited unless explicitly stated otherwise.

As used herein, "between" is a range inclusive of the ends of the range. For example, a number between x and y explicitly includes the numbers x and y, and any numbers (including fractional numbers and whole numbers) that fall within x and y. Moreover, reference herein to a range of from "5 to 10" includes whole numbers of 5, 6, 7, 8, 9, and 10, and fractional numbers 5.1, 5.2, 5.3, 5.4, 5.5, 5.6, 5.7, 5.8, 5.9, etc. Reference to any numerical range expressly includes each numerical value (including fractional numbers and whole numbers) encompassed by that range. To illustrate, a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

As used herein, the term "substantially," or "substantial," is applicable when used in a negative connotation to refer to the complete or near complete lack of an action, characteristic, property, state, structure, item, or result. For example, a surface that is "substantially" flat would be either completely flat, or so nearly flat that the effect would be the same as if it were completely flat. In a further example, a composition that is "substantially" free of a certain component would not have any amount of that component, or the component would be present in such a low amount in the composition that the effect would be the same as if the component was not present.

In embodiments, the invention provides a composition comprising: (a) triethanolamine (TEA); and (b) an ionic component; wherein the composition has a pH of about 7.0 to about 8.0, and wherein the composition is substantially free of an additional pH buffering component.

In embodiments, the invention provides a composition comprising: (a) triethanolamine (TEA); (b) an ionic component; and (c) an ECL-labeled component; wherein the composition has a pH of about 7.0 to about 8.0, and wherein the composition is substantially free of an additional pH buffering component.

In embodiments, the invention provides a composition comprising: (a) about 1000 mM to about 6500 mM of triethanolamine (TEA); and (b) about 500 mM to about 2000 mM of an ionic component; wherein the composition has a pH of about 7.0 to about 8.0.

In embodiments, the invention provides a composition comprising: (a) triethanolamine (TEA); (b) an ionic component; (c) an alkyl ether-polyethylene glycol (PEG); wherein the composition has a pH of about 7.0 to about 8.0.

In embodiments, the invention provides a composition comprising (a) TEA, (b) an ionic component; and (c) optionally, one or both of an ECL-labeled component and a surfactant, wherein the composition has a pH of about 7.0 to about 8.0, and optionally wherein the composition is substantially free of an additional pH buffering component.

In embodiments, the invention provides a composition comprising: (a) an electrochemiluminescence (ECL) co-reactant selected from N-tert-butyldiethanolamine (tBDEA) methyldiethanolamine (MDEA), 3-[Bis-(2-hydroxy-ethyl)-amino]-propane-1-sulfonic acid (DEA-PS), and combination thereof; (b) an ionic component; and (c) a surfactant; wherein the composition has a pH of about 7.0 to about 8.0.

In embodiments, the invention provides composition that consist of or consist essentially of the recited components at the recited amounts. In compositions that consist essentially of the recited components, such compositions specifically exclude components that materially affect the ECL generating properties of the composition. The ECL generating properties of a composition can be determined by methods known to one of skill in the art. For example, the composition can be contacted with a known quantity of an ECL label on an electrode, and a voltage is applied to the electrode, thereby generating ECL. In embodiments, "materially unaffected" ECL generating properties means that a composition "consisting essentially of" the recited components generate about 80%, about 90%, about 95%, about 98%, about 99%, about 100%, about 101%, about 102%, about 105%, about 110%, or about 120% ECL as a composition "consisting of" the recited components. In embodiments, a composition that consists essentially of the recited components specifically excludes additional ECL-generating compounds, e.g., additional ECL co-reactants.

In embodiments, the invention provides a composition consisting essentially of: (a) triethanolamine (TEA); (b) an ionic component; and (c) a surfactant; wherein the composition has a pH of about 7.0 to about 8.0, and wherein the composition is substantially free of an additional pH buffering component. In embodiments, the invention provides a composition consisting of: (a) triethanolamine (TEA); (b) an ionic component; and (c) a surfactant; wherein the composition has a pH of about 7.0 to about 8.0, and wherein the composition is substantially free of an additional pH buffering component.

In embodiments, the invention provides a composition consisting essentially of: (a) triethanolamine (TEA); (b) an ionic component; (c) a surfactant; and (d) an ECL-labeled component, wherein the composition has a pH of about 7.0 to about 8.0, and wherein the composition is substantially free of an additional pH buffering component. In embodiments, the invention provides a composition consisting of: (a) triethanolamine (TEA); (b) an ionic component; (c) a surfactant; and (d) an ECL-labeled component, wherein the composition has a pH of about 7.0 to about 8.0.

In embodiments, the invention provides a composition consisting essentially of: (a) about 1000 mM to about 6500 mM of triethanolamine (TEA); (b) about 500 mM to about 2000 mM of an ionic component; and (c) a surfactant; wherein the composition has a pH of about 7.0 to about 8.0. In embodiments, the invention provides a composition consisting of: (a) about 1000 mM to about 6500 mM of triethanolamine (TEA); (b) about 500 mM to about 2000 mM of an ionic component; and (c) a surfactant; wherein the composition has a pH of about 7.0 to about 8.0.

In embodiments, the invention provides a composition consisting essentially of: (a) about 1000 mM to about 6500 mM of triethanolamine (TEA); (b) about 500 mM to about 2000 mM of an ionic component; (c) a surfactant; and (d) an ECL-labeled component, wherein the composition has a pH of about 7.0 to about 8.0. In embodiments, the invention provides a composition consisting of: (a) about 1000 mM to about 6500 mM of triethanolamine (TEA); (b) about 500 mM to about 2000 mM of an ionic component; (c) a surfactant; and (d) an ECL-labeled component, wherein the composition has a pH of about 7.0 to about 8.0.

In embodiments, the invention provides a composition consisting essentially of: (a) triethanolamine (TEA); (b) an ionic component; (c) an alkyl ether-polyethylene glycol (PEG); wherein the composition has a pH of about 7.0 to about 8.0. In embodiments, the invention provides a composition consisting of: (a) triethanolamine (TEA); (b) an ionic component; (c) an alkyl ether-polyethylene glycol (PEG); wherein the composition has a pH of about 7.0 to about 8.0.

In embodiments, the invention provides a composition consisting essentially of: (a) triethanolamine (TEA); (b) an ionic component; (c) an alkyl ether-PEG; and (d) an ECL-labeled component, wherein the composition has a pH of about 7.0 to about 8.0. In embodiments, the invention provides a composition consisting of: (a) triethanolamine (TEA); (b) an ionic component; (c) an alkyl ether-PEG; and (d) an ECL-labeled component, wherein the composition has a pH of about 7.0 to about 8.0.

In embodiments, the invention provides a composition consisting essentially of: (a) an electrochemiluminescence (ECL) co-reactant selected from N-tert-butyldiethanolamine (tBDEA), methyldiethanolamine (MDEA), 3-[Bis-(2-hydroxy-ethyl)-amino]-propane-1-sulfonic acid (DEA-PS), and combination thereof; (b) an ionic component; (c) a surfactant; and (d) a pH buffering component, wherein the composition has a pH of about 7.0 to about 8.0. In embodiments, the invention provides a composition consisting of: (a) an electrochemiluminescence (ECL) co-reactant selected from N-tert-butyldiethanolamine (tBDEA), methyldiethanolamine (MDEA), 3-[Bis-(2-hydroxy-ethyl)-amino]-propane-1-sulfonic acid (DEA-PS), and combination thereof; (b) an ionic component; (c) a surfactant; and (d) a pH buffering component, wherein the composition has a pH of about 7.0 to about 8.0.

In embodiments, the invention provides a composition consisting essentially of: (a) an ECL co-reactant selected from tBDEA, MDEA, DEA-PS, and combination thereof; (b) an ionic component; (c) a surfactant; (d) a pH buffering component, and (e) an ECL-labeled component, wherein the composition has a pH of about 7.0 to about 8.0. In embodiments, the invention provides a composition consisting of: (a) an ECL co-reactant selected from tBDEA, MDEA, DEA-PS, and combination thereof; (b) an ionic component; (c) a surfactant; (d) a pH buffering component, and (e) an ECL-labeled component, wherein the composition has a pH of about 7.0 to about 8.0.

As discussed herein, the ECL coreactants herein advantageously provide consistent ECL generation across different assay formats (e.g., washed and non-wash assays) and in combination with different classes of surfactants (e.g., mild surfactants that do not disrupt lipid bilayer membranes and harsher surfactants that can disrupt lipid bilayer membranes). Thus, compositions comprising the ECL coreactants herein (also referred to as "ECL read buffers") are useful in a wide range of ECL-based binding assays.

In embodiments, the ECL coreactant comprises a tertiary amine. In embodiments, the ECL coreactant comprises a tertiary alkylamine. In embodiments, the ECL coreactant comprises a tertiary hydroxyalkylamine. In embodiments, the ECL coreactant comprises a zwitterionic tertiary amine. In embodiments, the ECL coreactant comprises a secondary amine. In embodiments, the ECL coreactant is tributylamine (TBA), (dibutyl) aminoethanol (DBAE), (diethyl) aminoethanol (DEAE), triethanolamine (TEA), butyldiethanolamine (BDEA), propyldiethanolamine (PDEA), ethyldiethanolamine (EDEA), methyldiethanolamine (MDEA), tert-butyldiethanolamine (tBDEA), dibutylamine (DBA), butylethanolamine (BEA), diethanolamine (DEA), dibutylamine propylsulfonate (DBA-PS), dibutylamine butylsulfonate (DBA-BS), butylethanolamine propylsulfonate (BEA-PS), butylethanolamine butylsulfonate (BEA-BS), diethanolamine propylsulfonate (also known as 3-[Bis-(2-hydroxy-ethyl)-amino]-propane-1-sulfonic acid; DEA-PS), or diethanolamine butylsulfonate (DEA-BS). Structures of exemplary ECL coreactants described herein are shown below.

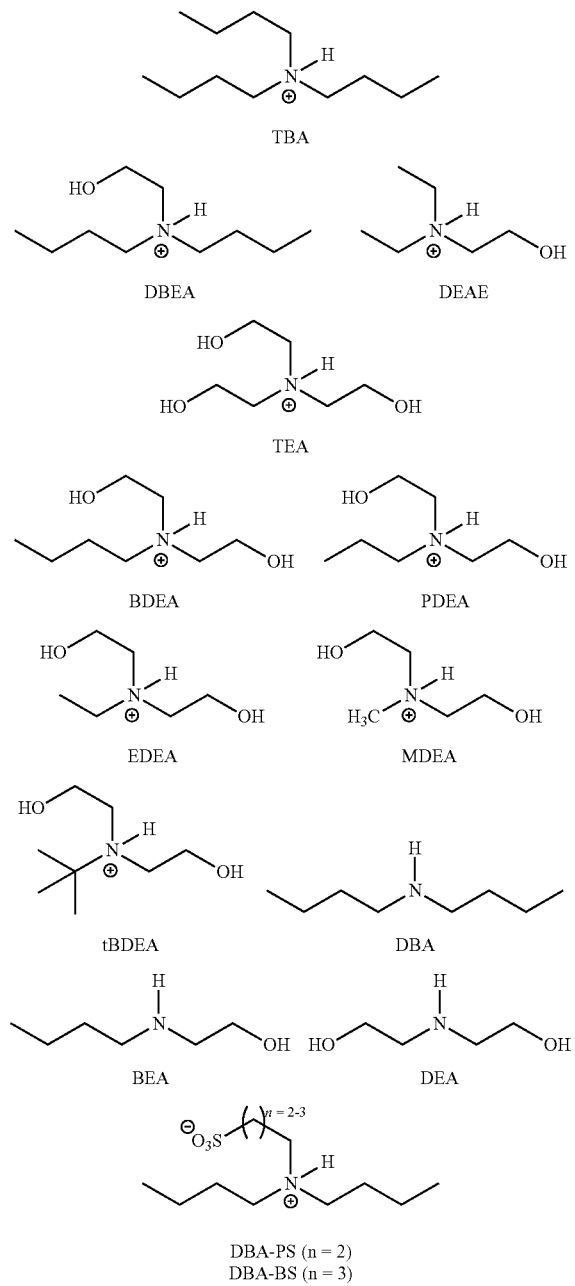

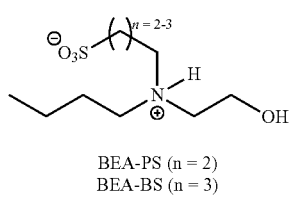

-continued

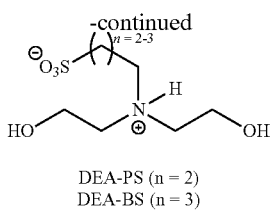

DEA-PS (n = 2)
DEA-BS (n = 3)

Triethanolamine ECL Coreactant

The present invention provides compositions comprising an ECL coreactant. In embodiments, the ECL coreactant is triethanolamine (TEA). As discussed herein, it was discovered that TEA provides advantageous ECL generating properties in non-wash binding assays. In assays where the species of interest (e.g., analyte or binding complex as described herein) is captured and detected on a solid surface, TEA is capable of discriminating between "free" ECL labels that are not part of the species to be detected (e.g., analyte or binding complex) and "bound" ECL labels that are part of the species (e.g., analyte or binding complex) bound to the surface. Non-wash binding assays that utilize TEA as ECL coreactant have decreased non-specific ECL from the ECL label to the species to be detected, thereby decreasing the background ECL and increasing the signal-to-background ratio of the assay. In embodiments, a non-wash assay using TEA as ECL coreactant has a 2-fold higher, 3-fold higher, 4-fold higher, 5-fold higher, or 10-fold higher signal-to-background ratio as compared with an assay using tripropylamine (TPA) or piperazine-N,N'-bis(2-ethanesulfonic acid) (PIPES) as ECL coreactant. In embodiments, a non-wash assay using TEA as ECL coreactant has a 2-fold lower, 3-fold lower, 4-fold lower, 5-fold lower, 10-fold lower, 20-fold lower, or 40-fold lower limit of detection as compared with an assay using TPA or PIPES as ECL coreactant.

A further advantage of TEA as an ECL coreactant is the insensitivity of TEA to sample matrices and/or interferents. This is particularly beneficial in the context of non-wash assays, in which the reaction mixture may contain matrices from human or animal sources (e.g., containing proteins, cellular components and debris, culture media, and the like), which can also contain metabolite and/or drug interferents such as, e.g., acetaminophen, ibuprofen, naproxen, salicylic acid, and/or tolbutamine. In embodiments, TEA generates substantially the same ECL signal in a reaction mixture comprising one or more sample matrices and/or one or more interferents, as in a reaction mixture that does not comprise a sample matrix and/or an interferent.

It was further discovered that TEA provides the benefit of generating consistent ECL signal when used in the absence of surfactants or when combined with different types of surfactants, e.g., harsh and mild surfactants described herein. As used herein, a "harsh" surfactant is capable of disrupting, lysing and/or dissolving a lipid bilayer membrane (e.g., a membrane of a cell or an extracellular vesicle (EV)). In contrast, a "mild" surfactant does not disrupt, lyse or dissolve a lipid bilayer membrane. In embodiments, a composition comprising TEA and a harsh surfactant generates substantially similar ECL signal as a composition comprising identical components except that a mild surfactant is present instead of a harsh surfactant, when subjected to the same ECL-generating conditions (e.g., voltage waveform, type of electrode, amount of the composition, amount of ECL label, etc.). In embodiments, the harsh surfactant is TRITON™ X-100, TRITON™ X-114, NP-40, IGEPAL® CA-630, 3-[(3-cholamidopropyl) dimethylammonio]-1-propanesulfonate (CHAPS), or sodium dodecylsulfate (SDS). In embodiments, the mild surfactant is a BRIJ®, TWEEN®, PLURONIC®, or KOLLIPHOR® surfactant, or an alkyl ether-PEG surfactant such as PEG(18) tridecyl ether.

TEA has a pKa of about 7.7 and is capable maintaining the pH of a composition within about 7.0 to about 8.0, which is the typical desired pH range for biological assays. Moreover, TEA compositions having a pH of about 7.0 to about 8.0 preferentially generated ECL signal from an electrode-bound ECL label versus an unbound ECL label as described herein. Thus, compositions herein comprising TEA have the additional advantage of pH compatibility with biological assays and not requiring an additional pH buffering component, thereby simplifying the production process and lowering costs of the compositions. In embodiments, the composition comprising TEA is substantially free of an additional pH buffering component. Materials that can act as pH buffering components to maintain solutions within a specific pH range are known to one of skill in the art. For example, buffers that are capable of maintaining a pH of about 7.0 to about 8.0 include, but are not limited to, piperazine-N,N'-bis(2-ethanesulfonic acid) (PIPES), cholamine chloride, 3-(N-morpholino) propanesulfonic acid (MOPS), N-[tris(hydroxymethyl)methyl]-2-aminoethanesulfonic acid (TES), 3-(N,N-bis [2-hydroxyethyl]amino)-2-hydroxypropanesulfonic acid (DIPSO), 4-(N-morpholino) butanesulfonic acid (MOBS), acetamidoglycine, N-[tris(hydroxymethyl)methyl]-3-amino-2-hydroxypropanesulfonic acid (TAPSO), piperazine-1,4-bis(2-hydroxypropanesulfonic acid) dihydrate (POPSO), N-(hydroxyethyl) piperazine-N'-2-hydroxypropanesulfonic acid (HEPPSO), 3-[4-(2-hydroxyethyl) piperazin-1-yl]propane-1-sulfonic acid (HEPPS), tricine, glycinamide, N-(2-hydroxyethyl) piperazine-N'-(4-butanesulfonic acid) (HEPBS), and bicine. Further non-limiting examples of pH buffering components include tris(hydroxymethyl) aminomethane ("Tris"), phosphate, HEPES, glycylglycine ("GlyGly"), borate, acetate, and citrate. In embodiments, the composition comprising TEA does not comprise any of Tris, phosphate, HEPES, glycylglycine, borate, acetate, and citrate. In embodiments, the composition comprising TEA is substantially free of an additional component having a pKa of about 7.0 to about 8.0.

Moreover, many common pH buffering components have a tertiary amine in their structure and are capable of generating ECL. Exemplary pH buffering components that can act as an ECL coreactant are provided in U.S. Pat. No. 6,919,173 and include, but are not limited to, HEPES, POPSO, HEPPSO, and PIPES. In embodiments, the composition comprising TEA is substantially free of an additional ECL coreactant. In embodiments, the composition comprising TEA does not comprise any of HEPES, POPSO, HEPPSO, and PIPES. In embodiments, the composition comprising TEA does not comprise any of Tris, phosphate, HEPES, glycylglycine, borate, acetate, citrate, POPSO, HEPPSO, and PIPES.

In embodiments, the concentration of TEA in the composition is about 500 mM to about 7000 mM, about 800 mM to about 6800 mM, about 1000 mM to about 6500 mM, about 1000 mM to about 6400 mM, about 1000 mM to about 6000 mM, about 1000 mM to about 5500 mM, about 1100 mM to about 5000 mM, about 1100 mM to about 4800 mM, about 1100 mM to about 4000 mM, about 1100 mM to about 3500 mM, about 1100 mM to about 3200 mM, about 1100 mM to about 3000 mM, about 1100 mM to about 2500 mM, about 1200 mM to about 2400 mM, or about 1200 mM to about 1600 mM. In embodiments, the concentration of TEA in the composition is about 1000 mM, about 1100 mM, about 1200 mM, about 1300 mM, about 1400 mM, about 1500 mM, about 1600 mM, about 1700 mM, about 1800 mM, about 1900 mM, about 2000 mM, about 2100 mM, about 2200 mM, about 2300 mM, about 2400 mM, about 2500 mM, about 2600 mM, about 2700 mM, about 2800 mM, about 2900 mM, about 3000 mM, about 3100 mM, about 3200 mM, about 3300 mM, about 3400 mM, about 3500 mM, about 3600 mM, about 3700 mM, about 3800 mM, about 3900 mM, about 4000 mM, about 4100 mM, about 4200 mM, about 4300 mM, about 4400 mM, about 4500 mM, about 4600 mM, about 4700 mM, about 4800 mM, about 4900 mM, about 5000 mM, about 5100 mM, about 5200 mM, about 5300 mM, about 5400 mM, about 5500 mM, about 5600 mM, about 5700 mM, about 5800 mM, about 5900 mM, about 6000 mM, about 6100 mM, about 6200 mM, about 6300 mM, about 6400 mM, about 6500 mM, about 6600 mM, about 6700 mM, about 6800 mM, about 6900 mM, or about 7000 mM. In embodiments, the concentration of TEA in the composition is at least about 1000 mM, at least about 1200 mM, at least about 1600 mM, at least about 1800 mM, at least about 2000 mM, at least about 2500 mM, at least about 3000 mM, at least about 3500 mM, at least about 4000 mM, at least about 4500 mM, at least about 5000 mM, at least about 5500 mM, or at least about 6000 mM. Surprisingly, TEA concentration in the composition showed a positive correlation with strength of the generated ECL signal, which was unexpected as other ECL coreactants such as PIPES (which was expected to behave similarly to TEA, as PIPES and TEA both have the ability to confine ECL near the electrode as described herein) have shown decrease in ECL generation with increasing ECL coreactant concentration (see, e.g., FIGS. 3A and 3B). Thus, the TEA compositions provided herein are capable of preferentially and consistently generating ECL signal from an electrode-bound ECL label versus an unbound ECL label as described herein, over a broad concentration range, e.g., from about 1000 mM to about 6500 mM. The consistency of electrode-bound ECL generation decreases variability in ECL generation in ECL-based assays, e.g., in washed or non-washed assay formats. An ECL coreactant that can be used at a high concentration, e.g., TEA, provides advantages in non-wash assays by minimizing dilution of the sample and/or assay mixture, avoiding perturbation of the binding equilibrium and kinetics of the assay components, and therefore maximizing ECL signal. An ECL coreactant that can be used at high concentrations, e.g., TEA, are also useful in assays with lower affinity binding and/or detection reagents, providing improved sensitivity as compared with ECL coreactants that cannot be used at high concentrations (e.g., PIPES).

Alkyl Diethanolamine/Zwitterionic Tertiary Amine ECL Coreactant

The present invention further provides compositions comprising an alkyl diethanolamine ECL coreactant and/or a zwitterionic tertiary amine ECL coreactant. In embodiments, the alkyl diethanolamine is butyldiethanolamine (BDEA), propyldiethanolamine (PDEA), ethyldiethanolamine (EDEA), methyldiethanolamine (MDEA), or tert-butyldiethanolamine (tBDEA). In embodiments, the alkyl diethanolamine is N-tert-butyldiethanolamine (tBDEA) or methyldiethanolamine (MDEA). In embodiments, the zwitterionic tertiary amine ECL coreactant is dibutylamine propylsulfonate (DBA-PS), dibutylamine butylsulfonate (DBA-BS), butylethanolamine propylsulfonate (BEA-PS), butylethanolamine butylsulfonate (BEA-BS), diethanolamine propylsulfonate (also known as 3-[Bis-(2-hydroxy-ethyl)-amino]-propane-1-sulfonic acid; DEA-PS), or diethanolamine butylsulfonate (DEA-BS). In embodiments, the zwitterionic tertiary amine ECL coreactant is DEA-PS. It was discovered that tBDEA, MDEA, and DEA-PS advantageously show consistent ECL generating properties when used in the absence of surfactant or when combined with different types of surfactants, e.g., harsh and mild surfactants described herein. In embodiments, a composition comprising tBDEA, MDEA, and/or DEA-PS and a harsh surfactant generates substantially similar ECL signal as a composition comprising identical components except that a mild surfactant is present instead of a harsh surfactant, when subjected to the same ECL-generating conditions (e.g., voltage waveform, type of electrode, amount of the composition, amount of ECL label, etc.). In embodiments, the harsh surfactant is TRITON™ X-100, TRITON™ X-114, NP-40, IGEPAL® CA-630, 3-[(3-cholamidopropyl) dimethylammonio]-1-propanesulfonate (CHAPS), or sodium dodecylsulfate (SDS). In embodiments, the mild surfactant is a BRIJ®, TWEEN®, PLURONIC®, or KOLLIPHOR® surfactant, or an alkyl ether-PEG surfactant such as PEG(18) tridecyl ether.

In embodiments, the concentration of the alkyl diethanolamine or the zwitterionic tertiary amine in the composition is about 10 mM to about 500 mM, about 20 mM to about 400 mM, about 50 mM to about 250 mM, or about 100 mM to about 200 mM. In embodiments, the concentration of the alkyl diethanolamine the zwitterionic tertiary amine in the composition is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 350 mM, about 400 mM, about 450 mM, or about 500 mM. In embodiments, the alkyl diethanolamine is tBDEA. In embodiments, the alkyl diethanolamine is MDEA. In embodiments, the alkyl diethanolamine is a combination of tBDEA and MDEA. In embodiments, the zwitterionic tertiary amine is DEA-PS. In embodiments, the composition comprises a combination of two or more of tBDEA, MDEA, and DEA-PS.

In embodiments, the composition comprising the alkyl diethanolamine and/or zwitterionic tertiary amine (e.g., tBDEA, MDEA, and/or DEA-PS), further comprises a pH buffering component. In embodiments, the pH buffering component has a pKa of about 7.0 to about 8.0. In embodiments, the pH buffering component is capable of maintaining pH of the composition at about 7.0 to about 8.5, about 7.2 to about 8.0, or about 7.4 to about 7.9. In embodiments, the pH buffering component comprises Tris, phosphate, HEPES, glycylglycine, borate, acetate, citrate, PIPES, MOPS, TES, DIPSO, MOBS, TAPSO, POPSO, HEPPSO, HEPPS, tricine, glycinamide, HEPBS, bicine, or a combination thereof. In embodiments, the pH buffering component is Tris, phosphate, HEPES, glycylglycine, borate, acetate, citrate, or a combination thereof. In embodiments, the pH buffering component comprises Tris. In embodiments, the pH buffering component comprises phosphate.

In embodiments, the concentration of the pH buffering component in the composition is about 10 mM to about 800 mM, about 20 mM to about 600 mM, about 50 mM to about 400 mM, about 100 mM to about 300 mM, about 120 mM to about 280 mM, or about 150 mM to about 250 mM. In embodiments, the concentration of the pH buffering component in the composition is about 50 mM, about 100 mM, about 150 mM, about 200 mM, about 250 mM, about 300 mM, about 350 mM, about 400 mM, about 450 mM, or about 500 mM.

Ionic Component

In embodiments, the compositions herein comprise an ionic component. Ionic components, such as salts, dissociate into ions in solution. It was discovered that high ion concentrations can advantageously reduce non-specific binding of an ECL label with the ECL coreactant. Non-limiting examples of ionic components include salts comprising the cations $Li^+$, $Na^+$, $K^+$, $Rb^+$, $Cs^+$, $Mg^{+2}$, $Ca^{+2}$, and $NH_4^+$, and/or salts comprising the anions $F^-$, $Cl^-$, $Br^-$, $I^-$, phosphate, sulfate, and borate. In embodiments, the ionic component comprises $Li^+$, $Na^+$, or $K^+$. In embodiments, the ionic component comprises $Cl^-$. In embodiments, the ionic component comprises lithium chloride (LiCl), sodium chloride (NaCl), potassium chloride (KCl), or a combination thereof. In embodiments, the ionic component comprises NaCl. In embodiments, the ionic component comprises KCl.

In embodiments, the concentration of the ionic component in the composition is about 100 mM to about 2000 mM, about 200 mM to about 1800 mM, about 300 mM to about 1700 mM, about 400 mM to about 1600 mM, about 500 mM to about 1500 mM, about 600 mM to about 1200 mM, about 700 mM to about 1000 mM, or about 800 mM to about 900 mM. In embodiments, the concentration of the ionic component in the composition is about 500 mM, about 550 mM, about 600 mM, about 650 mM, about 700 mM, about 750 mM, about 800 mM, about 850 mM, about 900 mM, about 950 mM, about 1000 mM, about 1100 mM, about 1200 mM, about 1300 mM, about 1400 mM, or about 1500 mM.

In embodiments, the composition comprises about 100 mM to about 2000 mM, about 200 mM to about 1800 mM, about 300 mM to about 1700 mM, about 400 mM to about 1600 mM, about 500 mM to about 1500 mM, about 600 mM to about 1200 mM, about 700 mM to about 1000 mM, or about 800 mM to about 900 mM NaCl. In embodiments, the composition comprises about 100 mM to about 2000 mM, about 200 mM to about 1800 mM, about 300 mM to about 1700 mM, about 400 mM to about 1600 mM, about 500 mM to about 1500 mM, about 600 mM to about 1200 mM, about 700 mM to about 1000 mM, or about 800 mM to about 900 mM KCl. In embodiments, the composition comprises about 100 mM to about 2000 mM, about 200 mM to about 1800 mM, about 300 mM to about 1700 mM, about 400 mM to about 1600 mM, about 500 mM to about 1500 mM, about 600 mM to about 1200 mM, about 700 mM to about 1000 mM, or about 800 mM to about 900 mM LiCl.

In embodiments, the composition has an ionic strength of about 0.2 M to about 2 M, about 0.5 M to about 1.5 M, about 0.75 M to about 1.25 M, or about 0.8 M to about 1.0 M. In embodiments, the composition has an ionic strength of greater than or about 0.3 M, greater than or about 0.5 M, greater than or about 0.8 M, or greater than or about 1.0 M. In embodiments, the composition comprises chloride ion and the concentration of the chloride ion is greater than or about 0.3 M, greater than or about 0.5 M, greater than or about 0.8 M, or greater than or about 1.0 M.

In embodiments, non-specific binding (NSB) in an immunoassay with ECL as the assay readout is lower with the composition containing the ionic component as compared to an otherwise identical composition containing no ionic component.

Surfactant

It was unexpectedly discovered that when using compositions provided herein, e.g., comprising TEA, tBDEA, MDEA and/or DEA-PS as ECL coreactant, the ECL generating properties of the composition are substantially unaffected by the presence, concentration, or structure of surfactants in the composition. In contrast, TPA-based compositions generally require the presence of surfactants for optimal signal generation. In particular, TPA provides optimal ECL generation in the presence of surfactants comprising aromatic moieties, such as the phenolic ether moiety in TRITON™ X-100.

In embodiments, the compositions herein are substantially free of a surfactant. In embodiments, the compositions herein comprise a surfactant. In embodiments, the compositions herein comprise a surfactant at a concentration below the critical micellar concentration (CMC) of the surfactant. The CMC is the concentration of surfactants above which micelles form, and any additional amount of surfactant added to the composition above the CMC are incorporated into the micelles. The CMC of a surfactant can be determined by one of skill in the art, e.g., using a titration method as described in Wu et al., Anal Chem 92 (6): 4259-4265 (2020), and/or using devices such as a dynamic contact angle measuring device and/or a tensiometer.

In embodiments, the compositions herein comprise a non-ionic surfactant. In embodiments, the compositions herein comprise an ionic surfactant. Non-ionic surfactants include the surfactant classes known by the trade names of NONIDET™ (octylphenoxypolyethoxyethanol), BRIJ® (polyoxyethylene fatty ether), TRITON™ (2-[4-(2,4,4-trimethylpentan-2-yl)phenoxy]ethanol), TWEEN® (polysorbate), KOLLIPHOR® (polyoxyl castor oil), THESIT® (polyethylene glycol dodecyl ether), LUBROL® (polyoxyethylene alkyl ether), GENAPOL® (iso-tridecyl alcohol polyglycol ether), PLURONIC® (poloxamer block copolymers of poly(ethylene oxide) (PEO) and poly(propylene oxide) (PPO) arranged as PEO-PPO-PEO), TETRONIC® (poloxamine block copolymers of PEO-PPO), SYNPERONIC® (block copolymer of poly(ethylene glycol) (PEG) and poly(propylene glycol) (PPG) arranged as PEG-PPG-PEG), and SPAN® (sorbitan). Specific examples of non-ionic surfactants include, e.g., KOLLIPHOR® P-407 ($PEG_{101}$-$PPG_{56}$-$PEG_{101}$; also known as Poloxamer 407), PLURONIC® P-123 ($PEO_{18}$-$PPO_{72}$-$PEO_{18}$), PLURONIC® L-121 ($PEG_5$-$PPG_{68}$-$PEG_5$), PLURONIC® 31R1 ($PPO_{26}$-$PEO_5$-$PPO_{26}$), TETRONIC® 701 (ethylenediamine tetrakis(propoxylate-block-ethoxylate) tetrol), BRIJ® L4 (polyethylene glycol dodecyl ether), BRIJ® 58 (polyethylene glycol hexadecyl ether), TWEEN® 20 (polysorbate 20), 2,4,7,9-tetramethyl-d-decyne-4,7-diol ethoxylate, and alkyl ether-polyethylene glycols (PEG) such as PEG(10) tridecyl ether, PEG(12) tridecyl ether, and PEG (18) tridecyl ether).

In embodiments, the surfactant comprises a phenol ether. In embodiments, the surfactant is 2-[4-(2,4,4-trimethylpentan-2-yl)phenoxy]ethanol (TRITON™ X-100). In the context of surfactants described herein, TRITON™ X-100 is a "harsh" surfactant that is capable of disrupting, lysing and/or dissolving a lipid bilayer membrane, e.g., a membrane of a cell or an extracellular vesicle (EV).

In embodiments, the surfactant does not comprise an aromatic moiety. In embodiments, the surfactant does not comprise a phenol ether. In embodiments, the surfactant does not disrupt, lyse or dissolve a lipid bilayer membrane, e.g., a membrane of a cell or an extracellular vesicle (EV). Such surfactants can be referred to as "mild" surfactants. Examples of mild surfactants include the surfactant classes known by the trade names BRIJ®, TWEEN®, PLURONIC®, or KOLLIPHOR®. In embodiments, the surfactant does not comprise an ester linkage. In embodiments, the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis (propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is an alkyl ether-polyethylene glycol (PEG). In embodiments, the alkyl ether-polyethylene glycol (PEG) is PEG(10) tridecyl ether, PEG(12) tridecyl ether, PEG(18) tridecyl ether, or a combination thereof. In embodiments, the surfactant is PEG (18) tridecyl ether.

As described herein, the compositions herein advantageously provide consistent ECL signal generation in the presence of different types of surfactants, e.g., harsh and mild surfactants described herein. In embodiments, a composition comprising TEA, tBDEA, MDEA, DEA-PS, or a combination thereof and a harsh surfactant generates substantially similar ECL signal as a composition comprising identical components except that a mild surfactant is present instead of a harsh surfactant, when subjected to the same ECL-generating conditions (e.g., voltage waveform, type of electrode, amount of the composition, amount of ECL label, etc.). In embodiments, the harsh surfactant is TRITON™ X-100. In embodiments, the mild surfactant is a BRIJ®, TWEEN®, PLURONIC®, or KOLLIPHOR® surfactant, or an alkyl ether-PEG surfactant such as PEG(18) tridecyl ether.

In embodiments, the concentration of the surfactant in the composition is such that the composition has an air-liquid surface tension of less than or about 50 dyne/cm, less than or about 40 dyne/cm or less than or about 35 dyne/cm. In embodiments, the surfactant is present in the composition at its cmc, greater than or about two times its cmc, or greater than or about five times its cmc.

In embodiments, the surfactant is about 0.1% (v), about 0.5% (v/v), about 1% (v/v), about 2% (v/v), about 5% (v/v), about 7% (v/v), or about 10% (v/v) of the composition. In embodiments, the concentration of the surfactant in the composition is about 0.1 mM to about 20 mM, about 0.1 mM to about 10 mM, about 0.5 mM to about 8 mM, about 0.75 mM to about 6 mM, or about 1 mM to about 5 mM. In embodiments, the concentration of the surfactant in the composition is about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, or about 10 mM.

In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM 2-[4-(2,4,4-trimethylpentan-2-yl)phenoxy]ethanol (TRITON™ X-100). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM Poloxamer 407 (KOLLIPHOR® P-407). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM $PEO_{18}$-$PPO_{72}$-$PEO_{18}$ (PLURONIC® P-123). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM $PEG_5$-$PPG_{68}$-$PEG_5$ (PLURONIC® L-121). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM $PPO_{26}$-$PEO_5$-$PPO_{26}$ (PLURONIC®31R1). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM ethylenediamine tetrakis(propoxylate-block-ethoxylate) tetrol (TETRONIC® 701). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM polyethylene glycol dodecyl ether (BRIJ® L4). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM polyethylene glycol hexadecyl ether (BRIJ® 58). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM polysorbate 20 (TWEEN® 20). In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM 2,4,7,9-tetramethyl-d-decyne-4,7-diol ethoxylate. In embodiments, the composition comprises about 0.1 mM to about 20 mM, about 0.1 mM to about 10 mM, about 0.5 mM to about 8 mM, about 0.75 mM to about 6 mM, or about 1 mM to about 5 mM alkyl ether-PEG. In embodiments, the alkyl ether-PEG is PEG(18) tridecyl ether.

pH

In embodiments, the compositions herein have a pH of about 6.0 to about 9.0, pH of about 7.0 to about 8.0, pH of about 7.2 to about 7.6, pH of about 7.5 to about 7.8, pH of about 7.4 to about 7.9, pH of about 7.0, about 7.1, about 7.2, about 7.3, about 7.4, about 7.5, about 7.6, about 7.7, about 7.8, about 7.9, or about 8.0. In embodiments, the pH of the composition is about 7.5. In embodiments, the pH of the composition is about 7.8.

In embodiments, the composition comprising TEA has a pH of about 7.0 to about 8.0, about 7.4 to about 7.9, or about 7.5 to about 7.8, and is substantially free of an additional pH buffering component. In embodiments, the composition comprising TEA has a pH of about 7.0 to about 8.0, about 7.4 to about 7.9, or about 7.5 to about 7.8, and is substantially free of an additional component having a pKa of about 7.0 to about 8.0. In embodiments, the composition comprising TEA does not comprise any of Tris, phosphate, HEPES, glycylglycine, borate, acetate, and citrate. In embodiments, the composition comprising TEA does not comprise any of HEPES, POPSO, HEPPSO, and PIPES. In embodiments, the composition comprising TEA does not comprise any of Tris, phosphate, HEPES, glycylglycine, borate, acetate, citrate, POPSO, HEPPSO, and PIPES.

ECL-Labeled Component

In embodiments, the compositions herein comprise an ECL-labeled component. In embodiments, the ECL coreactant composition provided herein, e.g., comprising TEA, tBDEA, MDEA and/or DEA-PS and the ECL-labeled component, is capable of generating ECL. In embodiments, the ECL-labeled component comprises an ECL label. In embodiments, the ECL-labeled component comprises a detection reagent. In embodiments, the ECL-labeled component comprises a binding partner of a detection reagent.

In embodiments, ECL-labeled component is a detection reagent that comprises an ECL label. In embodiments, the detection reagent comprises an antibody or antigen-detection fragment thereof, antigen, ligand, receptor, oligonucleotide, hapten, epitope, mimotope, or aptamer. In embodiments, the detection reagent is an antibody or a variant thereof, including an antigen/epitope-detection portion thereof, an antibody fragment or derivative, an antibody analogue, an engineered antibody, or a substance that binds to antigens in a similar manner to antibodies. In embodiments, the detection reagent comprises at least one heavy or light chain complementarity determining region (CDR) of an antibody. In embodiments, the detection reagent comprises at least two CDRs from one or more antibodies. In embodiments, the detection reagent is an antibody or antigen-detection fragment thereof. In embodiments, the detection reagent is covalently linked to the ECL label via a conjugation linker. Methods of conjugating labels, e.g., ECL labels, to detection reagents are known to one of ordinary skill in the art.

In embodiments, the ECL-labeled component is a binding partner of a detection reagent. In embodiments, the ECL-labeled component and the detection reagent form a complex that is capable of being detected by ECL. In embodiments, the ECL-labeled component and the detection reagent comprise a receptor-ligand pair, an antigen-antibody pair, a hapten-antibody pair, an epitope-antibody pair, a mimotope-antibody pair, an aptamer-target molecule pair, or an intercalator-target molecule pair. In embodiments, the ECL-labeled component and the detection reagent comprise complementary oligonucleotides. In embodiments, the ECL-labeled component and the detection reagent comprise a biotin-avidin or biotin-streptavidin pair.

In embodiments, the ECL label comprises an electrochemiluminescent organometallic complex. As used herein, the term "electrochemiluminescent" and "ECL-active" may be used interchangeably. In embodiments, the electrochemiluminescent organometallic complex comprises ruthenium, osmium, iridium, rhenium, and/or a lanthanide metal. In embodiments, the ECL label comprises ruthenium. In embodiments, the electrochemiluminescent organometallic complex comprises a substituted or unsubstituted bipyridine or a substituted or unsubstituted phenanthroline. In embodiments, the ECL label comprises a substituted bipyridine. In embodiments, the ECL label comprises ruthenium (II) tris-bipyridine. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand comprising at least one sulfonate group is a compound of Formula I:

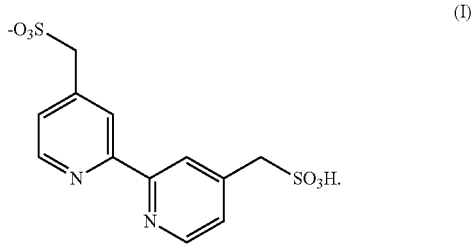

(I)

In embodiments, the ECL label comprises three ligands, wherein a first ligand is a compound of Formula I, and wherein a second ligand comprises a bipyridine having at least one substituent that is covalently linked to the detection reagent. In embodiments, the ECL label comprises an organometallic complex that comprises three ligands, wherein two of the ligands are each a compound of Formula I, and wherein the third ligand comprises a bipyridine having at least one substituent that is covalently linked to the detection reagent.

In embodiments, the first detectable label is a compound of Formula II:

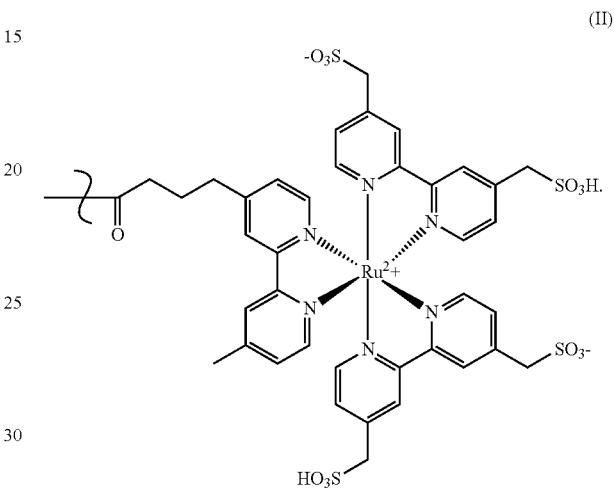

(II)

Further exemplary ECL labels can be found in U.S. Pat. Nos. 5,714,089; 6,136,268; 6,316,607; 6,468,741; 6,479,233; 6,808,939; and 9,499,573.

TEA Compositions

In embodiments, the invention provides a composition comprising about 1000 mM to about 6500 mM TEA and about 500 mM to about 1500 mM ionic component, wherein the composition has a pH of about 7.0 to about 8.0; and wherein the ionic component is NaCl, KCl, or LiCl. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1100 mM to about 3500 mM TEA and about 600 mM to about 1200 mM ionic component, wherein the composition has a pH of about 7.0 to about 8.0; and wherein the ionic component is NaCl, KCl, or LiCl. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM to about 1600 mM TEA and about 700 mM to about 900 mM ionic component, wherein the composition has a pH of about 7.0 to about 8.0; and wherein the ionic component is NaCl, KCl, or LiCl. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label. In embodiments, the composition comprises about 1200 mM TEA and about 850 mM NaCl. In embodiments, the composition comprises about 1600 mM TEA and about 850 mM NaCl. In embodiments, the composition comprises about 1200 mM TEA and about 850 mM KCl. In embodiments, the composition comprises about 1600 mM TEA and about 850 mM KCl. In embodiments, the composition comprises about 1200 mM TEA and about 850 mM LiCl. In embodiments, the composition comprises about 1600 mM TEA and about 850 mM LiCl. In embodiments, the composition has a pH of about 7.5. In embodiments, the composition has a pH of about 7.8.

In embodiments, the invention provides a composition comprising about 1000 mM to about 6500 mM TEA, about 500 mM to about 1500 mM ionic component, and about 0.1 mM to about 10 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1100 mM to about 3500 mM TEA, about 600 mM to about 1200 mM ionic component, and about 0.5 mM to about 8 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM to about 1600 mM TEA, about 700 mM to about 900 mM ionic component, and about 1 mM to about 5 mM surfactant, wherein the composition has a pH of about 7.4 to about 7.9; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM ionic component, and about 1 mM surfactant, wherein the composition has a pH of about 7.4 to about 7.9; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1600 mM TEA, about 850 mM ionic component, and about 1 mM surfactant, wherein the composition has a pH of about 7.4 to about 7.9; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 3200 mM TEA, about 850 mM ionic component, and about 1 mM surfactant, wherein the composition has a pH of about 7.4 to about 7.9; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 6400 mM TEA, about 850 mM ionic component, and about 1 mM surfactant, wherein the composition has a pH of about 7.4 to about 7.9; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1600 mM TEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 3200 mM TEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 6400 mM TEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 850 mM NaCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 850 mM KCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 850 mM LiCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 700 mM to about 900 mM ionic component, and about 1 mM surfactant, wherein the composition has a pH of about 7.0 to about 8.0; wherein the surfactant is 2-[4-(2,4,4-trimethylpentan-2-yl)phenoxy]ethanol (TRITON™ X-100). In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 700 mM to about 900 mM ionic component, and about 1 mM surfactant, wherein the composition has a pH of about 7.0 to about 8.0; wherein the ionic component is NaCl, KCl, or LiCl; and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 700 mM to about 900 mM ionic component, and about 1 mM surfactant, wherein the composition has a pH of about 7.0 to about 8.0; wherein the ionic component is NaCl, KCl, or LiCl; and wherein the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 700 mM to about 900 mM ionic component, and about 1 mM to about 5 mM surfactant, wherein the composition has a pH of about 7.5; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1000 mM to about 6500 mM TEA, about 700 mM to about 900 mM ionic component, and about 1 mM to about 5 mM surfactant, wherein the composition has a pH of about 7.8; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 1200 mM TEA, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 1600 mM TEA, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 1600 mM TEA, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 3200 mM TEA, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 3200 mM TEA, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 6400 mM TEA, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 6400 mM TEA, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM KCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 1200 mM TEA, about 850 mM KCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 1600 mM TEA, about 850 mM KCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 1600 mM TEA, about 850 mM KCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 3200 mM TEA, about 850 mM KCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 3200 mM TEA, about 850 mM KCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 6400 mM TEA, about 850 mM KCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 6400 mM TEA, about 850 mM KCl, and about 1 mM 2-[4-(2,4,4-trimethylpentan-2-yl)phenoxy]ethanol (TRITON™ X-100), wherein the composition has a pH of about 7.8. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM LiCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 1200 mM TEA, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 1600 mM TEA, about 850 mM LiCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 1600 mM TEA, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 3200 mM TEA, about 850 mM LiCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 3200 mM TEA, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 6400 mM TEA, about 850 mM LiCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 6400 mM TEA, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM NaCl, and about 1 mM surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 1200 mM TEA, about 850 mM NaCl, and about 1 mM surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1600 mM TEA, about 850 mM NaCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC®

P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 1600 mM TEA, about 850 mM NaCl, and about 1 surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 3200 mM TEA, about 850 mM NaCl, and about 1 mM surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 3200 mM TEA, about 850 mM NaCl, and about 1 mM surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 6400 mM TEA, about 850 mM NaCl, and about surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 6400 mM TEA, about 850 mM NaCl, and about 1 surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM KCl, and about 1 mM surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 1200 mM TEA, about 850 mM KCl, and about 1 mM surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component.

In embodiments, the ECL-labeled component is a detection reagent comprising an ECL label.

In embodiments, the invention provides a composition comprising about 1600 mM TEA, about 850 mM KCl, and about surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 1600 mM TEA, about 850 mM KCl, and about 1 surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 3200 mM TEA, about 850 mM KCl, and about 1 mM surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 3200 mM TEA, about 850 mM KCl, and about 1 mM surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 6400 mM TEA, about 850 mM KCl, and about surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 6400 mM TEA, about 850 mM KCl, and about 1 surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM LiCl, and about 1 mM surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 1200 mM TEA, about 850 mM LiCl, and about 1 mM surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1600 mM TEA, about 850 mM LiCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 1600 mM TEA, about 850 mM LiCl, and about 1 surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 3200 mM TEA, about 850 mM LiCl, and about 1 mM surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 3200 mM TEA, about 850 mM LiCl, and about 1 mM surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 6400 mM TEA, about 850 mM LiCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 6400 mM TEA, about 850 mM LiCl, and about 1 surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM NaCl, and about 1 mM PEG(18) tridecyl ether, wherein the composition has a pH of about 7.5. In embodiments, the invention provides a composition comprising about 1200 mM TEA, about 850 mM NaCl, and about 1 mM PEG(18) tridecyl ether, wherein the composition has a pH of about 7.8. In embodiments, the invention provides a composition comprising about 1600 mM TEA, about 850 mM NaCl, and about 1 mM PEG(18) tridecyl ether, wherein the composition has a pH of about 7.5. In embodiments, the invention provides a composition comprising about 1600 mM TEA, about 850 mM NaCl, and about 1 mM PEG(18) tridecyl ether, wherein the composition has a pH of about 7.8. In embodiments, the invention provides a composition comprising about 3200 mM TEA, about 850 mM NaCl, and about 1 mM PEG(18) tridecyl ether, wherein the composition has a pH of about 7.5. In embodiments, the invention provides a composition comprising about 3200 mM TEA, about 850 mM NaCl, and about 1 mM PEG(18) tridecyl ether, wherein the composition has a pH of about 7.8. In embodiments, the invention provides a composition comprising about 6400 mM TEA, about 850 mM NaCl, and about 1 mM PEG(18) tridecyl ether, wherein the composition has a pH of about 7.5. In embodiments, the invention provides a composition comprising about 6400 mM TEA, about 850 mM NaCl, and about 1 mM PEG(18) tridecyl ether, wherein the composition has a pH of about 7.8. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM KCl, and about 1 mM PEG(18) tridecyl ether, wherein the composition has a pH of about 7.5. In embodiments, the invention provides a composition comprising about 1200 mM TEA, about 850 mM KCl, and about 1 mM PEG(18) tridecyl ether, wherein the composition has a pH of about 7.8. In embodiments, the invention provides a composition comprising about 1600 mM TEA, about 850 mM KCl, and about 1 mM PEG(18) tridecyl ether, wherein the composition has a pH of about 7.5. In embodiments, the invention provides a composition comprising about 1600 mM TEA, about 850 mM KCl, and about 1 mM PEG(18) tridecyl ether, wherein the composition has a pH of about 7.8. In embodiments, the invention provides a composition comprising about 3200 mM TEA, about 850 mM KCl, and about 1 mM PEG(18) tridecyl ether, wherein the composition has a pH of about 7.5. In embodiments, the invention provides a composition comprising about 3200 mM TEA, about 850 mM KCl, and about 1 mM PEG(18) tridecyl ether, wherein the composition has a pH of about 7.8. In embodiments, the invention provides a composition comprising about 6400 mM TEA, about 850 mM KCl, and about 1 mM PEG(18) tridecyl ether, wherein the composition has a pH of about 7.5. In embodiments, the invention provides a composition comprising about 6400 mM TEA, about 850 mM KCl, and about 1 mM PEG(18) tridecyl ether, wherein the composition has a pH of about 7.8. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising about 1200 mM TEA, about 850 mM LiCl, and about 1 mM PEG(18) tridecyl ether, wherein the composition has a pH of about 7.5. In embodiments, the invention provides a composition comprising about 1200 mM TEA, about 850 mM LiCl, and about 1 mM PEG(18) tridecyl ether, wherein the composition has a pH of about 7.8. In embodiments, the invention provides a composition comprising about 1600 mM TEA, about 850 mM LiCl, and about 1 mM PEG(18) tridecyl ether, wherein the composition has a pH of about 7.5. In embodiments, the invention provides a composition comprising about 1600 mM TEA, about 850 mM LiCl, and about 1 mM PEG(18) tridecyl ether, wherein the composition has a pH of about 7.8. In embodiments, the invention provides a composition comprising about 3200 mM TEA, about 850 mM LiCl, and about 1 mM PEG(18) tridecyl ether, wherein the composition has a pH of about 7.5. In embodiments, the invention provides a composition comprising about 3200 mM TEA, about 850 mM LiCl, and about 1 mM PEG(18) tridecyl ether, wherein the composition has a pH of about 7.8. In embodiments, the invention provides a composition comprising about 6400 mM TEA, about 850 mM LiCl, and about 1 mM PEG(18) tridecyl ether, wherein the composition has a pH of about 7.5. In embodiments, the invention provides a composition comprising about 6400 mM TEA, about 850 mM LiCl, and about 1 mM PEG(18) tridecyl ether, wherein the composition has a pH of about 7.8. In embodiments, the composition is substantially free of an additional pH buffering component. In embodiments, the composition is substantially free of an additional component having a pKa of about 7.0 to about 8.0. In embodiments, the composition does not comprise any of Tris, phosphate, HEPES, glycylglycine, borate, acetate, citrate, POPSO, HEPPSO, and PIPES. In embodiments, the composition further comprises an ECL-labeled component. In embodiments, the ECL-labeled component is a detection reagent comprising an ECL label.

In embodiments, the invention provides a composition comprising: TEA, an ionic component, and optionally, one or both of an ECL-labeled component and a surfactant; wherein the composition has a pH of about 7.0 to about 8.0, and optionally, wherein the composition is substantially free of an additional pH buffering component. In embodiments, the composition comprises about 1000 mM to about 6500 mM of the TEA, and about 500 mM to about 2000 mM of the ionic component. In embodiments, the surfactant comprises an alkyl ether-PEG. In embodiments, the composition is substantially free of an additional pH buffering component. In embodiments, the composition consists essentially of or consists of the recited components.

In embodiments, the invention provides a composition comprising: TEA, an ionic component, and one or both of an ECL-labeled component and a surfactant; wherein the composition has a pH of about 7.0 to about 8.0, and optionally, wherein the composition is substantially free of an additional pH buffering component. In embodiments, the composition comprises about 1000 mM to about 6500 mM of the TEA, and about 500 mM to about 2000 mM of the ionic component. In embodiments, the surfactant comprises an alkyl ether-PEG. In embodiments, the composition is substantially free of an additional pH buffering component. In embodiments, the composition consists essentially of or consists of the recited components.

In embodiments, the invention provides a composition comprising: TEA, an ionic component, and optionally, one or both of an ECL-labeled component and a surfactant; wherein the composition has a pH of about 7.0 to about 8.0, and wherein the composition is substantially free of an additional pH buffering component. In embodiments, the composition comprises about 1000 mM to about 6500 mM of the TEA, and about 500 mM to about 2000 mM of the ionic component. In embodiments, the surfactant comprises an alkyl ether-PEG. In embodiments, the composition consists essentially of or consists of the recited components.

In embodiments, the invention provides a composition comprising: TEA, an ionic component, and an ECL-labeled component; wherein the composition has a pH of about 7.0 to about 8.0. In embodiments, the invention provides a composition comprising: TEA, an ionic component, and a surfactant; wherein the composition has a pH of about 7.0 to about 8.0. In embodiments, the invention provides a composition comprising: TEA, an ionic component, an ECL-labeled component, and a surfactant; wherein the composition has a pH of about 7.0 to about 8.0. In embodiments, the composition comprises about 1000 mM to about 6500 mM of the TEA, and about 500 mM to about 2000 mM of the ionic component. In embodiments, the surfactant comprises an alkyl ether-PEG. In embodiments, the composition is substantially free of an additional pH buffering component. In embodiments, the composition consists essentially of or consists of the recited components.

In embodiments, the composition provided herein is in dry form. In embodiments, the composition provided herein is in the form of a dry powder. In embodiments, the composition provided herein is a lyophilized powder. Throughout the present disclosure, when a composition comprises a certain concentration of its recited components (e.g., about 1000 mM to about 6500 mM of TEA; about 500 mM to about 2000 mM of ionic component; and/or about 0.1 mM to about 10 mM of surfactant) and/or a certain pH of its recited components (e.g., a pH of about 7.0 to about 8.0), it will be understood by one of ordinary skill in the art that the recited concentrations of the components and pH of the composition are in reference to the composition in liquid form, e.g., a dry composition reconstituted with a liquid diluent (e.g., water or aqueous assay buffer). In embodiments, the composition is in dry form and comprises the recited components at the recited concentrations when reconstituted with a liquid diluent. In embodiments, the composition is in dry form and comprises the recited pH when constituted with a liquid diluent.

Alkyl Diethanolamine/Zwitterionic Tertiary Amine Compositions

In embodiments, the invention provides a composition comprising about 50 mM to about 250 mM tBDEA, about 500 mM to about 1500 mM ionic component, and about 0.1 mM to about 10 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 50 mM to about 250 mM MDEA, about 500 mM to about 1500 mM ionic component, and about 0.1 mM to about 10 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 50 mM to about 250 mM DEA-PS, about 500 mM to about 1500 mM ionic component, and about 0.1 mM to about 10 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM MDEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™

X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM DEA-PS, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM ionic component, and about 1 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM MDEA, about 850 mM ionic component, and about 1 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM DEA-PS, about 850 mM ionic component, and about 1 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO-72-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM MDEA, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO-72-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM DEA-PS, about 700 mM to about 900 mM ionic component, and about 1 mM to about 5 mM surfactant, wherein the composition has a pH of about 7.0 to about 8.0; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO- (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 850 mM NaCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM MDEA, about 850 mM NaCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM DEA-PS, about 850 mM NaCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 850 mM KCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM MDEA, about 850 mM KCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM DEA-PS, about 850 mM KCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 850 mM LiCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM MDEA, about 850 mM LiCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM DEA-PS, about 850 mM LiCl, and about 1 mM to about 5 mM surfactant, wherein the composition has a pH of about 7.0 to about 8.0; wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 700 mM to about 900 mM ionic component, and about 1 mM surfactant, wherein the composition has a pH of about 7.0 to about 8.0; wherein the surfactant is 2-[4-(2,4,4-trimethylpentan-2-yl)phenoxy]ethanol (TRITON™ X-100). In embodiments, the invention provides a composition comprising about 100 mM to about 200 mM MDEA, about 700 mM to about 900 mM ionic component, and about 1 mM surfactant, wherein the composition has a pH of about 7.0 to about 8.0; wherein the surfactant is 2-[4-(2,4,4-trimethylpentan-2-yl)phenoxy]ethanol (TRITON™ X-100). In embodiments, the invention provides a composition comprising about 100 mM to about 200 mM DEA-PS, about 700 mM to about 900 mM ionic component, and about 1 mM surfactant, wherein the composition has a pH of about 7.0 to about 8.0; wherein the surfactant is 2-[4-(2,4,4-trimethylpentan-2-yl) phenoxyethanol (TRITON™ X-100). In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 700 mM to about 900 mM ionic component, and about 1 mM surfactant, wherein the composition has a pH of about 7.0 to about 8.0; wherein the ionic component is NaCl, KCl, or LiCl; and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 100 mM to about 200 mM MDEA, about 700 mM to about 900 mM ionic component, and about 1 mM surfactant, wherein the composition has a pH of about 7.0 to about 8.0; wherein the ionic component is NaCl, KCl, or LiCl; and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 100 mM to about 200 mM DEA-PS, about 700 mM to about 900 mM ionic component, and about 1 mM surfactant, wherein the composition has a pH of about 7.0 to about 8.0; wherein the ionic component is NaCl, KCl, or LiCl; and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 700 mM to about 900 mM ionic component, and about 1 mM surfactant, wherein the composition has a pH of about 7.0 to about 8.0; wherein the ionic component is NaCl, KCl, or LiCl; and wherein the surfactant is PEG(18) tridecyl ether. In embodiments, the invention provides a composition comprising about 100 mM to about 200 mM MDEA, about 700 mM to about 900 mM ionic component, and about 1 mM surfactant, wherein the composition has a pH of about 7.0 to about 8.0; wherein the ionic component is NaCl, KCl, or LiCl; and wherein the surfactant is PEG(18) tridecyl ether. In embodiments, the invention provides a composition comprising about 100 mM to about 200 mM DEA-PS, about 700 mM to about 900 mM ionic component, and about 1 mM surfactant, wherein the composition has a pH of about 7.0 to about 8.0; wherein the ionic component is NaCl, KCl, or LiCl; and wherein the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 700 mM to about 900 mM ionic component, and about 1 mM to about 5 mM surfactant, wherein the composition has a pH of about 7.5; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-PPO-72-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM tBDEA, about 700 mM to about 900 mM ionic component, and about 1 mM to about 5 mM surfactant, wherein the composition has a pH of about 7.8; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-PPO-72-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM MDEA, about 700 mM to about 900 mM ionic component, and about 1 mM to about 5 mM surfactant, wherein the composition has a pH of about 7.5; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-PPO-72-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM MDEA, about 700 mM to about 900 mM ionic component, and about 1 mM to about 5 mM surfactant, wherein the composition has a pH of about 7.8; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-PPO-72-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM DEA-PS, about 700 mM to about 900 mM ionic component, and about 1 mM to about 5 mM surfactant, wherein the composition has a pH of about 7.5; wherein the ionic component is NaCl, KCl, or LiCl; and wherein the surfactant is 2-[4-(2,4,4-trimethylpentan-2-yl) phenoxy ethanol (TRITON™ X-100), Poloxamer 407 (KOLLIPHOR® P-407), $PEO_{18}$-PPO- (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 100 mM to about 200 mM DEA-PS, about 700 mM to about 900 mM ionic component, and about 1 mM to about 5 mM surfactant, wherein the composition has a pH of about 7.8; wherein the ionic component is NaCl, KCl, or LiCl; and wherein the surfactant is 2-[4-(2,4,4-trimethylpentan-2-yl)phenoxy]ethanol (TRITON™ X-100), Poloxamer 407 (KOLLIPHOR® P-407), $PEO_{18}$-PPO-72-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the surfactant is PEG(18) tridecyl ether. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM tBDEA, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 150 mM MDEA, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM MDEA, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 150 mM DEA-PS, about 850 mM NaCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM DEA-PS, about 850 mM NaCl, and about 1 mM 2-[4-(2,4,4-trimethylpentan-2-yl)phenoxy]ethanol (TRITON™ X-100), wherein the composition has a pH of about 7.8. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM KCl, and about 1 mM 2-[4-(2,4,4-trimethylpentan-2-yl)phenoxy] ethanol (TRITON™ X-100), wherein the composition has a pH of about 7.5. In embodiments, the invention provides a composition comprising about 150 mM tBDEA, about 850 mM KCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 150 mM MDEA, about 850 mM KCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM MDEA, about 850 mM KCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 150 mM DEA-PS, about 850 mM KCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM DEA-PS, about 850 mM KCl, and about 1 mM 2-[4-(2,4,4-trimethylpentan-2-yl)phenoxy]ethanol (TRITON™ X-100), wherein the composition has a pH of about 7.8. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM LiCl, and about 1 mM 2-[4-(2,4,4-trimethylpentan-2-yl)phenoxy] ethanol (TRITON™ X-100), wherein the composition has a pH of about 7.5. In embodiments, the invention provides a composition comprising about 150 mM tBDEA, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 150 mM MDEA, about 850 mM LiCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM MDEA, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the invention provides a composition comprising about 150 mM DEA-PS, about 850 mM LiCl, and about 1 mM 2-[4-(2,4,4-trimethylpentan-2-yl)phenoxy]ethanol (TRITON™ X-100), wherein the composition has a pH of about 7.5. In embodiments, the invention provides a composition comprising about 150 mM DEA-PS, about 850 mM LiCl, and about 1 mM 2-[4-(2,4,4-trimethylpentan-2-yl)phenoxy]ethanol (TRITON™ X-100), wherein the composition has a pH of about 7.8. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM NaCl, and about 1 mM surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM tBDEA, about 850 mM NaCl, and about 1 mM surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM MDEA, about 850 mM NaCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM MDEA, about 850 mM NaCl, and about 1 surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM DEA-PS, about 850 mM NaCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM DEA-PS, about 850 mM NaCl, and about 1 surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM KCl, and about 1 mM surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM tBDEA, about 850 mM KCl, and about 1 mM surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM MDEA, about 850 mM KCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM MDEA, about 850 mM KCl, and about 1 surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM DEA-PS, about 850 mM KCl, and about surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM DEA-PS, about 850 mM KCl, and about 1 surfactant, wherein the composition has a pH of about 7.8, wherein the surfactant is Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM LiCl, and about 1 mM surfactant, wherein the composition has a pH of about 7.5, and wherein the surfactant is Poloxamer 407 (KOLLIPHOR® P-407), $PEO_{18}$-$PPO_{72}$-$PEO_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM tBDEA, about 850 mM LiCl, and about 1 mM surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM MDEA, about 850 mM LiCl, and about surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM MDEA, about 850 mM LiCl, and about 1 surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM DEA-PS, about 850 mM LiCl, and about surfactant, wherein the composition has a pH of about 7.5, and wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the invention provides a composition comprising about 150 mM DEA-PS, about 850 mM LiCl, and about 1 surfactant, wherein the composition has a pH of about 7.8, wherein the surfactant is Poloxamer 407 (KOLLIPHOR® P-407), PEO$_{18}$-PPO$_{72}$-PEO$_{18}$ (PLURONIC® P-123), PEG$_5$-PPG$_{68}$-PEG$_5$ (PLURONIC® L-121), PPO$_{26}$-PEO$_5$-PPO$_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, an alkyl ether-polyethylene glycol (PEG), or a combination thereof. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM NaCl, and about 1 mM PEG(18) tridecyl ether, wherein the composition has a pH of about 7.5. In embodiments, the invention provides a composition comprising about 150 mM tBDEA, about 850 mM NaCl, and about 1 mM PEG(18) tridecyl ether, wherein the composition has a pH of about 7.8. In embodiments, the invention provides a composition comprising about 150 mM MDEA, about 850 mM NaCl, and about 1 mM PEG(18) tridecyl ether, wherein the composition has a pH of about 7.5. In embodiments, the invention provides a composition comprising about 150 mM MDEA, about 850 mM NaCl, and about 1 mM PEG(18) tridecyl ether, wherein the composition has a pH of about 7.8. In embodiments, the invention provides a composition comprising about 150 mM DEA-PS, about 850 mM NaCl, and about 1 mM PEG(18) tridecyl ether, wherein the composition has a pH of about 7.5. In embodiments, the invention provides a composition comprising about 150 mM DEA-PS, about 850 mM NaCl, and about 1 mM PEG(18) tridecyl ether, wherein the composition has a pH of about 7.8. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM KCl, and about 1 mM PEG(18) tridecyl ether, wherein the composition has a pH of about 7.5. In embodiments, the invention provides a composition comprising about 150 mM tBDEA, about 850 mM KCl, and about 1 mM PEG(18) tridecyl ether, wherein the composition has a pH of about 7.8. In embodiments, the invention provides a composition comprising about 150 mM MDEA, about 850 mM KCl, and about 1 mM PEG(18) tridecyl ether, wherein the composition has a pH of about 7.5. In embodiments, the invention provides a composition comprising about 150 mM MDEA, about 850 mM KCl, and about 1 mM PEG(18) tridecyl ether, wherein the composition has a pH of about 7.8. In embodiments, the invention provides a composition comprising about 150 mM DEA-PS, about 850 mM KCl, and about 1 mM PEG(18) tridecyl ether, wherein the composition has a pH of about 7.5. In embodiments, the invention provides a composition comprising about 150 mM DEA-PS, about 850 mM KCl, and about 1 mM PEG(18) tridecyl ether, wherein the composition has a pH of about 7.8. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising about 150 mM tBDEA, about 850 mM LiCl, and about 1 mM PEG(18) tridecyl ether, wherein the composition has a pH of about 7.5. In embodiments, the invention provides a composition comprising about 150 mM tBDEA, about 850 mM LiCl, and about 1 mM PEG(18) tridecyl ether, wherein the composition has a pH of about 7.8. In embodiments, the invention provides a composition comprising about 150 mM MDEA, about 850 mM LiCl, and about 1 mM PEG(18) tridecyl ether, wherein the composition has a pH of about 7.5. In embodiments, the invention provides a composition comprising about 150 mM MDEA, about 850 mM LiCl, and about 1 mM PEG(18) tridecyl ether, wherein the composition has a pH of about 7.8. In embodiments, the invention provides a composition comprising about 150 mM DEA-PS, about 850 mM LiCl, and about 1 mM PEG(18) tridecyl ether, wherein the composition has a pH of about 7.5. In embodiments, the invention provides a composition comprising about 150 mM DEA-PS, about 850 mM LiCl, and about 1 mM PEG(18) tridecyl ether, wherein the composition has a pH of about 7.8. In embodiments, the composition further comprises about 100 mM to about 200 mM pH buffering component. In embodiments, the pH buffering component is Tris, phosphate, HEPES, glycylglycine, borate, acetate, citrate, or a combination thereof. In embodiments, the composition further comprises an ECL-labeled component. In embodiments, the ECL-labeled component is a detection reagent comprising an ECL label.

In embodiments, the invention provides a composition comprising an ECL coreactant, an ionic component, and a surfactant. In embodiments, the ECL coreactant is tributylamine (TBA), (dibutyl) aminoethanol (DBAE), (diethyl) aminoethanol (DEAE), triethanolamine (TEA), butyldiethanolamine (BDEA), propyldiethanolamine (PDEA), ethyldiethanolamine (EDEA), methyldiethanolamine (MDEA), tert-butyldiethanolamine (tBDEA), dibutylamine (DBA), butylethanolamine (BEA), diethanolamine (DEA), dibutylamine propylsulfonate (DBA-PS), dibutylamine butylsulfonate (DBA-BS), butylethanolamine propylsulfonate (BEA-PS), butylethanolamine butylsulfonate (BEA-BS), diethanolamine propylsulfonate (also known as 3-[Bis-(2-hydroxy-ethyl)-amino]-propane-1-sulfonic acid; DEA-PS), diethanolamine butylsulfonate (DEA-BS), or a combination thereof. In embodiments, the composition has a pH of about 7.0 to about 8.0. In embodiments, the composition further comprises a pH buffering component. Suitable ionic components (e.g., NaCl, KCl, and LiCl), surfactants (e.g., TRITON X-100 or mild surfactants described herein), pH buffering components (e.g., Tris or phosphate), and their concentrations in the compositions are provided herein. In embodiments, the composition further comprises an ECL-labeled component. In embodiments, the ECL-labeled component is a detection reagent comprising an ECL label.

Methods

In embodiments, the invention provides a method of generating electrochemiluminescence (ECL), comprising: (a) contacting an electrode with an ECL coreactant composition provided herein, (b) applying a voltage to the electrode; and (c) generating ECL. In embodiments, the ECL coreactant composition comprises TEA, tBDEA, MDEA, DEA-PS, or combination thereof. In embodiments, the invention provides a method of generating electrochemiluminescence (ECL), comprising: (a) contacting an electrode with a TEA composition comprising TEA; an ionic component; and optionally a surfactant; (b) applying a voltage to the electrode; and (c) generating ECL. In embodiments, the method further comprises detecting the generated ECL. In embodiments, the method further comprises measuring the generated ECL. In embodiments, the electrode is present on a surface.

In embodiments, the invention provides a method of generating electrochemiluminescence (ECL), comprising: (a) contacting an electrode with: (i) an ECL coreactant composition provided herein and (ii) an ECL label; (b) applying a voltage to the electrode; and (c) generating ECL. In embodiments, the ECL coreactant composition comprises TEA, tBDEA, MDEA, DEA-PS, or combination thereof. In embodiments, the invention provides a method of generating electrochemiluminescence (ECL), comprising: (a) contacting an electrode with: (i) a TEA composition comprising TEA, an ionic component, and optionally a surfactant; and (ii) an ECL label; (b) applying a voltage to the electrode; and (c) generating ECL. In embodiments, the method further comprises detecting the generated ECL. In embodiments, the method further comprises measuring the generated ECL, thereby quantifying the amount of the ECL label. In embodiments, the electrode is present on a surface.

In embodiments, the invention provides a method of quantifying the amount of an ECL label in a sample, comprising: (a) contacting an electrode with (i) an ECL coreactant composition provided herein or a TEA composition provided herein; and (ii) the sample comprising the ECL label; (b) applying a voltage to the electrode; (c) generating ECL; (d) measuring the ECL; and (e) quantifying the amount of the ECL label from the measured ECL. In embodiments, the ECL coreactant composition comprises TEA, tBDEA, MDEA, DEA-PS, or combination thereof. In embodiments, the TEA composition comprises TEA, an ionic component, and optionally a surfactant.

In embodiments, the ECL is generated from the reaction between the ECL coreactant (e.g., TEA, tBDEA, MDEA, and/or DEA-PS) in the compositions herein and the ECL label. In embodiments, the ECL label is present on an ECL-labeled component. In embodiments, the ECL label is present in a sample. In embodiments, the sample comprises the ECL-labeled component. In embodiments, the ECL-labeled component comprises a detection reagent. In embodiments, the sample comprises a binding partner of the ECL-labeled component. In embodiments, the ECL-labeled component comprises a binding partner of a detection reagent. Detection reagents and binding partners thereof are further described herein. In embodiments, the ECL-labeled component is present in a binding complex, and the method further comprises detecting the binding complex by detecting the generated ECL. In embodiments, the method comprises contacting the electrode with the sample that comprises a binding partner of the ECL-labeled component, wherein the ECL-labeled component and the binding partner form a binding complex, and the method further comprises detecting the binding complex by detecting the generated ECL. In embodiments, the method comprises measuring the generated ECL, thereby quantifying the amount of the ECL-labeled component and/or the binding complex.

In embodiments, each of the sample, the ECL coreactant composition or the TEA composition provided herein, and the ECL-labeled component is dry. In embodiments, In embodiments, each of the sample, the ECL coreactant composition or the TEA composition provided herein, and the ECL-labeled component is liquid. In embodiments, one or more of the sample, the ECL coreactant composition or the TEA composition provided herein, and the ECL-labeled component is dry, and the remaining component(s) is liquid. For example, the sample is liquid, and one or both of the ECL coreactant composition or the TEA composition provided herein and the ECL-labeled component are dry. In embodiments comprising a liquid component and a dry component, the liquid component reconstitutes the dry component. In embodiments, the method further comprises contacting the electrode with a liquid diluent, thereby reconstituting the dried component(s) in the liquid. In embodiments, the dried component(s) are present on the surface. In embodiments, the ECL coreactant composition is dry and present on the surface. In embodiments, the TEA composition is dry and present on the surface. In embodiments, the ECL-labeled component is dry and present on the surface. Compositions in dry form are described herein. In embodiments, the ECL-labeled component is a detection reagent that comprises an ECL label. In embodiments, the ECL coreactant composition comprises TEA, tBDEA, MDEA, DEA-PS, or combination thereof. In embodiments, the TEA composition comprises TEA, an ionic component, and optionally a surfactant.

In embodiments, the ECL-labeled component in the binding complex is a first copy of a detection reagent comprising the ECL label. In embodiments, the binding complex comprises the first copy of the detection reagent and a binding reagent immobilized on the surface. Binding reagents are further described herein. In embodiments, the method further comprises forming the binding complex. In embodiments, the binding complex is formed prior to or during step (a) of the method.

In embodiments, the binding complex is formed by incubating an assay mixture comprising the binding reagent, the first copy of the detection reagent, and a second copy of the detection reagent that comprises an ECL label, under conditions wherein the binding complex is formed on the surface, and the second copy of the detection reagent remains in solution. In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant.

In embodiments, the binding complex is formed by incubating an assay mixture comprising the binding reagent, the first copy of the detection reagent, a second copy of the detection reagent that comprises an ECL label, and an ECL coreactant composition or a TEA composition provided herein, under conditions wherein the binding complex is formed on the surface, and the second copy of the detection reagent remains in solution. In embodiments, the ECL coreactant composition comprises TEA, tBDEA, MDEA, DEA-PS, or combination thereof. In embodiments, the composition comprises TEA. In embodiments, the TEA composition comprises TEA, an ionic component, and optionally a surfactant.

In embodiments, the binding complex is formed by combining a sample with the first copy of the detection reagent, a second copy of the detection reagent that comprises an ECL label, and an ECL coreactant composition or a TEA composition provided herein, thereby forming an assay mixture; and contacting the assay mixture with the binding reagent, under conditions wherein the binding complex is formed on the surface, and the second detection reagent remains in solution. In embodiments, the ECL coreactant composition comprises TEA, tBDEA, MDEA, DEA-PS, or combination thereof. In embodiments, the composition comprises TEA. In embodiments, the TEA composition comprises TEA, an ionic component, and optionally a surfactant.

In embodiments, the binding complex further comprises an analyte. Analytes are further described herein. In embodiments, the binding reagent and the detection reagent each specifically binds to the analyte. In embodiments, the method comprises detecting the analyte by detecting the generated ECL. In embodiments, the method comprises measuring the generated ECL, thereby quantifying the amount of the analyte.

In embodiments, the ECL label comprises an electrochemiluminescent organometallic complex. In embodiments, the electrochemiluminescent organometallic complex comprises ruthenium, osmium, iridium, rhenium, and/or a lanthanide metal. In embodiments, the ECL label comprises ruthenium. In embodiments, the ECL label comprises ruthenium (II) tris-bipyridine.

In embodiments, the electrochemiluminescent organometallic complex comprises a substituted or unsubstituted bipyridine or a substituted or unsubstituted phenanthroline. In embodiments, the ECL label comprises a substituted bipyridine. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand comprising at least one sulfonate group is a compound of Formula I. In embodiments, the ECL label comprises a compound of Formula II.

In embodiments, the compositions herein are used in ECL-based binding assays, e.g., to detect and/or quantify an analyte of interest and/or a binding complex comprising an analyte. In embodiments, a binding complex is formed, e.g., on a surface comprising an electrode, and the binding complex comprises an ECL label capable of generating ECL when contacted with an ECL coreactant described herein. Binding assay formats include, but are not limited to: (1) direct binding assays, in which the analyte of interest is labeled with an ECL label, and a binding reagent, which is a binding partner of the analyte, is immobilized to the surface, and a binding complex is formed by direct binding of the binding reagent and the labeled analyte; (2) sandwich binding assays, in which an immobilized binding reagent and a detection reagent comprising an ECL label are both binding partners of the analyte, and the analyte binds the two binding partners to form the binding complex; (3) competitive binding assays, in which an immobilized binding reagent is a binding partner of the analyte, and a labeled detection reagent is a competitor (e.g., the analyte or a structural analogue of the analyte) that competes with the immobilized binding reagent for binding to the analyte, or, alternatively, the labeled detection reagent is a binding partner of the analyte, and the immobilized binding reagent is a competitor that competes with the detection reagent for binding to the analyte. In competitive binding assays, the labeled binding complex, formed by direct binding of the immobilized binding reagent and labeled detection reagent, decreases in quantity with increasing quantity of analyte. Binding assays are further described, e.g., in WO 2014/165061; WO 2014/160192; WO 2015/175856; U.S. Pat. Nos. 9,618,510; 10,114,015; 10,408,823; US 2017/0168047; and US 2019/0011441.

In embodiments, the invention provides a method for detecting a binding complex, comprising: (a) contacting a liquid sample with a surface comprising an ECL coreactant composition or a TEA composition provided herein, wherein the liquid sample comprises an ECL-labeled component; or wherein the liquid sample comprises a binding partner of an ECL-labeled component, and the method further comprises contacting the surface with the ECL-labeled component, thereby forming a binding complex on the surface that comprises the ECL-labeled component; (b) applying a voltage to the surface to generate ECL; and (c) detecting the generated ECL, thereby detecting the binding complex. In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant. In embodiments, the surface comprises an electrode. In embodiments, the ECL-labeled component comprises a detection reagent that comprises an ECL label. In embodiments, the ECL-labeled component comprises a detection reagent that comprises an ECL label, and the binding complex comprises a binding reagent and the detection reagent. In embodiments, the ECL-labeled component comprises a binding partner of a detection reagent, wherein the binding partner comprises an ECL label. In embodiments, the ECL-labeled component comprises a binding partner of a detection reagent, and the binding complex comprises a binding reagent, the detection reagent, and the binding partner. Detection reagents and binding partners are further described herein. In embodiments, the detection reagent and the ECL-labeled component comprise complementary oligonucleotides. In embodiments, the binding complex further comprises an analyte. In embodiments, the binding reagent and the detection reagent each specifically binds to the analyte.

In embodiments, the invention provides a method for detecting a binding complex, comprising: (a) contacting a liquid sample with a surface comprising an ECL-labeled component and an ECL coreactant composition or a TEA composition provided herein, wherein the liquid sample comprises a binding partner of an ECL-labeled component, thereby forming a binding complex on the surface that comprises the ECL-labeled component; (b) applying a voltage to the surface to generate ECL; and (c) detecting the generated ECL, thereby detecting the binding complex. In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant. In embodiments, the surface comprises an electrode. In embodiments, the ECL-labeled component comprises a detection reagent that comprises an ECL label. In embodiments, the ECL-labeled component comprises a detection reagent that comprises an ECL label, and the binding complex comprises a binding reagent and the detection reagent. In embodiments, the ECL-labeled component comprises a binding partner of a detection reagent, wherein the binding partner comprises an ECL label. In embodiments, the ECL-labeled component comprises a binding partner of a detection reagent, and the binding complex comprises a binding reagent, the detection reagent, and the binding partner. Detection reagents and binding partners are further described herein. In embodiments, the detection reagent and the ECL-labeled component comprise complementary oligonucleotides. In embodiments, the binding complex further comprises an analyte. In embodiments, the binding reagent and the detection reagent each specifically binds to the analyte.

In embodiments, the invention provides a method for detecting a binding complex, comprising: (a) forming a binding complex on a surface, and wherein the binding complex comprises an ECL-labeled component; (b) contacting the binding complex with an ECL coreactant composition or a TEA composition provided herein; (c) applying a voltage to the surface to generate ECL; and (d) detecting the generated ECL, thereby detecting the binding complex. In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant. In embodiments, the surface comprises an electrode. In embodiments, the ECL-labeled component comprises a detection reagent that comprises an ECL label. In embodiments, the ECL-labeled component comprises a detection reagent that comprises an ECL label, and the binding complex comprises a binding reagent and the detection reagent. In embodiments, the ECL-labeled component comprises a binding partner of a detection reagent, wherein the binding partner comprises an ECL label. In embodiments, the ECL-labeled component comprises a binding partner of a detection reagent, and the binding complex comprises a binding reagent, the detection reagent, and the binding partner. Detection reagents and binding partners are further described herein. In embodiments, the detection reagent and the ECL-labeled component comprise complementary oligonucleotides. In embodiments, the binding complex further comprises an analyte. In embodiments, the binding reagent and the detection reagent each specifically binds to the analyte.

In embodiments, the invention provides a method for detecting a binding complex, comprising: (a) forming a binding complex on a surface, wherein the surface comprises an electrode, and wherein the binding complex comprises a binding reagent immobilized on the surface and a detection reagent comprising an electrochemiluminescence (ECL) label; (b) contacting the binding complex with an ECL coreactant composition or a TEA composition provided herein; (c) applying a voltage to the surface to generate ECL; and (d) detecting the generated ECL, thereby detecting the binding complex. In embodiments, the binding complex further comprises an analyte, and the binding reagent and the detection reagent each specifically binds to the analyte. In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant. In embodiments, the binding complex further comprises an analyte. In embodiments, the binding reagent and the detection reagent each specifically binds to the analyte.

In embodiments, the invention provides a method for detecting an analyte of interest in a sample, comprising: (a) contacting the sample with: (i) a surface comprising a binding reagent, wherein the binding reagent specifically binds to the analyte; and (ii) a detection reagent that specifically binds to the analyte, wherein the detection reagent comprises an electrochemiluminescence (ECL) label, thereby forming a binding complex on the surface comprising the binding reagent, the analyte, and the detection reagent; (b) contacting the binding complex on the surface with an ECL coreactant composition or a TEA composition provided herein; (c) applying a voltage to the surface to generate ECL; and (d) detecting the generated ECL, thereby detecting the analyte. In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant. In embodiments, the surface comprises an electrode.

As discussed herein, the compositions provided herein can be used in an ECL-based assay that does not require a wash step. A "wash step," as used in the context of ECL-based assays conducted on a surface, refers to adding a wash buffer to the surface to remove undesired components from the assay reaction mixture, e.g., excess, non-specifically bound, or unbound reagents (e.g., detection reagent and/or ECL label) and/or unbound or non-specifically bound components of the sample. In an example, a biological sample can contain an analyte of interest and various other biological materials that are not of interest and do not bind specifically to the binding reagent, and a wash step can remove such components from the reaction mixture. In embodiments, the composition comprises TEA. In embodiments, the composition comprises TEA, an ionic component, and optionally a surfactant. In a "washed" assay, a wash step is typically used to remove unbound ECL labels prior to detecting the ECL labels on the surface. The wash step may be eliminated if the detection method can effectively discriminate between an ECL label bound to the surface (e.g., as part of a binding complex to be detected) or an unbound, "free" ECL label in solution. A "non-wash" assay format, which eliminates the wash step, is often advantageous because the washing step can be difficult or cumbersome to perform in many circumstances. However, a non-wash assay format is typically difficult to develop due to high background ECL signal from incomplete discrimination of free vs. bound ECL labels present in the reaction mixture. Even in assays employing a wash step, good discrimination between bound and free ECL label is advantageous because it provides greater robustness to inefficiencies or variations in the quality of a wash by providing tolerance to low levels of free label contamination that might be associated with a poor quality wash.

As discussed herein, the compositions herein surprisingly discriminated free vs. bound ECL labels in ECL-based assays conducted on solid surfaces (e.g., a solid electrode surface). In embodiments, the compositions herein increase the ratio of ECL signal from bound label to ECL signal from free label. Thus, the compositions herein provided improved assay performance, particularly when measuring low affinity interactions, which require the presence of the ECL label in high concentrations in the reaction, but would also be expected to suffer from significant signal loss due to binding complex dissociation during wash steps. In embodiments, the composition comprises TEA. In embodiments, the composition comprises TEA, an ionic component, and optionally a surfactant.

Without being bound by theory, it is believed that the compositions and ECL coreactants herein (e.g., TEA) decrease the distance from the solid electrode surface where ECL is generated from an ECL label. This, in turn, increases the signal of bound label (which is held in close proximity to the electrode) relative to free label (which is distributed throughout the solution above an electrode). The increased signal from bound label can also be characterized in terms of "effective excitation length," which is the maximum distance at which a free ECL label is able to be excited. The "effective excitation length" is impacted by: (1) the distance short-lived intermediates involved in the generation of ECL (e.g., oxidation product of the ECL coreactant) can diffuse from the electrode before they are depleted in a side reactions (a function of the lifetimes and diffusion constants for these intermediates); and (2) the rate at which free labels or unbound labeled reagents diffuse into the region close enough to the electrode to participate in a reaction with these reactive intermediates (a function of the diffusion constant for the unbound ECL labels or labeled reagents). In methods using the compositions herein, the effective excitation length is reduced by more than 2-fold, more than 3-fold, more than 4-fold, more than 5-fold, more than 9-fold, more than 7-fold, more than 8-fold, more than 9-fold, or more than 10-fold compared with a composition comprising TPA. In embodiments, the composition comprises TEA. In embodiments, the composition comprises TEA, an ionic component, and optionally a surfactant.

In embodiments, the method herein does not comprise a wash step. In embodiments where the method detects a binding complex, the method does not comprise a wash step prior to, during, or after forming a binding complex on a surface. In embodiments where the method detects an analyte of interest in a sample, the method does not comprise a wash step prior to, during, or after contacting the sample with (i) a surface comprising a binding reagent, wherein the binding reagent specifically binds to the analyte; and (ii) a detection reagent that specifically binds to the analyte. In embodiments, the method does not comprise a wash step prior to, during, or after contacting the binding complex with the composition. In embodiments, the method does not comprise a wash step prior to, during, or after a voltage to the surface to generate ECL. In embodiments, the method does not comprise a wash step prior to or during detecting the generated ECL. In embodiments, the composition comprises TEA. In embodiments, the composition comprises TEA, an ionic component, and optionally a surfactant.

In embodiments, the method herein comprises a wash step. In embodiments where the method detects a binding complex, the method comprises a wash step prior to, during, or after forming a binding complex on a surface. In embodiments where the method detects an analyte of interest in a sample, the method comprises a wash step prior to, during, or after contacting the sample with (i) a surface comprising a binding reagent, wherein the binding reagent specifically binds to the analyte; and (ii) a detection reagent that specifically binds to the analyte. In embodiments, the method comprises a wash step prior to, during, or after contacting the binding complex with the composition. In embodiments, the method comprises a wash step prior to, during, or after a voltage to the surface to generate ECL. In embodiments, the method comprises a wash step prior to or during detecting the generated ECL. In embodiments, the composition comprises TEA, tBDEA, MDEA, DEA-PS or a combination thereof.

In embodiments, the invention provides a method for detecting a binding complex, comprising: (a) forming an assay mixture by combining a sample with: (i) an ECL coreactant composition or a TEA composition provided herein; and (ii) a detection mixture comprising at least two copies of a detection reagent, wherein each copy of the detection reagent comprises an ECL label; (b) contacting the assay mixture with a binding reagent immobilized on a surface, wherein the surface optionally comprises an electrode, under conditions wherein (I) a binding complex is formed on the surface, the binding complex comprising the binding reagent and a first copy of the detection reagent; and (II) a second copy of the detection reagent remains in solution; (c) applying a voltage to the surface to generate ECL; and (d) detecting the generated ECL, thereby detecting the binding complex. In embodiments, the surface comprises an electrode. In embodiments, the second copy of the detection reagent is not removed prior to any of steps (b) to (d). In embodiments, the second copy of the detection reagent is not removed prior to step (b). In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant.

In embodiments, the invention provides a method for detecting a binding complex, comprising: (a) incubating an assay mixture comprising (i) a binding reagent immobilized on a surface, wherein the surface optionally comprises an electrode; and (ii) a detection mixture comprising at least two copies of a detection reagent, wherein each copy of the detection reagent comprises an electrochemiluminescence (ECL) label; under conditions wherein (i) a binding complex is formed on the surface, the binding complex comprising the binding reagent and a first copy of the detection reagent; and (ii) a second copy of the detection reagent remains in solution; (b) contacting the binding complex with an ECL coreactant composition or a TEA composition provided herein; (c) applying a voltage to the surface to generate ECL; and (d) detecting the generated ECL, thereby detecting the binding complex. In embodiments, the surface comprises an electrode. In embodiments, the method further comprises washing the surface prior to any of steps (b) to (d), thereby removing the second copy of the detection reagent. In embodiments, the second copy of the detection reagent is not removed prior to any of steps (b) to (d). In embodiments, the second copy of the detection reagent is not removed prior to step (b). In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant.

In embodiments, the invention provides a method for detecting a binding complex, comprising: (a) incubating an assay mixture comprising (i) a binding reagent immobilized on a surface, wherein the surface optionally comprises an electrode; (ii) a detection mixture comprising at least two copies of a detection reagent, wherein each copy of the detection reagent comprises an electrochemiluminescence (ECL) label; and (iii) an ECL coreactant composition or a TEA composition provided herein; under conditions wherein (i) a binding complex is formed on the surface, the binding complex comprising the binding reagent and a first copy of the detection reagent; and (ii) a second copy of the detection reagent remains in solution; (b) applying a voltage to the surface to generate ECL; and (c) detecting the generated ECL, thereby detecting the binding complex. In embodiments, the surface comprises an electrode. In embodiments, the method further comprises washing the surface prior to any of steps (b) or (c), thereby removing the second copy of the detection reagent. In embodiments, the second copy of the detection reagent is not removed prior to any of steps (b) or (d). In embodiments, the second copy of the detection reagent is not removed prior to step (b). In embodiments, the ECL coreactant composition comprises TEA, tBDEA, MDEA, DEA-PS, or combination thereof. In embodiments, the ECL coreactant composition comprises TEA. In embodiments, the TEA composition comprises TEA, an ionic component, and optionally a surfactant.

In embodiments, the binding complex further comprises an analyte, and the binding reagent and the first copy of the detection reagent each specifically binds to the analyte.

In embodiments, at least two copies of the binding reagent are immobilized on the surface, and wherein a first copy of the binding reagent forms a complex with the first copy of the detection reagent, and a second copy of the binding reagent binds to a competitor such that the second copy of the binding reagent does not form a complex with the second copy of the detection reagent. In embodiments, at least two copies of the binding reagent are immobilized on the surface, and wherein a first copy of the binding reagent forms a complex with the first copy of the detection reagent, and the second copy of the detection reagent binds to a competitor such that the second copy of the binding reagent does not form a complex with the second copy of detection reagent. Competitors and competitive assay formats are further described herein.

In embodiments, the binding reagent binds to the first copy of the detection reagent to form the binding complex.

In embodiments, the binding reagent comprises an antibody or antigen-binding fragment thereof, antigen, ligand, receptor, oligonucleotide, hapten, epitope, mimotope, or aptamer. In embodiments, the binding reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the binding reagent comprises at least one heavy or light chain complementarity determining region (CDR) of an antibody. In embodiments, the binding reagent comprises at least two CDRs from one or more antibodies. In embodiments, the binding reagent is an antibody or antigen-binding fragment thereof. In embodiments, the binding reagent specifically binds to the analyte. As used herein, "specifically binds" means that a reagent (e.g., the binding reagent) preferentially binds to its binding partner (e.g., an epitope of the analyte) relative to a random, unrelated substance. In embodiments, the binding reagent is an antibody or antigen-binding fragment thereof, comprising a binding domain that specifically binds to an epitope of the analyte.

In embodiments, the binding reagent is immobilized to a surface. In embodiments, the binding reagent is directly immobilized to the surface. In embodiments, the binding reagent is indirectly immobilized on the surface via secondary binding partners on the binding reagent and the surface. Exemplary secondary binding partners include, but are not limited to, complementary oligonucleotides, a receptor-ligand pair, an antigen-antibody pair, a hapten-antibody pair, an epitope-antibody pair, a mimotope-antibody pair, an aptamer-target molecule pair, hybridization partners, an intercalator-target molecule pair, cross-reactive moieties (such as, e.g., thiol and maleimide or iodoacetamide; aldehyde and hydrazide; or azide and alkyne or cycloalkyne).

In embodiments, the detection reagent comprises an antibody or antigen-detection fragment thereof, antigen, ligand, receptor, oligonucleotide, hapten, epitope, mimotope, or aptamer. In embodiments, the detection reagent is an antibody or a variant thereof, including an antigen/epitope-detection portion thereof, an antibody fragment or derivative, an antibody analogue, an engineered antibody, or a substance that binds to antigens in a similar manner to antibodies. In embodiments, the detection reagent comprises at least one heavy or light chain complementarity determining region (CDR) of an antibody. In embodiments, the detection reagent comprises at least two CDRs from one or more antibodies. In embodiments, the detection reagent is an antibody or antigen-detection fragment thereof. In embodiments, the detection reagent specifically binds to the analyte. In embodiments, the detection reagent is an antibody or antigen-binding fragment thereof, comprising a binding domain that specifically binds to an epitope of the analyte. In embodiments, the detection reagent binds to a different epitope of the analyte than the binding reagent. In embodiments, both the binding reagent and the detection reagent are antibodies or antigen-binding fragments thereof.

In embodiments, the detection reagent comprises an ECL label. In embodiments, the ECL label comprises an electrochemiluminescent organometallic complex. In embodiments, the organometallic complex comprises ruthenium, osmium, iridium, rhenium, and/or a lanthanide metal. In embodiments, the organometallic complex comprises a substituted or unsubstituted bipyridine or a substituted or unsubstituted phenanthroline. In embodiments, the ECL label comprises ruthenium. In embodiments, the ECL label comprises ruthenium (II) tris-bipyridine. In embodiments, the ECL label comprises a substituted bipyridine. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand comprising at least one sulfonate group is a compound of Formula I. In embodiments, the ECL label comprises a compound of Formula II. Exemplary ECL labels are provided in U.S. Pat. Nos. 5,714,089; 6,136,268; 6,316,607; 6,468,741; 6,479,233; 6,808,939; and 9,499,573.

In embodiments, the binding reagent and/or the detection reagent bind directly to the analyte. For example, the binding reagent and the detection reagent are each an antibody or antigen-binding fragment thereof that binds specifically to an epitope on the analyte. In embodiments, the binding reagent and/or the detection reagent indirectly bind the analyte via a secondary interaction. In embodiments, the analyte is linked to a binding partner of the binding reagent and/or the detection reagent. For example, the binding reagent and/or the detection reagent comprise streptavidin, and the analyte is linked to biotin. Further examples of binding partners that can be recognized through secondary interactions include, e.g., avidin-biotin, streptavidin-biotin, antibody-hapten, antibody-epitope tag, nucleic acid-complementary nucleic acid, aptamer-aptamer target, and receptor-ligand.

In embodiments, the surface comprises a multi-well plate. In embodiments, the surface comprises a particle. In embodiments, the surface comprises an assay cartridge. In embodiments, the surface comprises a surface of a slide, a chip, a well, an assay cell or a flow cell, a tube, a channel, a bead, or a microparticle. In embodiments, the surface comprises a particle, and the method further comprises collecting the particle on an additional surface, and applying the voltage to the particle on the additional surface. In embodiments, the particle is a bead (such as a magnetic bead), and the method further comprises collecting the bead(s) on a magnetized plate, wherein the plate comprises an electrode, and applying the voltage to the plate. In embodiments, the surface and/or additional surface comprises an electrode. In embodiments, the electrode is a carbon electrode, a platinum electrode, a gold electrode, or a silver electrode. In embodiments, the electrode is a carbon ink electrode.

In embodiments, the method comprises measuring the amount of an analyte of interest or a binding complex in a sample. Approaches to using a measured amount of ECL signal to determine the quantity and/or concentration of an ECL label (or an analyte or binding complex) in an ECL-based binding assay are known to one of ordinary skill in the art and include, for example, using a calibration standard and/or calibration curve to establish the relationship between ECL signal and quantity and/or concentration of the ECL label and/or analyte. Calibration may be performed at different times, for example, during development of a method, during qualification of a specific lot of assay materials, and/or at the time of an assay measurement. Calibration may also be performed using calculations based on the known physical and chemical behaviors of the assay components and instrumentation.

The methods herein can be used to test a variety of samples that may contain an analyte of interest. In embodiments, the sample is a biological sample. In embodiments, the sample is derived from a cell (live or dead), immortalized cell, cell-derived product, cell fragment, cell fraction, cell lysate (fractionated or unfractionated), eukaryotic cell, prokaryotic cell, organelle, cell nucleus and fractions thereof, cell membrane, hybridoma, cell culture supernatant (e.g., supernatant from an antibody-producing organism such as a hybridoma), cytoskeleton, protein complexes, structural biological components, skeletal components such as ligaments and tendons, hair, fur, feathers, hair fractions, skin, dermis, endodermis, mammalian fluid, secretion, excretion, whole blood, plasma, serum, sputum, lachrymal fluid, lymphatic fluid, synovial fluid, pleural effusion, urine, sweat, cerebrospinal fluid, ascites, milk, stool, bronchial lavage, saliva, amniotic fluid, nasal secretions, vaginal secretions, a surface biopsy, sperm, semen/seminal fluid, wound secretions and excretions, mucosal swabs, tissue aspirates, tissue homogenates, or an extraction, purification therefrom, or dilution thereof. In embodiments, the sample is derived from a plant, plant byproduct, soil, water source, oil, sewage, or environmental sample. In embodiments, the sample further comprises water, an organic solvent (e.g., acetonitrile, dimethyl sulfoxide, dimethyl formamide, n-methyl-pyrrolidone, alcohol, or combination thereof), EDTA, heparin, citrate, or combination thereof. Samples may be obtained from a single source described herein, or may contain a mixture from two or more sources.

Analytes that can be measured using the methods of the invention include, but are not limited to, whole cells, cell surface antigens, subcellular particles (e.g., organelles or membrane fragments), exosomes, extracellular vesicles, liposomes, membrane vesicles, viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample. Activities that may be measured include, but are not limited to, the activities of phosphorylases, phosphatases, esterases, trans-glutaminases, nucleic acid damaging activities, transferases, oxidases, reductases, dehydrogenases, glycosidases, ribosomes, protein processing enzymes (e.g., proteases, kinases, protein phosphatases, ubiquitin-protein ligases, etc.), nucleic acid processing enzymes (e.g., polymerases, nucleases, integrases, ligases, helicases, telomerases, etc.), cellular receptor activation, second messenger system activation, etc.

Whole cells may be animal, plant, or bacteria, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multi-enzyme complexes, and other particles which can be derived from living organisms. Nucleic acids include, for example, chromosomal DNA, plasmid DNA, viral DNA, and recombinant DNA derived from multiple sources. Nucleic acids also include RNA, for example messenger RNA, ribosomal RNA and transfer RNA. Polypeptides include, for example, enzymes, transport proteins, receptor proteins, and structural proteins such as viral coat proteins. In embodiments, the polypeptide is an enzyme or an antibody. In embodiments, the polypeptide is a monoclonal antibody. Hormones include, for example, insulin and T4 thyroid hormone. Pharmacological agents include, for example, cardiac glycosides. It is within the scope of this disclosure to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in this disclosure, but is meant only to illustrate the wide scope of the disclosure.

In embodiments, the method herein is a multiplexed method capable of detecting multiple binding complexes and/or analytes. In embodiments, the multiplexed method simultaneously detects multiple binding complexes and/or analytes. In embodiments, the multiplexed method comprises repeating one or more method steps to measure the multiple binding complexes and/or analytes. In embodiments, each of the method steps is performed for each binding complex and/or analyte in parallel. In embodiments where the method detects multiple binding complexes, each binding complex comprises a different binding and/or detection reagent. In embodiments where the method detects multiple analytes, each analyte binds to different binding and/or detection reagents. In embodiments, the binding of each analyte to its corresponding binding reagent is performed in parallel by contacting the surface(s) with a sample comprising multiple analytes.

In embodiments, the multiplexed method does not comprise a wash step. Multiplexed non-wash assays are particularly challenging due to the increased amount of detection reagent present in the assay mixture, and therefore increased amount of ECL label in solution, contributing to a high background ECL signal. The ECL coreactants herein had surprisingly good discrimination between bound ECL label and free ECL label in multiplexed assay formats, including multiplexed non-wash assays, providing high ECL signal and low background. In embodiments, the ECL coreactant is TEA.

In embodiments, the surface comprises a plurality of binding domains, and each binding complex is formed in a different binding domain. In embodiments, the plurality of binding domains is on a single surface. In embodiments, the surface comprises a multi-well plate, and each binding domain is in a different well. In embodiments, the surface comprises a well of a multi-well plate, and each binding domain is in a separate portion of the well. In embodiments, the plurality of binding domains is on one or more surfaces. In embodiments, the surface comprises a particle, and each binding domain is on a different particle. In embodiments, the particles are arranged in a particle array. In embodiments, the particles are coded to allow for identification of specific particles and distinguish between each binding domain.

In embodiments, each binding domain comprises a targeting agent capable of binding to a targeting agent complement, and each binding reagent comprises a supplemental linking agent capable of binding to a linking agent. In embodiments, the binding reagent is immobilized in the binding domain by: (1) binding the binding reagent, via the supplemental linking agent, to a targeting reagent complement connected to the linking agent; and (2) binding the product of (1) to the binding domain comprising the targeting agent, wherein (i) each binding domain comprises a different targeting agent, and (ii) each targeting reagent complement selectively binds to one of the targeting reagents, thereby immobilizing each binding reagent to its associated binding domain.

In embodiments, an optional bridging agent, which is a binding partner of both the linking agent and the supplemental linking agent, bridges the linking agent and supplemental linking agent, such that the binding reagents, each bound to its respective targeting agent complement, are contacted with the binding domains and bind to their respective targeting agents via the bridging agent, the targeting agent complement on each of the binding reagents, and the targeting agent on each of the binding domains.

In embodiments, the targeting agent and targeting agent complement are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the targeting agent and targeting agent complement are cross-reactive moieties, e.g., thiol and maleimide or iodoacetamide; aldehyde and hydrazide; or azide and alkyne or cycloalkyne. In embodiments, the targeting agent is biotin, and the targeting agent complement is avidin or streptavidin.

In embodiments, the linking agent and supplemental linking agent are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the linking agent and supplemental linking agent are cross-reactive moieties, e.g., thiol and maleimide or iodoacetamide; aldehyde and hydrazide; or azide and alkyne or cycloalkyne. In embodiments, the linking agent is avidin or streptavidin, and the supplemental linking agent is biotin. In embodiments, the targeting agent and targeting agent complement are complementary oligonucleotides. In embodiments, the targeting agent complement is streptavidin, the targeting agent is biotin, and the linking agent and the supplemental linking agent are complementary oligonucleotides.

In embodiments comprising a bridging agent, the bridging agent is streptavidin or avidin, and the linking agents and the supplemental linking agents are each biotin.

In embodiments, the invention provides a method for producing a composition comprising combining: an ECL coreactant, an ionic component, and a surfactant. In embodiments, the ECL coreactant is tributylamine (TBA), (dibutyl) aminoethanol (DBAE), (diethyl) aminoethanol (DEAE), triethanolamine (TEA), butyldiethanolamine (BDEA), propyldiethanolamine (PDEA), ethyldiethanolamine (EDEA), methyldiethanolamine (MDEA), tert-butyldiethanolamine (tBDEA), dibutylamine (DBA), butylethanolamine (BEA), diethanolamine (DEA), dibutylamine propylsulfonate (DBA-PS), dibutylamine butylsulfonate (DBA-BS), butylethanolamine propylsulfonate (BEA-PS), butylethanolamine butylsulfonate (BEA-BS), diethanolamine propylsulfonate (DEA-PS), or diethanolamine butylsulfonate (DEA-BS, also known as 3-[Bis-(2-hydroxy-ethyl)-amino]-propane-1-sulfonic acid).

In embodiments, the invention further provides a method for producing a composition comprising combining: triethanolamine (TEA) and an ionic component. In embodiments, the invention further provides a method for producing a composition comprising combining: triethanolamine (TEA), an ionic component, and a surfactant, wherein the method does not comprise adding an additional pH buffering component. In embodiments, one or more of the components is provided in dry form. Ionic components and surfactants suitable for the composition are provided herein and include, e.g., NaCl, KCl, and LiCl (for the ionic component), and Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis(propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, and an alkyl ether-polyethylene glycol (e.g., PEG(18) tridecyl ether) (for the surfactant). The TEA, ionic component, and surfactant can be included at the concentrations described herein. In embodiments, the composition produced by the method comprises about 1000 mM to about 6500 mM TEA, about 700 to about 1000 mM ionic component, and about 0.5 mM to about 10 mM surfactant. In embodiments, the composition produced by the method comprises about 1200 mM to about 1600 mM TEA, about 700 to about 1000 mM ionic component, and about 1 mM to about 5 mM surfactant.

In embodiments, the invention further provides a method for producing a composition comprising combining: tert-butyldiethanolamine (tBDEA), methyldiethanolamine (MDEA), 3-[Bis-(2-hydroxy-ethyl)-amino]-propane-1-sulfonic acid (DEA-PS), or a combination thereof; an ionic component; and a surfactant. In embodiments, one or more of the components is provided in dry form. Ionic components and surfactants suitable for the composition are provided herein and include, e.g., NaCl, KCl, and LiCl (for the ionic component), and Poloxamer 407 (KOLLIPHOR® P-407), $PEO_{18}$-$PPO_{72}$-$PEO_{18}$ (PLURONIC® P-123), $PEG_5$-$PPG_{68}$-$PEG_5$ (PLURONIC® L-121), $PPO_{26}$-$PEO_5$-$PPO_{26}$ (PLURONIC®31R1), ethylenediamine tetrakis (propoxylate-block-ethoxylate) tetrol (TETRONIC® 701), polyethylene glycol dodecyl ether (BRIJ® L4), polyethylene glycol hexadecyl ether (BRIJ® 58), polysorbate 20 (TWEEN® 20), 2,4,7,9-tetramethyl-d-decyne-4,7-diol ethoxylate, and an alkyl ether-polyethylene glycol (e.g., PEG(18) tridecyl ether) (for the surfactant). The tBDEA and/or MDEA, ionic component, and surfactant can be included at the concentrations described herein. In embodiments, the composition produced by the method comprises about 50 mM to about 250 mM tBDEA, about 50 mM to about 250 mM MDEA, and/or about 50 mM to about 250 mM DEA-PS, about 700 to about 1000 mM ionic component, and about 0.5 mM to about 10 mM surfactant.

Assay Module

In embodiments, the invention provides an assay module comprising a TEA composition in dry form, wherein the TEA composition comprises TEA, an ionic component, and optionally a surfactant. In embodiments, the invention provides an assay module comprising an ECL coreactant composition provided herein in dry form. In embodiments, the ECL coreactant composition comprises TEA, tBDEA, MDEA, DEA-PS, or combination thereof.

In embodiments, the assay module comprises a multi-well plate. In embodiments, the assay module comprises an assay cartridge. In embodiments, the assay module comprises a slide, a chip, a well, an assay cell or a flow cell, a tube, a channel, a bead, or a microparticle. In embodiments, the assay module comprises an electrode. In embodiments, the electrode is a carbon electrode, a platinum electrode, a gold electrode, or a silver electrode. In embodiments, the electrode is a carbon ink electrode.

In embodiments, the assay module further comprises a binding reagent in dry form. In embodiments, the assay module further comprises a detection reagent in dry form. In embodiments, the assay module further comprises a binding reagent and a detection reagent in dry form. Binding reagents and detection reagents are further described herein. In embodiments, the detection reagent comprises an ECL label.

In embodiments, the ECL label comprises an electrochemiluminescent organometallic complex. In embodiments, the organometallic complex comprises ruthenium, osmium, iridium, rhenium, and/or a lanthanide metal. In embodiments, the organometallic complex comprises a substituted or unsubstituted bipyridine or a substituted or unsubstituted phenanthroline. In embodiments, the ECL label comprises ruthenium. In embodiments, the ECL label comprises ruthenium (II) tris-bipyridine. In embodiments, the ECL label comprises a substituted bipyridine. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand comprising at least one sulfonate group is a compound of Formula I. In embodiments, the ECL label comprises a compound of Formula II.

Kits

In embodiments, the invention comprises a kit comprising an ECL coreactant composition or a TEA composition described herein. In embodiments, the ECL coreactant composition comprises an ECL coreactant selected from tributylamine (TBA), (dibutyl) aminoethanol (DBAE), (diethyl) aminoethanol (DEAE), triethanolamine (TEA), butyldiethanolamine (BDEA), propyldiethanolamine (PDEA), ethyldiethanolamine (EDEA), methyldiethanolamine (MDEA), tert-butyldiethanolamine (tBDEA), dibutylamine (DBA), butylethanolamine (BEA), diethanolamine (DEA), dibutylamine propylsulfonate (DBA-PS), dibutylamine butylsulfonate (DBA-BS), butylethanolamine propylsulfonate (BEA-PS), butylethanolamine butylsulfonate (BEA-BS), diethanolamine propylsulfonate (DEA-PS, also known as 3-[Bis-(2-hydroxy-ethyl)-amino]-propane-1-sulfonic acid), diethanolamine butylsulfonate (DEA-BS), and a combination thereof. In embodiments, the composition comprises TEA. In embodiments, the composition comprises tBDEA. In embodiments, the composition comprises MDEA. In embodiments, the composition comprises MDEA. In embodiments, the composition comprises DEA-PS. In embodiment, the TEA composition comprises TEA, an ionic component, and optionally a surfactant.

In embodiments, the invention provides a kit comprising two or more components that, when mixed, form a composition as described herein. In embodiments, the invention provides a kit comprising, in one or more containers, vials, or compartments: (a) triethanolamine (TEA) and (b) an ionic component. In embodiments, the invention provides a kit comprising, in one or more containers, vials, or compartments: (a) triethanolamine (TEA) and (b) an ionic component, wherein the kit does not comprise an additional pH buffering component. In embodiments, the invention provides a kit comprising, in one or more containers, vials, or compartments: (a) triethanolamine (TEA); (b) an ionic component; and (c) a surfactant, wherein the kit does not comprise an additional pH buffering component. Ionic components (e.g., NaCl, KCl, and/or LiCl), surfactants (e.g., TRITON X-100, KOLLIPHOR® P-407, PLURONIC® P-123, PLURONIC® L-121, PLURONIC®31R), TETRONIC® 701, BRIJ® L4, BRIJ® 58, TWEEN® 20, 2,4,7,9-tetramethyl-d-decyne-4,7-diol ethoxylate, and/or alkyl ether-polyethylene glycol (e.g., PEG(18) tridecyl ether)), and their concentrations are described herein.

In embodiments, the kit further comprises an assay reagent, a calibration reagent, a surface, an ECL label, or combination thereof. In embodiments, the kit comprises an assay reagent. In embodiments, the assay reagent comprises a binding reagent, a detection reagent, or both. Binding reagents and detection reagents are further described herein and include, e.g., antibody or antigen-binding fragment thereof, antigen, ligand, receptor, oligonucleotide, hapten, epitope, mimotope, or aptamer. In embodiments, the binding reagent is an antibody or antigen-binding fragment thereof. In embodiments, the detection reagent is an antibody or antigen-binding fragment thereof. In embodiments, both the binding reagent and the detection reagent are antibodies or antigen-binding fragments thereof.

In embodiments, the kit comprises an assay module described herein. In embodiments, the assay module comprises the ECL coreactant composition or TEA composition described herein in dry form. In embodiments, the kit comprises a surface. Surfaces suitable for performing the ECL-based binding assays are described herein. In embodiments, the surface comprises a multi-well plate. In embodiments, the surface comprises an assay cartridge. In embodiments, the surface comprises a particle. In embodiments, the surface comprises a surface of a slide, a chip, a well, an assay cell or a flow cell, a tube, a bead, or a microparticle. In embodiments where the surface comprises a particle, bead, or microparticle, the kit further comprises an additional surface, e.g., a plate, for collecting the particle, bead, or microparticle. In embodiments, the additional surface comprises a magnetically collectable particle, bead, or microparticle. In embodiments, the additional surface further comprises a magnetic plate. In embodiments, the surface and/or additional surface comprises an electrode. In embodiments, the electrode is a carbon electrode, a platinum electrode, a gold electrode, or a silver electrode. In embodiments, the electrode is a carbon ink electrode.

In embodiments, the binding reagent is immobilized on the surface. In embodiments, the binding reagent and the surface are provided separately in the kit, and the kit further comprises a reagent for immobilizing the binding reagent to the surface. Methods of immobilizing binding reagents to surfaces are provided herein and include, e.g., direct immobilization or indirect immobilization via secondary binding partners on the binding reagent and the surface.

In embodiments, the kit comprises an ECL label. ECL labels are further described herein and include, e.g., ruthenium-containing compounds. In embodiments, the ECL label comprises an electrochemiluminescent organometallic complex. In embodiments, the organometallic complex comprises ruthenium, osmium, iridium, rhenium, and/or a lanthanide metal. In embodiments, the organometallic complex comprises a substituted or unsubstituted bipyridine or a substituted or unsubstituted phenanthroline. In embodiments, the ECL label comprises ruthenium. In embodiments, the ECL label comprises ruthenium (II) tris-bipyridine. In embodiments, the ECL label comprises a substituted bipyridine. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand comprising at least one sulfonate group is a compound of Formula I. In embodiments, the ECL label comprises a compound of Formula II. In embodiments, the detection reagent comprises an ECL label. In embodiments, the detection reagent and the ECL label are provided separately in the kit, and the kit further comprises a reagent for conjugating the detection reagent to the ECL label. Methods of conjugation are known to one of skill in the art.

In embodiments, the kit comprises a calibration reagent. In embodiments, the calibration reagent comprises a known quantity of an analyte of interest. In embodiments, the calibration reagent comprises a known quantity of an ECL label. In embodiments, the kit comprises multiple calibration reagents comprising a range of concentrations of the analyte or the ECL label. In embodiments, the multiple calibration reagents comprise concentrations of the analyte or the ECL label near the upper and lower limits of quantitation for an ECL-based binding assay described herein. In embodiments, the multiple calibration reagents span the entire dynamic range of the binding assay. In embodiments, the calibration reagent is a positive control reagent. In embodiments, the calibration reagent is a negative control reagent. In embodiments, the positive or negative control reagent is used to provide a basis of comparison for the sample to be tested with the methods of the present invention.

In embodiments, one or more components of the kit is provided in dry form, e.g., as a lyophilized reagent. In embodiments, one or more components of the kit is provided in solution. In embodiments, the binding reagent is lyophilized. In embodiments, the binding reagent is provided in solution. In embodiments, the detection reagent is lyophilized. In embodiments, the detection reagent is provided in solution. In embodiments, the calibration reagent is lyophilized. In embodiments, the calibration reagent is provided in solution. In embodiments, the kit further comprises a liquid diluent. In embodiments, the liquid diluent reconstitutes a dry reagent. In embodiments, the liquid diluent is water. In embodiments, one or more components of the kits is provided as a concentrated stock solution, e.g., at 2×, 4×, 5×, 10×, or 20× the working concentration of the reagent.

In embodiments, the kit comprises an assay instrument, e.g., to detect ECL generated from the compositions and methods described herein. In embodiments, the kit further comprises an assay consumable, e.g., an assay module configured to contain samples and/or reagents during one or more steps of the method described herein, pipette tips and other consumables for transferring liquid samples and reagents, covers and seals for assay modules and other consumables used in an assay (e.g., tubes, cuvettes, wells, multi-well plates, cartridges, lateral flow devices, flow cells), racks for holding other assay consumables, labels (including human readable or machine readable formats such as barcodes, RFIDs, etc.) for identifying samples, or other assay consumables and media (including paper and electronic media) for providing information about the method and/or instructions for performing the method.

All references cited herein, including patents, patent applications, papers, textbooks and the like, and the references cited therein, to the extent that they are not already, are hereby incorporated herein by reference in their entirety.

EXAMPLES

Example 1. Assessment of Zwitterion and Hydroxyethyl Amine ECL Coreactants

The following list of ECL coreactants were tested for their ECL generation and ability to discriminate between surface-bound and free (in solution) ECL labels in a solid-surface ECL assay: tributylamine (TBA), (dibutyl) aminoethanol (DBAE), (diethyl) aminoethanol (DEAE), triethanolamine (TEA), butyldiethanolamine (BDEA), propyldiethanolamine (PDEA), ethyldiethanolamine (EDEA), methyldiethanolamine (MDEA), tert-butyldiethanolamine (tBDEA), dibutylamine (DBA), butylethanolamine (BEA), diethanolamine (DEA), dibutylamine propylsulfonate (DBA-PS), dibutylamine butylsulfonate (DBA-BS), butylethanolamine propylsulfonate (BEA-PS), butylethanolamine butylsulfonate (BEA-BS), diethanolamine propylsulfonate (DEA-PS), and diethanolamine butylsulfonate (DEA-BS). Each ECL read buffer composition was prepared with 150 mM of a specified ECL coreactant, 200 mM phosphate, 850 mM NaCl, and either TRITON™ X-100 ("TX100") or PEG(18) tridecyl ether ("PEG$_{18}$ TDE") and adjusted to pH 7.5.

Figures 1A, 1B:
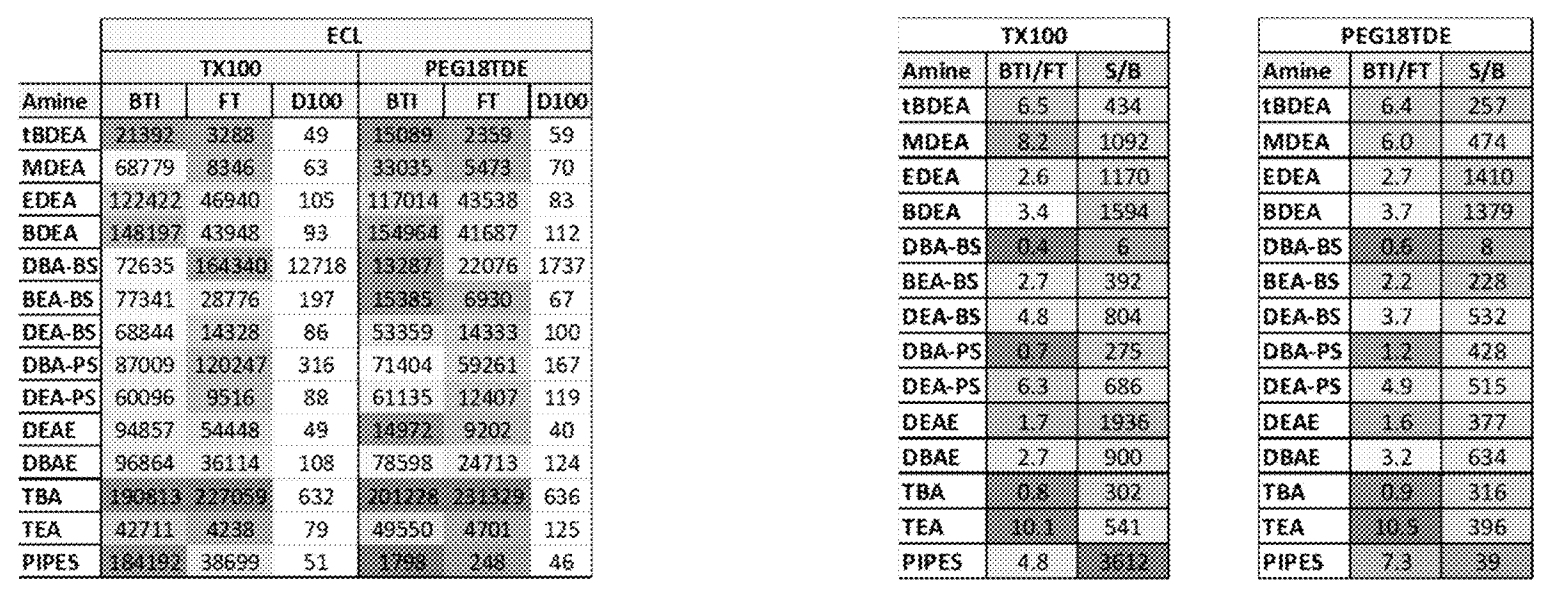

2 nM of IgG conjugated with biotin and an ECL label ("BTI") was used as the control for bound label and contacted with an electrode surface coated with streptavidin. 500 mM of free ECL label ("FT") was used as the control for free label. Results are shown in FIGS. 1A and 1B. FIG. 1A shows the ECL signal measured with BTI, FT, and background signal ("D100") with ECL read buffer only (no label). FIG. 1B shows the ratio of ECL signal from bound label to ECL signal from free label ("BTI/FT"), and the signal-to-background ratio ("S/B").

The raw values and ratios in FIGS. 1A and 1B present information regarding radical lifetimes, excited state formation efficiency for both oxidizing and reducing pathways, and ECL label-excited state reductive/oxidative quenching efficiency. The ECL signal sensitivity in TRITON™ X-100 supports a short-lived amine radical cation or low electron transfer efficiency to the ECL label in-1 oxidation state (Label-1).

From the results, it can be concluded that DBA-BS is sensitive to TRITON™ X-100, producing significantly more signal from free label than from bound label, which suggests a long-lived reducing radical was being produced leading to efficient reduction of the free ECL label. Moreover, the BTI/FT signal ratio of MDEA was higher than PIPES, an ECL coreactant known to have a short radical cation lifetime, and MDEA has a reasonable signal-to-background ratio but only in the presence of TRITON™ X-100, suggesting that MDEA also has a short radical cation lifetime. BDEA showed a strong signal from BTI and intermediate amount of signal from FT, suggesting a radical cation and reducing radical lifetimes in between those of TBA and TEA. Notably, TEA displayed a very low FT signal and reasonably high BTI signal, was insensitive to the presence or absence of TRITON™ X-100, and had the highest BTI/FT ratio of all the tested ECL coreactants.

Example 2. Bound/Free Label Signal Ratios Vs. TEA Concentration

TEA has the ability to serve as both pH buffer and ECL coreactant due to its pKa of 7.7. Varying concentrations of TEA between 50 mM and 1600 mM were tested for their ECL generation properties. Each ECL read buffer composition tested contained TEA at a specified concentration and 850 mM NaCl, pH 7.8. The compositions were tested with BTI and FT labels in the same manner as for Example 1.

Results are shown in FIGS. 2A-2C. FIG. 2A shows a plot of the ECL generated from BTI and FT, and the BTI/FT ratio with varying concentration of TEA. The dashed lines at the top and bottom of the plot indicate the BTI signal and BTI/FT ratio, respectively, generated with a PIPES ECL read buffer. Thus, TEA shows a peak BTI/FT ratio at around 1200 mM concentration, and at TEA concentrations greater than 1200 mM, BTI signal was within 10 to 25% of PIPES ECL read buffer. The TEA radical cation and reducing radical lifetimes, and changes in buffer viscosity may have contributed to the general BTI/FT behavior and apparent decline at 1600 mM TEA. FIG. 2B shows the measured ECL signals from BTI, FT, and background (D100) with varying concentrations of TEA, and FIG. 2C shows the BTI/FT ratio, S/B ratio, and percent ECL generation compared with PIPES ECL read buffer.

Example 3. ECL Signal Vs. Coreactant Concentration

The results of Example 2 suggested that increasing concentration of TEA produces higher ECL signal, which were contrary to the predictions based on the known behaviors of other ECL coreactants, such as PIPES. The ECL signal generated with a PIPES ECL read buffer and TEA ECL read buffer were measured at varying concentrations of the coreactants. The PIPES compositions contained 20 mM, 40 mM, or 80 mM PIPES, >0.1% TRITON™ X-100, and 80 to 320 mM potassium phosphate buffer pH 7.5. The TEA compositions contained 50 mM, 100 mM, or 200 mM TEA, 850 mM NaCl, and 1 mM PEG18 TDE. The compositions were tested with BTI as described for the previous Examples.

Figure 3B:
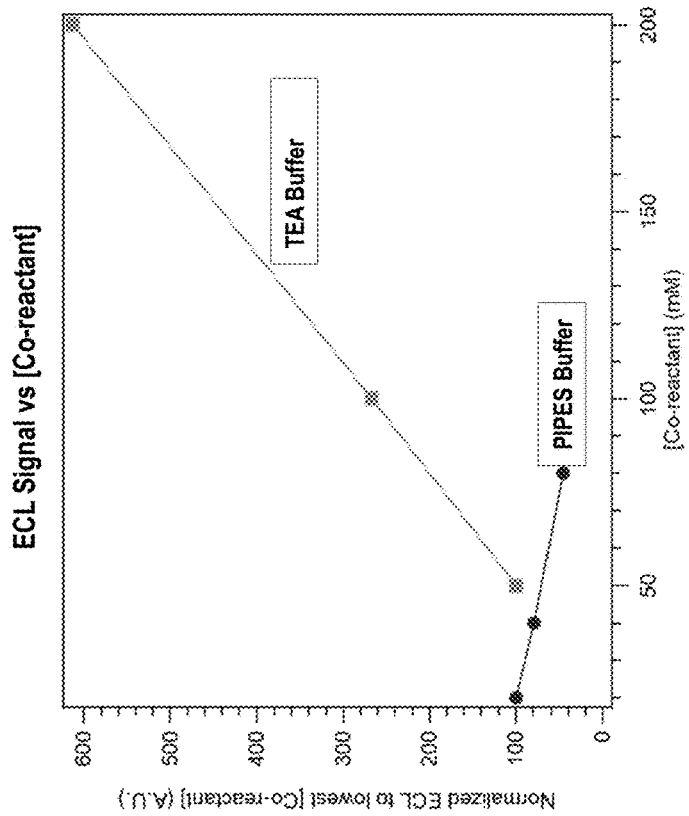
FIGS. 3A and 3B relate to Example 3 and show the results of an embodiment of an ECL-based assay.
Figure 3A:
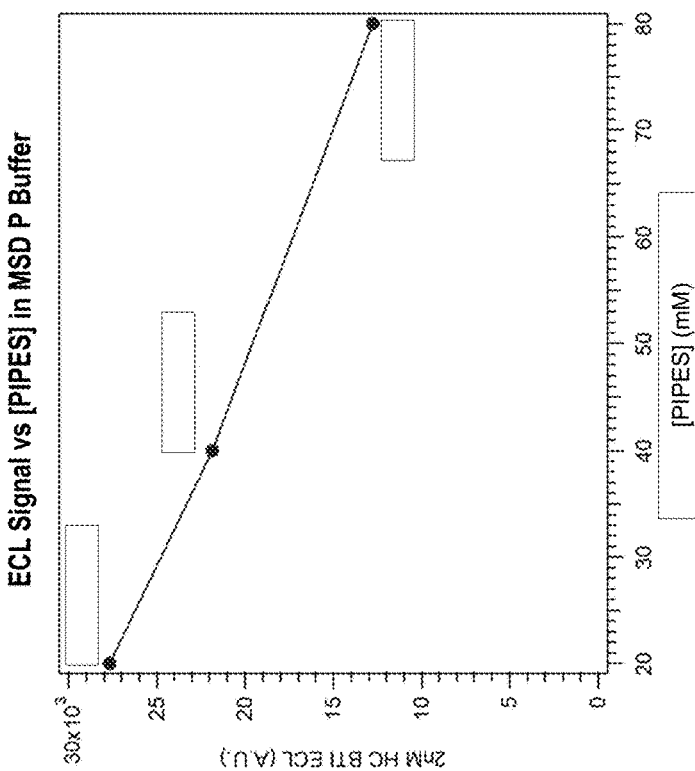

Results are shown in FIGS. 3A (ECL signal vs. PIPES concentration) and 3B (relative ECL signal vs. PIPES concentration and TEA concentration plotted together). FIG. 3A confirms that for PIPES ECL read buffer increasing PIPES concentration decreased the ECL signal. FIG. 3B shows the unexpected contrasting behavior of TEA, which showed a strong increase in ECL signal with increasing TEA concentration despite having short radical lifetimes.

Example 4. Different Assay Formats

FIGS. 4A-4D illustrate four different assay formats, tested with ECL read buffers containing different ECL coreactants: TPA, BDEA, PIPES, and 1.2 M TEA. The assays were assessed with a panel of analytes. FIGS. 4E-4H illustrate multiplexed versions of the assays in FIGS. 4A-4D.

Figure 4A:
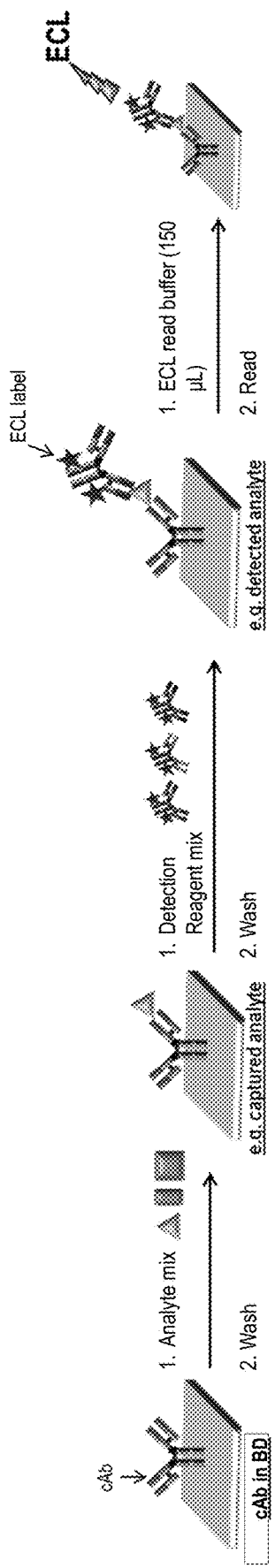
FIGS. 4A-4H illustrate embodiments of ECL-based assays described herein and are further described in Example 4.

FIG. 4A illustrates a "standard" 2-step washed assay, wherein a capture antibody ("cAb"; binding reagent) immobilized on a binding domain ("BD") on a surface is contacted with a mixture of analytes, one of which binds specifically to the capture antibody, and the surface is then washed, resulting in the analyte captured on the surface. A mixture of detection antibodies ("dAb"; detection reagent), each containing an ECL label and one of which binds specifically to the analyte, is then added to the surface, and the surface is then washed, resulting in a binding complex comprising the cAb, analyte, and dAb. ECL read buffer is then added to the surface, and the generated ECL is then read by an ECL reader instrument. FIG. 4E illustrates a multiplexed version of the "standard" 2-step washed assay, wherein one or more surfaces comprises a plurality of binding domains, each binding domain comprising a capture antibody that can bind to an analyte in the analyte mix. The surface(s) comprising the binding domains is washed after adding the analyte mix, resulting in a plurality of analytes captured on the binding domains. A mixture of detection antibodies, each containing an ECL label and can bind to an analyte in the analyte mix, is then added to the surface(s), and the surface is then washed, resulting in a plurality of binding complexes, each binding complex comprising a cAb, analyte, and dAb. ECL read buffer is then added to the surface, and the generated ECL is read by an ECL instrument.

In the Examples herein using the standard 2-step assay format, 50 µL of an analyte mix was added to plates, shaken for 2 hours at 705 rpm and room temperature. The plates were washed once with wash buffer, and 25 µL of the detection antibody mix was added to the plates, shaken for 1.5 hours at 705 rpm and room temperature. The plates were washed once with wash buffer, and 150 µL of ECL read buffer was added to the plates. The plates were then read with an ECL reader instrument.

Figure 4B:
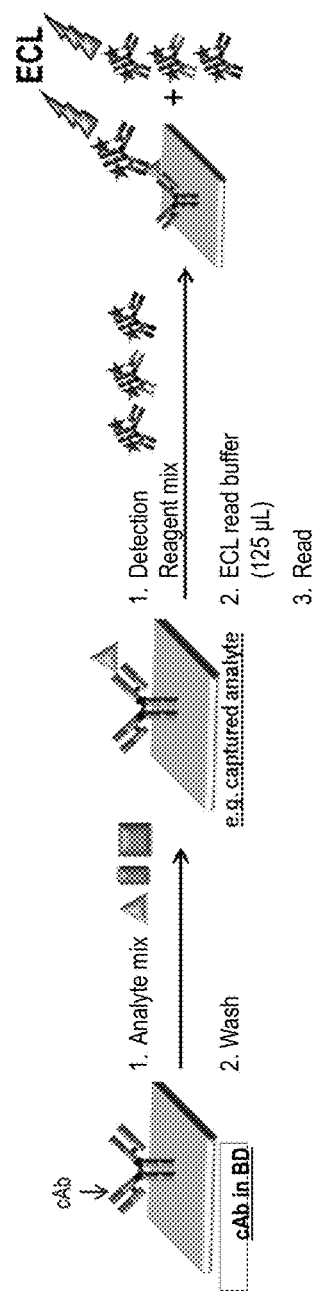

FIG. 4B illustrates a "1-step" assay, wherein a capture antibody on a binding domain on a surface is contacted with an analyte mix, and the surface is then washed as in FIG. 4A. The detection antibody mix is then added, followed by the ECL read buffer without washing in-between adding the detection antibody mix and the ECL read buffer. The generated ECL is then read by an ECL reader instrument. FIG. 4F illustrates a multiplexed version of the "1-step" assay, wherein one or more surfaces comprises a plurality of binding domains, each binding domain comprising a capture antibody that can bind to an analyte in the analyte mix. The surface(s) comprising the binding domains is washed after adding the analyte mix as in FIG. 4E. The detection antibody mix is added to form a plurality of binding complexes, and ECL read buffer is then added without washing in between adding the detection antibody mix and the ECL read buffer. The generated ECL is then read by an ECL reader instrument.

In the Examples herein using the 1-step assay format, 50 µL of an analyte mix was added to plates, shaken for 2 hours at 705 rpm and room temperature. The plates were washed once with wash buffer, and 25 µL of the detection antibody mix was added to the plates, shaken for 1.5 hours at 705 rpm and room temperature. 125 µL of ECL read buffer was added to the plates. The plates were then read with an ECL reader instrument.

Figure 4C:
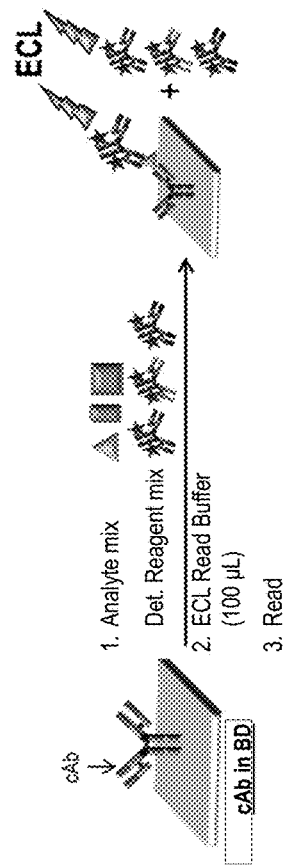

FIG. 4C illustrates a "1-step non-wash" assay, wherein a capture antibody on a binding domain on a surface is contacted with: an analyte mix and detection antibody mix, followed by the ECL read buffer without washing in between any of the steps. The generated ECL is then read by an ECL reader instrument. FIG. 4G illustrates a multiplexed version of the "1-step non-wash" assay, wherein one or more surfaces comprises a plurality of binding domains, each binding domain comprising a capture antibody that can bind to an analyte in the analyte mix. The surface(s) comprising the binding domains is contacted with an analyte mix and detection antibody mix to form a plurality of binding complexes, then ECL read buffer is added without washing in between any of the steps. The generated ECL is then read by an ECL reader instrument.

In the Examples herein using the 1-step non-wash assay format, 25 µL of an analyte mix was added to plates, followed by 25 µL of the detection antibody mix, then shaken for 2 hours at 705 rpm and room temperature. 100 µL of ECL read buffer was added to the plates. The plates were then read with an ECL reader instrument.

Figure 4D:
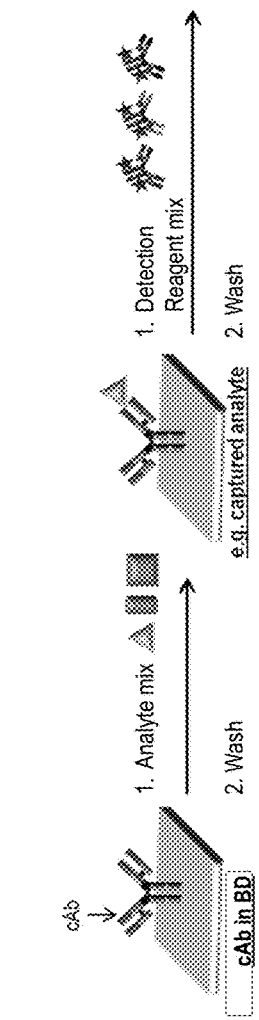
Figure 4E:
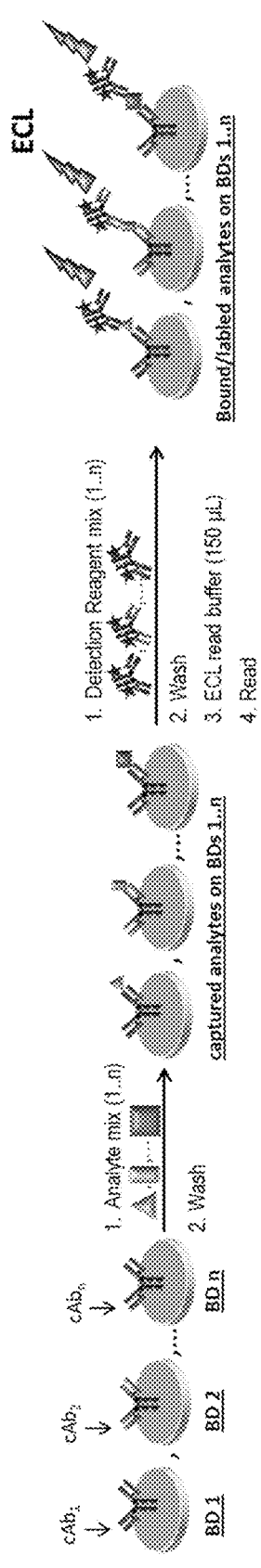
Figure 4F:
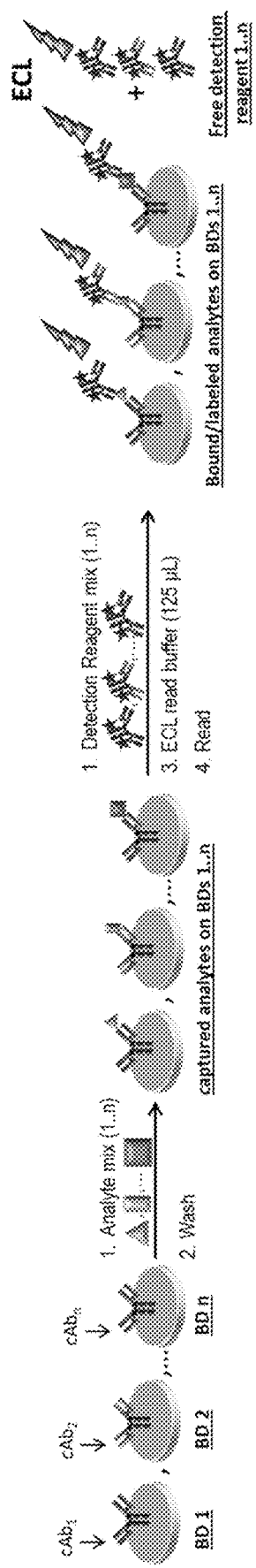
Figure 4G:
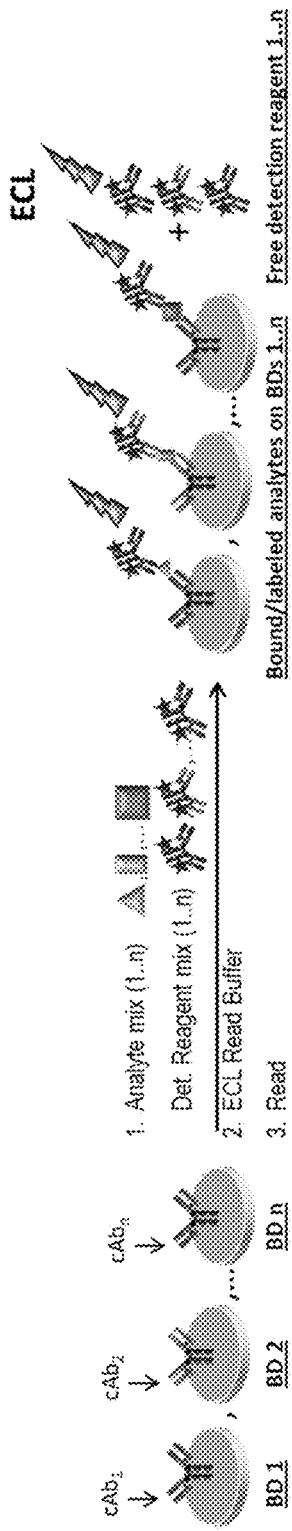
Figure 4H:
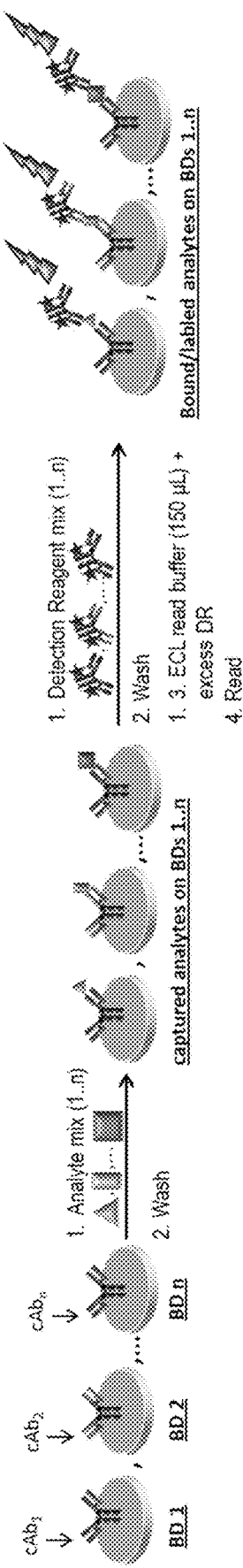

FIG. 4D illustrates a "mock ECL label" assay, wherein a capture antibody on a surface is contacted with an analyte mix, the surface is washed, a detection antibody mix is added, and the surface is optionally washed again, resulting in a binding complex as in FIG. 4A. The ECL read buffer is then added to the surface along with a detection antibody that comprises an ECL label and that does not bind to any component of the binding complex on the surface, which serves as a proxy for "free" ECL label in solution. The generated ECL is then read by an ECL reader instrument. FIG. 4H illustrates a multiplexed version of the "mock ECL label" assay, wherein one or more surfaces comprises a plurality of binding domains, each binding domain comprising a capture antibody that can bind to an analyte in the analyte mix. The surface(s) comprising the binding reagents is contacted with an analyte mix, the surface is washed, a detection antibody mix is added, and the surface is optionally washed again, resulting in a plurality of binding complexes as in FIG. 4E. The ECL read buffer is then added to the surface along with a detection antibody that comprises an ECL label and that does not bind to any component of the binding complex on the surface, which serves as a proxy for "free" ECL label in solution. The generated ECL is then read by an ECL reader instrument.

In the Examples herein using the mock ECL label assay format, 50 µL of an analyte mix was added to plates, shaken for 2 hours at 705 rpm and room temperature. The plates were washed once with wash buffer, and 25 µL of the detection antibody mix was added to the plates, shaken for 1.5 hours at 705 rpm and room temperature. The plates were washed once with wash buffer, and 150 µL of ECL read buffer containing excess detection reagent was added to the plates. The plates were then read with an ECL reader instrument.

Example 5A. Assessment of ECL Read Buffers in Different Assay Formats

In Example 5A, the standard 2-step, 1-step, and mock ECL label multiplexed assay formats (shown in FIGS. 4E, 4F, and 4H) were tested. Read buffer was diluted ⅝th the 1-step assay. Results of the specific ECL signals and non-specific binding (NSB) for these assays are shown in FIG. 5A, and the lowest limits of detection (LLOD) are shown in FIG. 5B. The specific ECL signal from TEA read buffer did not change significantly in a 1-step assay as compared with the standard 2-step assay. TEA had significantly improved performance over PIPES read buffer in the 1-step assay, due to increased specific signal and decreased NSB. Some elevation in background was observed across all ECL read buffers in the "mock ECL-label" assay, due to the high concentration of free detection antibody-ECL label in solution. TEA read buffer showed the best performance among the buffers in this assay format because of its excellent discrimination of bound vs. free label. Specific ECL signal for bound label from TEA read buffer was generally within 2× of the BDEA read buffer formulations, and thus the improved surface selectivity came with only minimal cost in overall signal generation.

In the standard 2-step assay, the LLOD of TEA read buffer was within 2- to 3-fold of the LLOD of a commercially available tripropylamine (TPA) read buffer. The ordering of average LLOD for the 1-step assay across different read buffers was as follows: TPA>BDEA>PIPES>TEA, with TEA providing the best (lowest) LLOD.

FIG. 5C shows a relative comparison of the signal in the presence of analyte (ECL) and in the absence of analyte (NSB) presented in FIG. 5A, with all ECL read buffers and assay formats normalized to the results obtained with a commercial TPA formulation in the standard 2-step assay format. In general, PIPES read buffer showed lower ECL signal than TEA read buffer across all assay formats, which is the inverse of the ECL generation efficiency data, suggesting that PIPES performance is possibly negatively affected by the immobilization of antibodies on the electrode surface or by exposure of the electrode to the sample matrices or diluents used during the assay. TEA and PIPES showed the lowest relative change in NSB signal between the standard 2-step and 1-step assay formats.

FIG. 5D shows the comparison of signal to background (S/B) and signal to noise (S/N) ratio across all ECL read buffers and assay formats. On average, TEA showed the smallest change in S/B between standard 2-step and 1-step assay formats. The average S/N ratios changed the least for TEA read buffer between all three assay formats. Thus, TEA read buffer demonstrated significant potential for use in non-wash assay formats.

Example 5B. Assessment of ECL Read Buffers in Different Assay Formats

In Example 5B, the standard 2-step, 1-step, and 1-step non-wash multiplexed assay formats (shown in FIGS. 4E, 4F, and 4G) were tested. Read buffer was diluted ⅝th in the 1-step assay, and $\frac{2}{3}^{rd}$ in the 1-step non-wash assay. Results of the specific ECL and NSB for these assays are shown in FIG. 6A, and the LLOD are shown in FIG. 6B. The specific ECL signal from TEA read buffer did not change significantly in the 1-step non-wash assay across most analytes, despite the $\frac{2}{3}^{rd}$ buffer dilution in the 1-step non-wash assay. There was also little to no NSB change for TEA read buffer in the 1-step non-wash assay vs. 1-step assay, likely due to the $\frac{2}{3}^{rd}$ dilution of the TEA read buffer, which causes a ~30% decrease in ECL generation efficiency. PIPES read buffer performed significantly worse than TEA read buffer in the 1-step assay (as also observed in Example 4A) due to decreased specific ECL signal and increased NSB signal. In general, TEA read buffer LLOD was within 5× of TPA read buffer and BDEA read buffers in the standard 2-step assay format.

FIG. 6C shows a relative comparison of ECL and NSB results from FIG. 6A, with all ECL read buffers and assay formats normalized to the results obtained with TPA formulation in the standard 2-step assay format. On average, TEA read buffer showed little change in specific ECL and NSB between the 1-step assay and 1-step non-wash assay (with the exceptions being the analytes IL-1B, IL-8, and TNF-α, which showed a similar signal loss with the other ECL read buffers, suggesting that the issue is not related to the ECL coreactant but possibly with the 1-step analyte capture and/or binding complex formation steps). The poor performance of PIPES read buffer in the 1-step and 1-step non-wash assay formats is likely due to dilution of TRITON™ X-100 and possibly sensitivity of ECL generation in the presence of PIPES to effects of the assay conditions and the condition of the electrode surface.

Example 6. Evaluation of TEA Read Buffer with Common Sample and Diluent Matrices TEA read buffer ECL generation and background were tested with different sample matrices and metabolite and/or drug interferents. The TEA read buffer composition included 1.2 M TEA and 850 mM NaCl at pH 7.8. Surfaces were contacted with 2 nM BTI. The assays were conducted as shown in FIG. 4C (1-step non-wash assay), with the sample matrices (with or without interferents) added just prior to adding the ECL read buffer. FIG. 7A shows the sample matrices, and FIG. 7B shows the interferents tested.

Figures 8A, 8B:
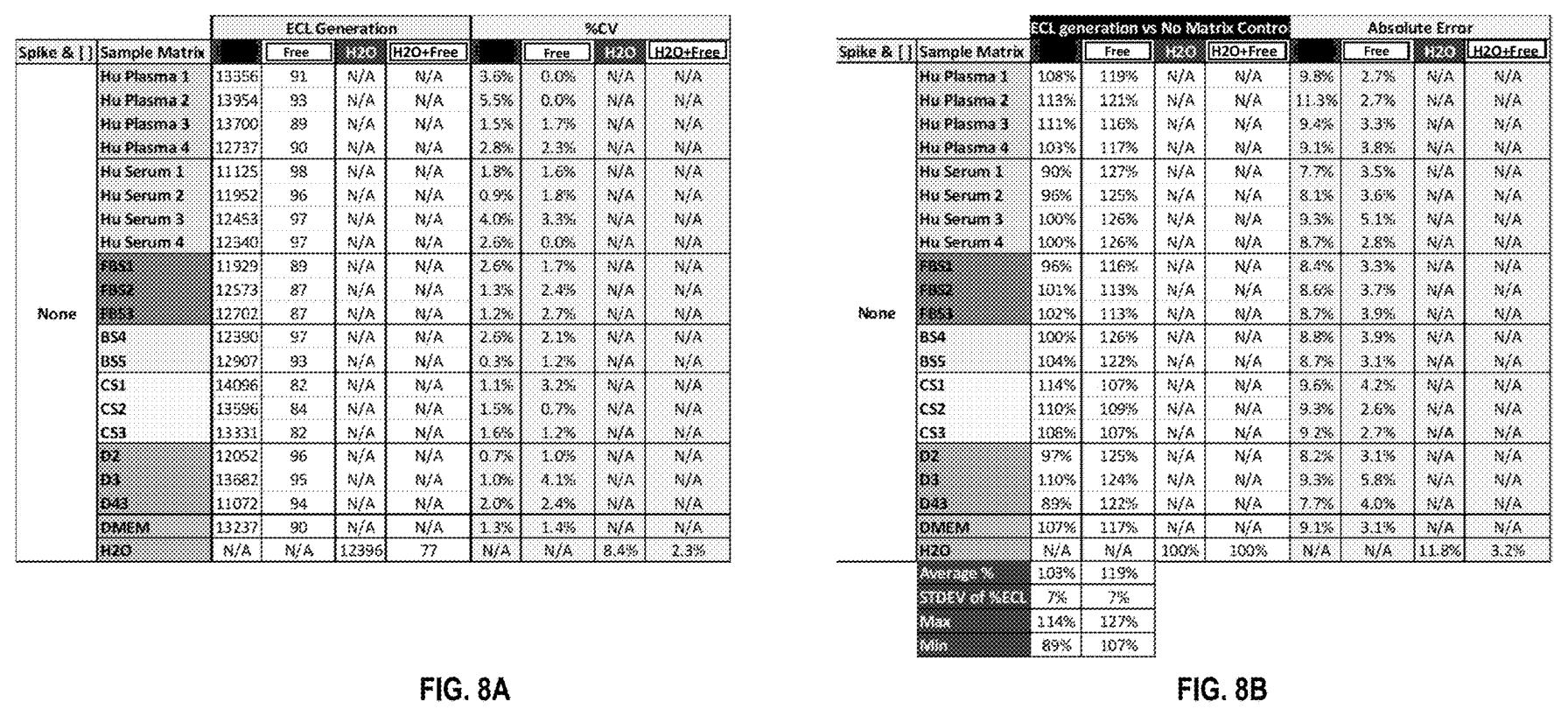

FIG. 8A shows the results of ECL signal generated from TEA read buffer with bound ("Bound") and free ECL label ("Free"), with different sample matrices. "H2O" indicates signal from a control with water instead of sample matrix added to a well before TEA read buffer. The column headers with "Free" indicates 6 nM of free ECL label in mock diluent. FIG. 8B shows the results of FIG. 8A normalized to ECL signal generated from an assay in which sample matrices were not added. The results indicate that all tested sample matrices (e.g., human, animal, and proteinaceous) minimally influenced ECL generation efficiency of TEA read buffer from bound ECL label when performed in 1-step non-wash assays, with an average signal change of less than 5%. The 6 nM of free ECL label in diluent was not detectable with the TEA read buffer, and the slight background signal increase appeared to be matrix dependent.

Figures 9A, 9B:
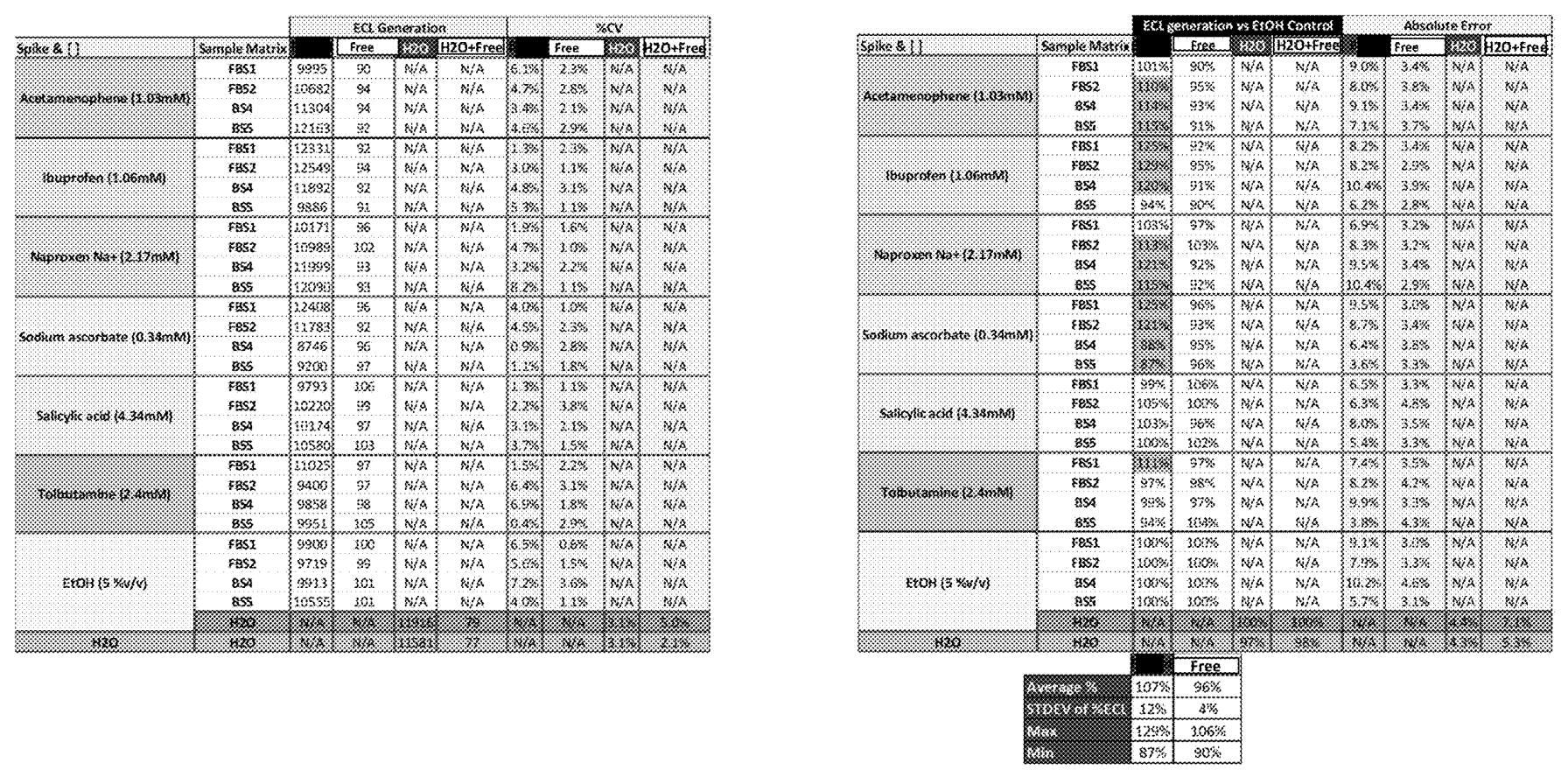

The sample matrices were then spiked with interferents (shown in FIG. 7B) at levels in excess of those commonly reported in human blood samples (see Lorenz et al., Diabetes Technology & Therapeutics 20 (5): 344-352 (2018)) and tested in the same manner as described above. FIG. 9A shows the results of ECL signal generated from TEA read buffer with bound and free ECL label with different interferents in different sample matrices. FIG. 9B shows the results of FIG. 9A normalized to ECL signal generated from an assay in which sample matrices and interferents were not added. The results indicate that the interferents in spiked FBS or BS showed minimal influence on the ECL generation efficiency of TEA read buffer from bound or free ECL label when performed in 1-step non-wash assays. The 6 nM free ECL label was barely detectable across all assays.

The sample matrix influence was tested on ECL generation from free ECL label at a higher concentration of 240 nM. FIG. 10A shows the results of ECL signal generated from TEA read buffer with free ECL label ("D3+STAG") in different sample matrices. FIG. 10B shows the results of FIG. 10A normalized to ECL signal generated from an assay in which sample matrices were not added. The sample matrices showed low influence on ECL generation efficiency of TEA read buffer from free ECL label when performed in 1-step non-wash assays, with an average change of less than 35%. The ECL signals from DMEM culture media and control free ECL label were lower than the human/animal serum or plasmas, which generated ~15 extra background counts. The higher signal for the proteinaceous human/animal serum or plasmas compared to the control signal was possibly due electrostatic attraction of ECL label to electrode adsorbed proteins. The lower ECL signal from DMEM could have been possibly due to phenol red dye interference. The results further confirm that human, animal, diluent, and culture matrices minimally influence TEA read buffer ECL generation efficiency in 1-step non-wash assays.

Figures 11A, 11B:
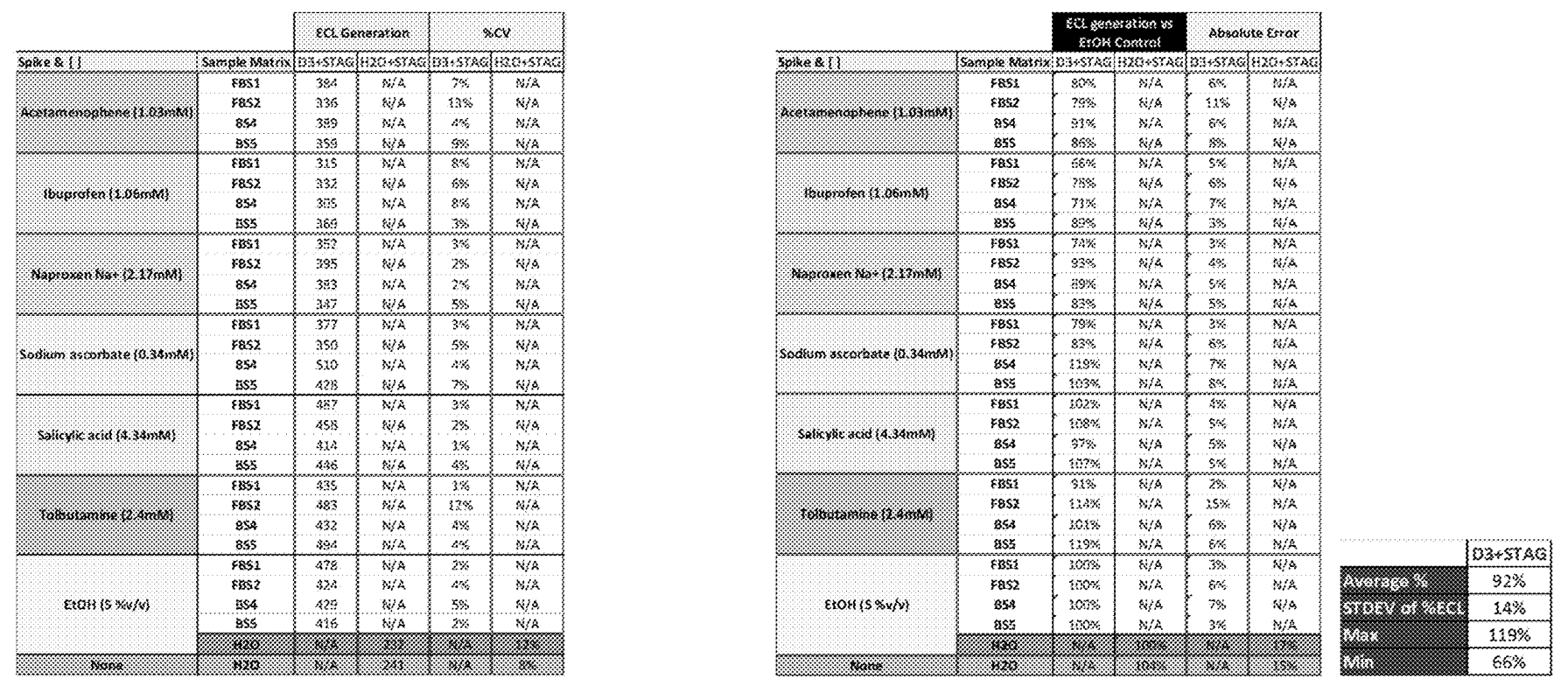

The higher concentration of free ECL label (240 nM) was tested with interferent-spiked sample matrices. FIG. 11A shows results of ECL signal generated from TEA read buffer with free ECL label with different interferents in different sample matrices. FIG. 11B shows the results of FIG. 11A normalized to ECL signal generated from an assay in which sample matrices and interferents were not added. The signal generation from free label using TEA read buffer remained low and consistent in the presence of the different interferents, when performed in 1-step non-wash assays. A small elevation in signal was observed in the interferent conditions relative to the control condition ("H2O" condition with no matrix and no interferent spike), which was an effect of the ethanol which was added to the matrix as the solvent for the interferents and not due to the interferents themselves.

Example 7. Combinatorial ECL Coreactant Measurements

Figure 12:
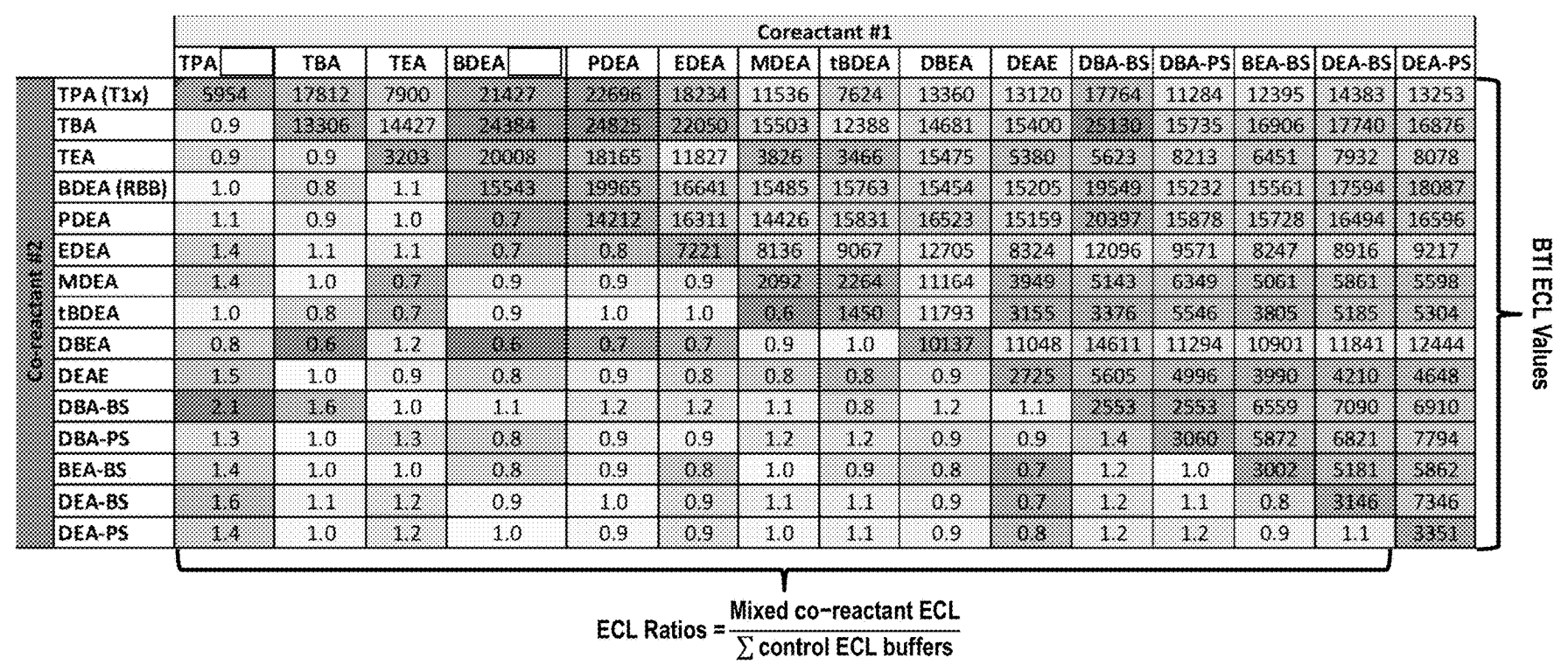

Combinations of ECL coreactants described in Example 1 were tested with a total concentration of 150 mM coreactant in 200 mM Tris, 50 mM KCl, 850 mM NaCl, 0.1% TRITON™ X-100, pH 7.8. Assays were performed with bound ECL label (BTI) as described in Example 1. Results are shown in FIG. 12. The top-right side of the chart in FIG. 12 shows the ECL signal generated from BTI, while the bottom-left side of the chart in FIG. 12 shows the ECL signal ratio of the mixed ECL coreactants to the sum of signal generated by the individual ECL coreactants. As shown in FIG. 12, combinations of TPA with other ECL coreactants showed possible non-linear effects.

Example 8. Sensitivity of ECL Coreactants to TRITON™ X-100 Presence

The ECL coreactants described in Example 1 were tested for sensitivity to the presence of TRITON™ X-100, which is required by the commonly-used ECL coreactant tripropylamine (TPA). Assays were performed with bound (BTI) and free (FT) ECL labels as described in Example 1. Results are shown in FIGS. 13A and 13B. FIG. 13A shows the ECL signal from BTI and FT for each ECL reactant in TRITON™ X-100 (TX100) and PEG(18) tridecyl ether (PEG18TDE), a non-electroactive surfactant. FIG. 13B shows the ratio of ECL generated in TRITON™ X-100 vs. PEG(18) tridecyl ether.

The compounds that were highly sensitive to TRITON™ X-100 were believed to have short radical cation lifetimes, and lower ECL signals were possibly due to poor electron transfer between the ECL label and coreactant, and/or rapid side reactions of ECL label/coreactant intermediates. Based on the results in FIGS. 13A and 13B, the ECL coreactants most sensitive to TRITON™ X-100 were: PIPES>>DEAE~=DBA-BS~=BEA-BS.

The present disclosure is not to be limited in scope by the specific embodiments described herein. Various modifications of the disclosure in addition to those described herein will become apparent to those skilled in the art from the foregoing description and accompanying figures. Such modifications are intended to fall within the scope of the claims. Various publications are cited herein, the disclosures of which are incorporated by reference in their entireties.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:
1. A composition comprising:
  a) 1000 mM to 6500 mM of triethanolamine (TEA);
  b) an ionic component; and
  c) an electrochemiluminescence (ECL)-labeled component;
  wherein the composition has a pH of 7 to 8.
2. The composition of claim 1, wherein the concentration of the TEA is 1200 mM to 1600 mM.
3. The composition of claim 1, wherein the concentration of the ionic component is 500 mM to 2000 mM.
4. The composition of claim 1, wherein the ionic component comprises a chloride ion.
5. The composition of claim 4, wherein the ionic component comprises NaCl, KCl, LiCl, or combination thereof.
6. The composition of claim 5, wherein the ionic component comprises NaCl.
7. The composition of claim 1, wherein the ECL-labeled component comprises a detection reagent that comprises an ECL label; or wherein the ECL-labeled component comprises a binding partner of a detection reagent, wherein the binding partner comprises an ECL label.
8. The composition of claim 7, wherein the ECL-labeled component is a detection reagent that comprises an ECL label.
9. The composition of claim 7, wherein the ECL label comprises an electrochemiluminescent organometallic complex.
10. The composition of claim 1, wherein the composition further comprises a surfactant.

11. The composition of claim 10, wherein the concentration of the surfactant is 0.1 mM to 10 mM.

12. The composition of claim 10, wherein the surfactant is a non-ionic surfactant.

13. The composition of claim 12, wherein the non-ionic surfactant is an alkyl ether-polyethylene glycol (PEG).

14. The composition of claim 1, wherein the composition has a pH of 7.9 to 8.

15. The composition of claim 1, wherein the composition has a pH of 7.9.

16. The composition of claim 1, wherein the composition is substantially free of an additional pH buffering component.

17. The composition of claim 1, wherein the composition does not comprise any of phosphate, Tris, HEPES, glycylglycine, borate, acetate, and citrate.

* * * * *